United States Patent [19]

Takaya et al.

[11] Patent Number: 4,871,730
[45] Date of Patent: Oct. 3, 1989

[54] CEPHEM COMPOUNDS

[75] Inventors: Takao Takaya, Kawanishi; Zenzaburo Tozuka, Toyonaka; Nobuyoshi Yasuda, Nishinomiya; Kohji Kawabata, Osaka, all of Japan

[73] Assignee: Fujisawa Pharmaceutical Co., Ltd., Osaka, Japan

[21] Appl. No.: 931,978

[22] Filed: Nov. 24, 1986

Related U.S. Application Data

[63] Continuation of Ser. No. 631,898, Jul. 18, 1974, abandoned.

[30] Foreign Application Priority Data

Aug. 1, 1983 [GB] United Kingdom ............... 8320673
Nov. 15, 1983 [GB] United Kingdom ............... 8330472

[51] Int. Cl.⁴ .................. C07D 501/36; A61K 31/545
[52] U.S. Cl. .................................... 514/206; 540/222; 540/225; 540/227; 514/203; 514/204
[58] Field of Search .................. 540/222, 225, 227

[56] References Cited

U.S. PATENT DOCUMENTS

| | | | |
|---|---|---|---|
| 3,929,780 | 12/1975 | Weir | 544/26 |
| 3,935,204 | 1/1976 | Dahlen et al. | 544/26 |
| 3,992,377 | 11/1976 | Chawrette et al. | 544/26 |
| 4,123,528 | 10/1978 | Cama et al. | 544/26 |
| 4,256,739 | 3/1981 | Woodward et al. | 544/26 |
| 4,425,340 | 1/1984 | Teraji et al. | 544/22 |

FOREIGN PATENT DOCUMENTS 57422 8/1982 European Pat. Off. ............ 544/27
8088386 5/1983 Japan ............................. 544/22

Primary Examiner—Nicholas S. Rizzo
Attorney, Agent, or Firm—Oblon, Spivak, McClelland, Maier & Neustadt

[57] ABSTRACT

A cephem compound of the formula:

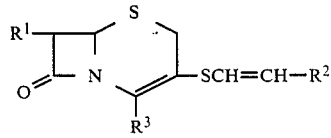

wherein $R^1$ is a group of the formula:

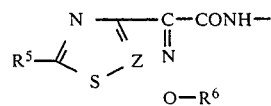

in which $R^5$ is amino or protected amino,
$R^6$ is hydrogen, lower alkyl, lower alkenyl, lower alkynyl, carboxy(lower) alkyl, protected carboxy(lower) alkyl, cyclo(lower) alkyl or cyclo (lower)alkenyl, and Z is CH or N;
$R^2$ is hydrogen, phenyl, pyridyl which may have a lower alkyl group, or cyano; and
$R^3$ is carboxy or protected carboxy; and pharmaceutically acceptable salt thereof.

11 Claims, No Drawings

CEPHEM COMPOUNDS

This application is a continuation, of application Ser. No. 631,898, filed July 18, 1984 now abandoned.

The present invention relates to new cephem compounds and pharmaceutically acceptable salts thereof. More particularly, it relates to new cephem compounds and pharmaceutically acceptable salts thereof, which have antimicrobial activities, to process for preparation thereof, to pharmaceutical composition comprising the same, and to a method of using the same therapeutically for the treatment of infectious diseases in human being and animals.

Accordingly, it is one object of the present invention to provide new cephem compounds and pharmaceutically acceptable salts thereof, which are highly active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds and pharmaceutically acceptable salt thereof are novel and can be represented by the following general formula (I):

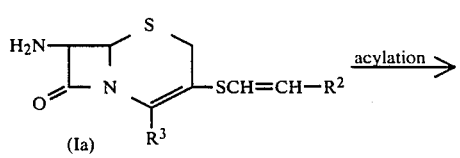

wherein
$R^1$ is amino or acylamino,
$R^2$ is hydrogen, aryl which may have suitable substituent(s), a heterocyclic group which may have suitable substituent(s) or cyano, and
$R^3$ carboxy or protected carboxy, and pharmaceutically acceptable salt thereof.

According to the present invention, the new cephem compound (I) can be prepared by various processes which are illustrated in the following schemes.

Process 1

or its reactive derivative
at the amino group
or a salt thereof

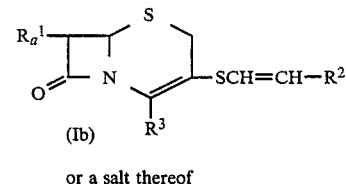

or a salt thereof

Process 2

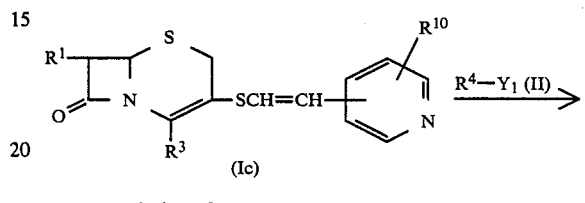

or a salt thereof

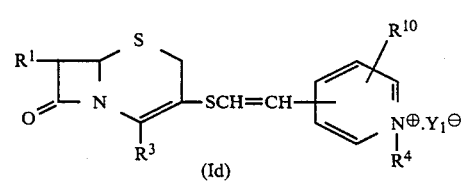

or a salt thereof

Process 3

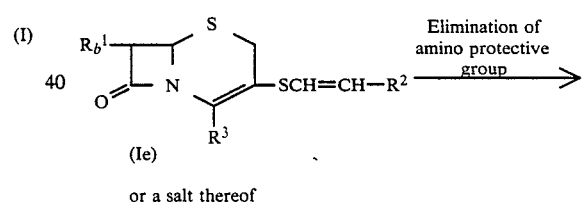

or a salt thereof (If)

or a salt thereof

Process 4

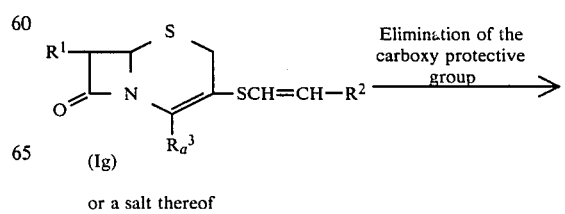

or a salt thereof

Process 5

(III) or a salt thereof + R²—CH=CH—SH (IV) or a salt thereof → (I) or a salt thereof

Process 6

(Ib) or a salt thereof —deacylation→ (Ia) or a salt thereof

Process 7

(Ih) or a salt thereof —Introduction of the carboxy protective group→ (Ig) or a salt thereof wherein $R^1$, $R^2$ and $R^3$ are each as defined above,
$R_a^1$ is acylamino,
$Y_1$ is an acid residue,
$R_1^4$ is lower alkyl or azido (lower) alkyl,
$R_b^1$ is acylamino having protected amino group,
$R_c^1$ is acylamino having amino group,
$R_a^3$ is protected carboxy,
$Y_2$ is an acid residue, and
$R^{10}$ is hydrogen or lower alkyl.

Among the starting compounds in the present invention, some of the compound (III) and the compound (IV) are novel and can be prepared by the processes which are illustrated in the following schemes.

Process A (V) or its reactive derivative at the amino group or a salt thereof (VI) or its reactive derivative at the carboxy group or a salt thereof → (IIIa) or a salt thereof

Process B

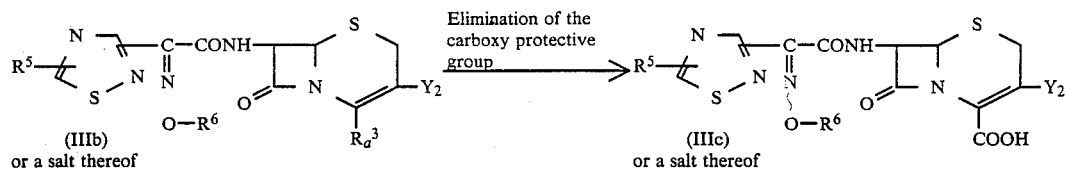

(IIIb) or a salt thereof → Elimination of the carboxy protective group → (IIIc) or a salt thereof Process C

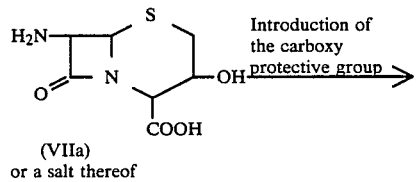

(VIIa) or a salt thereof — Introduction of the carboxy protective group →

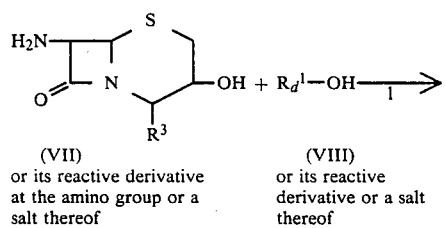

(VIIb) or a salt therof

Process D

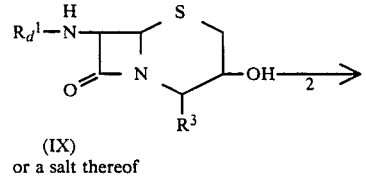

(VII) or its reactive derivative at the amino group or a salt thereof (VIII) or its reactive derivative or a salt thereof

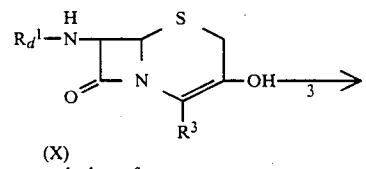

(IX) or a salt thereof (X) or a salt thereof

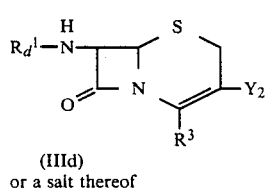

(IIId) or a salt thereof

Process E

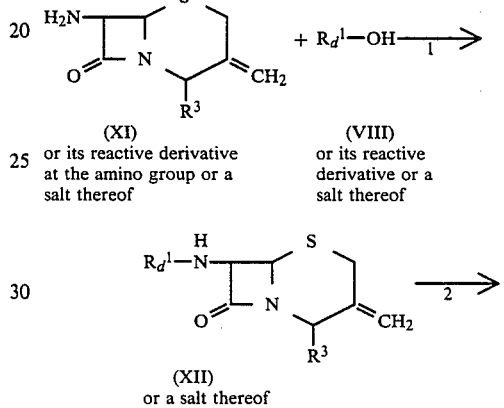

(XI) or its reactive derivative at the amino group or a salt thereof (VIII) or its reactive derivative or a salt thereof (XII) or a salt thereof (X) or a salt thereof Process F

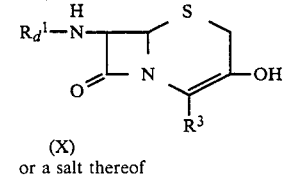

(XIIa) or a salt thereof

Introduction of the carboxy protective group →

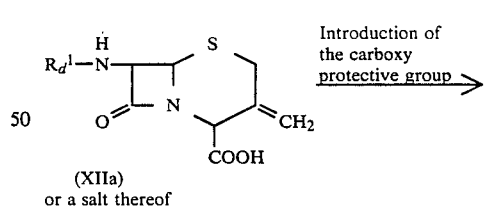

(XIIb)

Process G

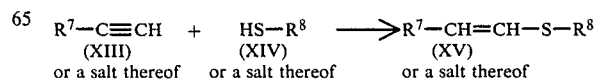

$R^7-C\equiv CH$ + $HS-R^8$ → $R^7-CH=CH-S-R^8$
(XIII) (XIV) (XV)
or a salt thereof   or a salt thereof   or a salt thereof

Process H

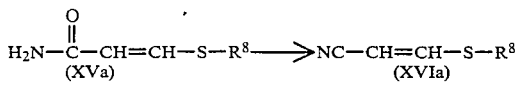

Process I

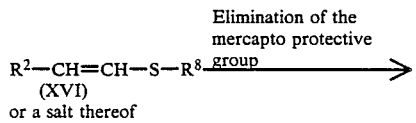

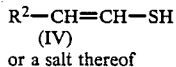

wherein $R^2$, $R^3$, $R_a^3$, and $Y_2$ are each as defined above, $R^5$ is amino or protected amino, $R^6$ is hydrogen or an organic group which may have suitable substituent(s), and $R_d^1$ is lower alkanoyl, $R^7$ is aryl which may have suitable substituent(s), a heterocyclic group which may have suitable substituent(s), cyano or carbamoyl, and $R^8$ is mercapto protective group.

Suitable pharmaceutically acceptable salts of the object compound (I) are conventional non-toxic salts and may include a salt with a base or an acid addition salt such as a salt with an inorganic base, for example, an alkali metal salt (e.g. lithium salt, sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.);

an organic carboxylic or sulfonic acid addition salt (e.g. formate, acetate, trifluoroacetate, maleate, tartrate, methanesulfonate, benzenesulfonate, p-toluene-sulfonate, etc.); a salt with a basic or acidic amino acid (e.g. arginine, aspartic acid, glutamic acid, etc.);

an intermolecular or intramolecular quaternary salt, and the like. The said intermolecular quaternary salt can be formed in case that the heterocyclic group in $R^2$ in the compound (I) contains nitrogen atom(s) (e.g. pyridyl, etc.), and suitable intermolecular quaternary salt may include 1-lower alkylpyridinium lower alkylsulfate (e.g. 1-methylpyridinium methylsulfate, 1-ethylpyridinium ethylsulfate, etc.), 1-lower alkylpyridinium halide (e.g. 1-methylpyridinium iodide, etc.), di(lower-)alkylpyridinium halid (e.g. 1,2-dimethylpyridinium iodide, 1,2-diethylpyridinium iodide, etc.), 1-azido(-lower)-alkylpyridinium trihalo (lower) alkanesulfonate [e.g. 1-azidomethylpyridinium trifluoromethanesulfonate, 1(2-azidoethyl) pyridinium trifluoromethanesulfonate, etc.) and the like. The said intramolecular quaternary salt can be formed in case that heterocyclic group in $R^2$ in the compound (I) contains nitrogen atom(s) (e.g. pyridyl etc.) and $R^3$ is carboxy, and suitable intramoleculer quaternary salt may include 1-lower alkylpyridinium carboxylate (e.g. 1-methylpyridinium carboxylate, 1-ethylpyridinium carboxylate, 1-propylpyridinium carboxylate, 1-isopropylpyridinium carboxylate, 1-butylpyridinium carboxylate, etc.), di(lower) alkylpyridinium carboxylate (e.g. 1,2-dimethylpyridinium carboxylate, 1,2-diethylpyridinium carboxylate, etc.), 1-azido (lower)-alkylpyridinium carboxylate [e.g. 1-azidomethylpyridinium carboxylate, 1-(2-azidoethyl)pyridinium carboxylate, etc.) and the like.

In the above and subsequent description of the present specification, suitable examples and illustration of the various definitions which the present invention include within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated. Suitable "acyl" moity in the terms "acylamino", "acylamino having protected amino group" and "acylamino having amino group" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Alliphatic acyl such as lower or higher alkanoyl (e.g. formyl, acetyl, succinyl, hexanoyl, heptanoyl, valeryl, stearoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.);

lower of higher alkoxysulfonyl (e.g. methoxysulfonyl, ethoxysulfonyl, etc.); or the like;

Aromatic cycle such as aroyl (e.g. benzoyl, toluoyl, naphthoyl, etc.);

ar(lower)alkanoyl such as phenyl(lower)alkanoyl (e.g. phenylacetyl, phenylpropionyl, etc.);

aryloxycarbonyl (e.g. phenoxycarbonyl, naphthyloxy carbonyl, etc.);

aryloxy(lower)alkanoyl (e.g. phenoxyacetyl, phenoxypropionyl, etc.);

arylglyoxyloyl (e.g. phenylglyoxyloyl, naphthylglyoxyloyl, etc.);

arenesulfonyl (e.g. benzenesulfonyl, p-toluensulfonyl, etc.); or the like;

Heterocyclic acyl such as heterocycliccarbonyl ( e.g. thenoyl, furoyl, nicotinoyl, etc.);

heterocyclic (lower)alkanoyl (e.g. thienylacetyl, thiazolylacetyl, thiadiazolylacetyl, tetrazolylacetyl, etc.); heterocycliglyoxyloyl (e.g. thiazolyglyoxyloyl, thienylglyoxyloyl, etc.); or the like; in which suitable heterocyclic moitey in the terms "heterocycliccabonyl", "heterocyclic(lower)alkanoyl" and "heterocyclicglyoxyloyl" as mentioned above means, in more detail, saturated or unsaturated, monocyclic or polyciclic heterocyclic group containing at least one hetero-atom such as an oxygen, sulfur, nitrogen atom and the like.

And, especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotirazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atoms(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 to 6-membered) heteromonocyclic group containing an oxygen atom, for example, furyl, etc.;

unsaturated 3 to 8-membered (more preferably 5 to 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

As to the heterocyclic group as mentioned above, the following points are to be noted. That is, in case that the heterocyclic group is specifically thiazolyl or thiadiazolyl group having amino or protected amino as a substituent in its molecule, said thiazolyl or thiadiazolyl group include tautomeric isomers, which are caused by the specific behavior of the thiazole or thiadiazole ring. That is, for example, said amino or protected aminothiazolyl or thiadiazolyl group is represented by the formula:

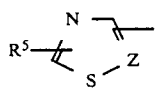
(A)

(wherein $R^5$ is defined above and Z is CH or N), and in case that the group of the formula (A) takes the formula:

(A')

(wherein $R^5$ and Z are each as defined above), said group of the formula (A') can also be alternatively represented by its tautomeric formula:

(A'')

(wherein Z is as defined above and $R^{5'}$ is imino or protected imino). That is, both of the said group of the formulae (A') and (A'') are in the state of tautomeric equilibrium which can be represented by the following equilibrium:

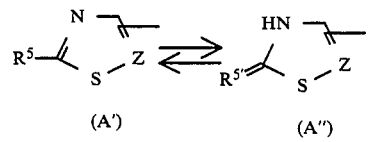

(A')                (A'')

(wherein $R^5$, Z and $R^{5'}$ are each as defined above).

These types of tautomerism between 2-aminothiazole or 5-aminothidiazole compounds and 2-iminothiazoline or 5-iminothiadiazoline compounds as stated above have been well known in the arts, and it is obvious to a person skilled in arts that both of the tautomeric isomers are equilibrated and lie in the reciprocally convertible state, and accordingly it is to be understood that such isomers are included within the same category of the compound per se. Accordingly, the both of the tautomeric forms are clearly included within the scope of the present invention. In the present specification, the object and starting compounds including the group of such tautomeric isomers are represented by using one of the expressions therefor, i.e. 2-amino (or protected amino) thiazolyl or 5-amino (or protected amino) thiadiazolyl and the formula:

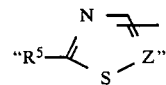

only for the convenient sake.

The acyl moiety as stated above may have one to ten, same or different, suitable substituent(s) such as lower alkyl (e.g. methyl, ethyl, etc.);

lower alkoxy (e.g. methoxy, ethoxy, propoxy, etc.);
lower alkythio (e.g. methylthio, ethylthio, etc.);
lower alkylamino (e.g. methylamino, etc.); cyclo(lower) alkyl (e.g. cyclopentyl, cyclohexyl, etc.);
cyclo (lower) alkenyl (e.g. cyclohexenyl; cyclohexadienyl, etc.); halogen; amino; protected amino; hydroxy;
protected hydroxy; cyano; nitro; carboxy; protected carboxy; sulfo; sulfamoyl; imino; oxo;

amino(lower)alkyl (e.g. aminomethyl, aminoethyl, etc.);

carbamoyloxy; hydroxy(lower)alkyl (e.g. hydroxymethyl, 1 or 2-hydroxyethyl, 1 or 2 or 3-hydroxypropyl, etc.); cyano(lower)alkenylthio (e.g. cyanovinylthio, etc.); a group of the formula: =N—OR$^6$ wherein R$^6$ is as defined above, or the like.

In this connection, when the acyl moiety has a group of the formula: =N—OR$^6$, wherein R$^6$ is as defined above, as substituent(s), there are geometrical isomers (syn and anti isomers) due to the presence of double bond. And, for example, the syn isomer means one geometrical isomer having the group of the formula:

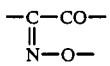

and the corresponding anti isomer means the other geometrical isomer having the group of the formula:

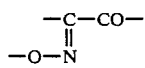

Suitable "aryl" in the term "aryl which may have suitable substituent(s)" may include phenyl, tolyl, xylyl, cumenyl, naphtyl and the like. Suitable "substituent(s)" in the term "aryl which may have suitable substituent(s)" may include hydroxy, halogen (e.g., fluorine, chlorine, bromine or iodine) and the like.

Suitable "heterocyclic group" in the term "a heterocyclic group which may have suitable substituent(s)" may include lower alkyl (e.g., methyl, ethyl, propyl, isopropyl, butyl, isobutyl, t-butyl, pentyl, hexyl, etc.), azido(lower)alkyl (e.g., azidomethyl, 2-azidoethyl, etc.) and the like.

Suitable "protected carboxy" may include esterified carboxy wherein "esterified carboxy" can be referred to the ones as mentioned below.

Suitable example of the ester moiety of an esterified carboxy may be the ones such as lower alkyl ester (e.g. methyl ester, ethyl ester, propyl ester, isopropyl ester, butyl ester, isobutyl ester, tertbutyl ester, pentyl ester, hexyl ester, 1-cyclopropylethyl ester, etc.) which may have at least one suitable substituent(s), for example, lower alkanoyloxy (lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-butyryloxyethyl ester, 1(or 2) -isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono (or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl 2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.);

lower alkynyl ester (e.g. ethynyl ester, propynyl ester, etc.);

ar(lower)alkyl ester which may have at least one suitable substituent(s) such as mono (or di or tri)phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.);

aryl ester which may have at least one suitable substituent(s) (e.g. phenyl ester, 4-chlorophenyl ester, tolyl ester, tert-butylphenyl ester, xylyl ester, mesityl ester, cumenyl ester, etc.);

phthalidyl ester; and the like. Suitable "lower alkyl" may include methyl, ethyl, propyl, isopropyl, butyl, isobutyl, t-butyl, pentyl, hexyl and the like.

Suitable "protected amino" and "protected amino moiety" in the term "acylamino having protected amino group" may include acylamino wherein "acyl" moiety can be referred to the ones as mentioned above, phosphonoamino, protected phosphonoimino, ar(lower)-alkylamino such as benzylamino, phenethylamino, tritylamino; and the like.

Suitable "acid residue" may include acyloxy, halogen (e.g., flourine, chlorine, bromine or iodine) and the like, wherein acyl moiety in the term "acyloxy" can be referred to the ones as exemplified above.

Suitable "lower alkanoyl" may include formyl, acetyl, propionyl and the like.

Suitable "organic group which may have suitable substituent(s)" may include lower alkyl (e.g. methyl, ethyl, propyl, etc.), lower alkenyl (e.g. vinyl, allyl, 2butenyl, etc.), lower alkynyl (e.g. ethynyl, 2-propynyl, etc.), cyclo(lower)alkyl (e.g. cyclopropyl, cyclobutyl, cyclopentyl, cyclohexyl, etc.), cyclo(lower)alkenyl (e.g., cyclobutenyl, cyclopentenyl, cyclohexenyl, etc.), ar(lower)alkyl such as phenyl(lower)alkyl (e.g. benzyl, phenethyl, etc.), carboxy (lower) alkyl (e.g. carboxymethyl, 1-carboxyethyl, carboxypropyl, etc.), protected carboxy (lower) alkyl such as esterified carboxy(lower)alkyl [e.g. mono(or di or tri)phenyl(lower)-alkoxycarbonylmethyl, nitrophenyl(lower)alkoxycarbonylmethyl, etc.], hydroxy(lower)alkyl (e.g. hydroxymethyl, hydroxyethyl, etc.), carboxy(lower)alkenyl (e.g. carboxyvinyl, carboxyallyl, carboxy-2-butenyl, etc.), protected carboxy (lower) alkenyl, and the like.

suitable "mercapto protective group" may include a conventional protective group such as lower alkyl as mentioned above; mono(or di or tri) phenyl(lower)alkyl (e.g., benzyl, phenethyl, phenylpropyl, trityl, etc.);

acyl, for example, lower alkanoyl (e.g., formyl, acetyl etc.) and the like.

Preferred embodiments of the object compound (I) are as follows.

Preferred embodiment of R$^1$ is amino, lower alkanoylamino, aminothiadiazolyl(lower)alkanoylamino having a lower alkoxyimino group, aminothiadiazolyl(lower)alkanoylamino having a lower alkenyloxyimino group, aminothiadiazolyl-(lower)alkanoylamino having a lower alkynyloxyimino group, aminothiadiazolyl(lower)alkanoylamino having a carboxy(lower)alkoxyimino group, aminothiadiazolyl-(lower)alkanoylamino having a cyclo(lower)alkenyloxyimino group, aminothiadiazolyl(lower)alkanoylamino having a cyclo(lower)alkoxyimino group, aminothiadiazolyl-(lower)alkanoylamino having a hydroxyimino group, protected aminothiazolyl(lower)alkanoylamino having a lower alkoxyimino group [more preferably acylaminothiazolyl(lower)alkanoylamino having a lower alkoxyimino group, more preferably lower alkanoylaminothiazolyl(lower) alkanoylamino having a lower alkoxyimino group or trihalo(lower)alkanoylaminothiazolyl(lower)alkanoylamino having a lower alkoxyimino group], aminothiazolyl(lower)alkanoylamino having a lower alkoxyimino group, protected aminothiazolyl(lower)-alkanoylamino having a lower alkenyloxyimino group [more preferably acylaminothiazolyl(lower)alkanoylamino having a lower alkenyloxyimino group, most preferably lower alkanoylaminothiazolyl(lower)alkanoylamino having a lower alkenyloxymino group], aminothiazolyl(lower)-alkanoylamino having a lower alkenyloxyimino group, protected aminothiazolyl(lower)alkanoylamino having a lower alkynyloxyimino group [more preferably acylaminothiazolyl(lower)alkanoylamino having a lower alkynyloxyimino group, most preferably lower alkanoylaminothiazolyl(lower)alkanoylamino having a lower alkynyloxyimino group], aminothiazolyl(lower)-alkanoylamino having a lower alkynyloxyimino group, protected aminothiazolyl (lower) alkanoylamino having a protected carboxy (lower) alkoxyimino group [more preferably acylaminothiazolyl(lower)alkoxyimino having an esterified carboxy(lower)alkoxyimino group, most preferably acylaminothiazolyl(lower)alkanoylamino having a mono (or di or tri)phenyl(lower)alkoxycarbonyl(lower)alkoxyimino group or trihalo(lower)-alkanoylaminothiazolyl(lower)alkoxyimino having a nitrophenyl(lower)alkoxycarbonyl(lower)alkoxyimino group], aminothiazolyl(lower)alkanoylamino having a protected carboxy(lower)alkoxyimino group [more preferably aminothiazolyl(lower)alkanoylamino having an esterified carboxy(lower)alkoxyimino group, most preferably aminothiazolyl(lower)alkoxyimino having a mono(or di or tri)phenyl(lower)alkoxycarbonyl(lower)-alkoxyimino group], aminothiazolyl(lower)alkanoylamino having a carboxy(lower)alkoxyimino group, protected aminothiazolyl (lower) alkanoylamino having a carboxyl(lower)alkoxyimino group [more preferably acylaminothiazolyl(lower)alkanoylamino having a carboxy(lower)alkoxyimino group, most preferably trihalo(lower)alkanoylaminothiazolyl(lower)alkanoylamino having a carboxy(lower)alkoxyimino group], protected aminothiazolyl(lower)alkanoylamino having a cyclo(lower)alkenylixyimino group [more preferably acylaminothiazolyl(lower)alkanoylamino having a cyclo(lower)alkenyloxyimino group, most preferably lower alkanoylaminothiazolyl(lower)alkanoylamino having a cyclo(lower)alkenyloxyimino group], aminothiazolyl-(lower)alkanoylamino having a cyclo(lower)alkenyloxyimino group, protected aminothiazolyl (lower) alkanoylamino having a hydroxy(lower)alkyl group [more preferably ar(lower)-alkylaminothiazolyl(lower)alkanoylamino having a hydroxy(lower)alkyl group], aminothiazolyl(lower)-alkanoylamino having a hydroxy(lower)alkyl group, hydroxyphenyl(lower)alkanoylamino having a protected amino group [more preferably hydroxyphenyl(lower)-alkanoylamino having an acylamino group, most preferably hydroxyphenyl(lower)alkanoylamino having a piperazinylcarbonylamino substituted with dioxo and a lower alkyl group], phenyl(-lower)alkanoylamino or cyano(lower)alkenythio(-lower)alkanoylamino;

$R^2$ is pyridyl, lower alkylpyridyl, aryl [more preferably phenyl], cyano or hydrogen; and $R^3$ is carboxy or protected carboxy [more preferably esterified carboxy, most preferably mono (or di or tri)phenyl(lower)alkoxycarbonyl , nitrophenyl-(lower)alkoxycarbonyl or lower alkanoyloxy(lower)-alkoxycarbonyl].

Suitable intramolecular or intermolecular quaternary salt of the object compound (I) may include mono(or di or tri)phenyl(lower)alkyl 7-[2-(2-protected aminothiazol-4-yl)-2-lower alkoxyiminoacetamido]-3-[2-(1-lower alkyl-3-pyridino)vinylthio)-3-cephem-4 -carboxylate halide, mono(or di or tri)phenyl(lower)-alkyl 7-[2-(2-aminothiazol-4-yl)-2-lower alkoxyiminoacetamido]3-[2-(1-lower alkyl-3-pyridinio)vinylthio]3-cephem-4-carboxylate halide, mono (or di or tri)-phenyl(lower)alkyl 7-[2-(2-protected aminothiazol-4-yl)2-protected carboxy(lower)alkoxyiminoacetamido]-3-[2-(1-lower alkyl-3-pyridinio)vinylthio]-3-cephem-4-carboxylate halide, mono(or di or tri)phenyl(lower)alkyl 7-[2-(2-aminothiazol-4-yl)-2-protected carboxy(lower)-alkoxyiminoacetamido]-3-[2-(1-lower alkyl-3-pyridinio]vinylthio]-3-cephem-4-carboxylate halide, mono(or di or tri)phenyl(lower)alkyl 7-[2-(5-amino-1,2,4-thiadiazol-3-yl)-2-lower alkoxyiminoacetamido]-3-cephem-4-carboxylate halide, mono (or di or tri)phenyl(lower)alkyl 7-[2-(5-amino-1,2,4-thiadiazol-3-yl)-2-(lower) alkoxyiminoacetamido]3-[2-(1-lower alkyl-3-pyridinio) vinylthio]-3-cephem-4carboxylate halide, mono(or di or tri)phenyl(lower)alkyl 7-[2-(2-protected aminothiazol-4-yl)-2-lower alkoxyiminoacetamido]-3-[2-{1,2-di(lower)alkyl-5-pyridinio} vinylthio]-3-cephem-4-carboxylate halide, mono(or di or tri)phenyl(lower)alkyl 7-[2-(2-aminothiazol-4-yl)-2-lower alkoxyiminoacetamido]-3-[2-{1,2-di(lower alkyl-5-pyridinio}vinylthio]-3-cephem-4 -carboxylate halide, mono(or di or tri)phenyl(lower)alkyl 7-[2-(2-protected aminothiazol-4-yl)-2-lower alkoxyiminoacetamido]-3-[2-{1,2-di(lower)alkyl-5-pyridinio} vinylthio]-3-cephem-4-carboxylate halide, mono(or di or tri)phenyl(lower)alkyl 7-[2-(2-aminothiazol-4-yl)-2-lower alkoxyiminoacetamido]-3-[2-{1,2-di(lower)alkyl-5-pyridinio}vinylthio]-3-cephem-4-carboxylate halide, mono(or di or tri)phenyl(lower)alkyl 70[2-(2-protected aminothiazol4-yl)-2-lower alkoxyiminoacetamido]-3-[2-{1-azido(lower)alkyl-3-pyridinio}vinylthio]-3-cephem-4-carboxylate trihalo(lower)alkanesulfonate, mono(or di or tri)phenyl(lower)alkyl 7-[2-(2-aminothiazol-4-yl)-2-lower alkoxyiminoacetamido]-3-[2-{1-azido(lower)alkyl-3-pyridinio}vinylthio]-3-cephem-4-carboxylate trihalo(lower)alkanesulfonate, mono(or di or tri)phenyl(lower)alkyl 7-2-(5-amino-1,2,4-thiadiazol-3-yl)-2-lower alkoxyiminoacetamido]-3-[2-{1,2-di(lower)alkyl-5-pyridinio}vinylthio]-3-cephem-4-carboxylate halide, 7-[2-aminothiazol-4-yl)-2-lower alkoxyiminoacetamido -3-[2-(1-lower alkyl-3-pyridinio)vinylthio]-3-cephem-4-carboxylate, 7-[2-(2-aminothiazol-4-yl)-2-carboxy(lower)-alkoxyiminoacetamido]-3-[2-(1-lower alkyl-3-pyridinio)-vinylthio -3-cephem-4-carboxylate, 7-[2-(5-amino-1,2,4-thiadiazol-3-yl)-2-lower alkoxyiminoacetamido -3-[2-(1-lower alkyl-3-pyridinio)vinylthio]-3-cephem-4-carboxylate, 7-[2-(5-amino-1,2,4-thiadiazol-3-yl)-2-(lower alkenyloxy-imino)acetamido]-3-[2-(1-lower alkyl-3-pyridinio)-vinylthio]-3-cephem-4-carboxylate, 7-[2-(5-amino-1,2,4-thiadiazol-3-yl)-2-carboxy(lower)alkoxyiminoacetamido]-3-[2-(1-lower alkyl-3-pyridinio)-vinylthio]-3-cephem-4-carboxylate, 7-[2-(2-aminothiazol-4-yl)-2-lower alkoxyiminoacetamido]-3-[2-{1,2-di(lower)alkyl-5-pyridinio}vinylthio]-3-cephem-4-carboxylate, 7-[2-(2-aminothiazol-4-yl)-2-lower alkoxyiminoacetamido] 3-[2-{1,2-di(lower)alkyl-5-pyridinio} vinylthio]-3-cephem-4-carboxylate, 7-[2-(2-aminothiazol-4-yl)-2-lower alkoxyiminoacetamido]-3-[2-{1-azido(lower)alkyl3-pyridinio}vinylthio]-3-cephem-4-carboxylate, 7-[2-(5-amino-1,2,4-thiadiazol-3yl)-2-lower alkoxyiminoacetamido]3-[2-{1,2-di(lower)alkyl-5-pyridinio} vinylthio]-3-cephem-4-carboxylate, and the like.

The process for preparing the object compounds of the present invention are explained in detail in the following.

Process 1

The object compound (Ib) or a salt thereof can be prepared by subjecting the compound (Ia) or its reactive derivative at the amino group or a salt thereof to acylation reaction.

Suitable reaction derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as bis(trimethylsilyl)acetamide, mono(-trimethylsilyl)acetamide, bis(trimethylsilyl)urea or the like; a derivative formed by reaction of the compound (Ia) with phosphorus trichloride or phosgene, and the like.

Suitable acylating agent to be used in the present acylation reaction may include conventional one and can be shown by the formula: $R^9$—OH (XVII) (wherein $R^9$ is acyl) or its reactive derivative or a salt thereof.

Suitable salts of the compounds (Ia) and (Ib) can be referred to the ones as exemplified for the compound (I).

Suitable salt of the compound (XVII) may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N, N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

Suitable reactive derivative of the compound (XVII) may include an acid halide, an acid anhydride, an activated amide, an activated ester, and the like.

The suitable example may be an acid chlorid; an acid azide; a mixed acid anhydride with an acid such as substituted phosphoric acid (e.g. diakylphosphoric acid, phenylphosphoric acid, diphenylphosphoric acid, dibenzylphosphoric acid, halogenated phosphoric acid etc.), diakylphosphorous acid, sulfurous acid, thiosulfuric acid, sulfuric acid, sulfonic acid (e.g. methanesulfonic acid, etc.), alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.);

a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl

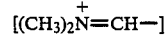

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotrazole, etc.), and the like.

These reactive derivatives can optionally be selected from them according to the kind of the compound (XVII) to be used.

The reaction is usually carried out in a conventional solvent such as water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

When the compound (XVII) is used in free acid form or its salt form in the reaction, the reaction is preferably carried out in the presence of a conventional condensing agent such as N, N'-dicyclohexylcarbodiimide;

N-cyclohexyl-N'-morpholinoethylcarbodiimide;

N-cyclohexyl-N'-(4-diethylaminocyclohexyl)carbodiimide;

N, N'-diethylcarbodimiide, N, N'-diisopropylcarbodiimide;

N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine;

ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride;

triphenylphosphine; 2-ethyl-7-hydroxybenzisoxazolium salt;

2-ethyl-5-(m-sulfophenyl) isoxazolium hydroxide intra-molecular salt; 1-(p-chlorobenzenesulfonyloxy)-6-chloro-1H-benzo-triazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

Process 2

The object compound (Id) or a salt thereof can be prepared by reacting the compound (Ic) or a salt thereof with the compound (II).

Suitable salt of the compound (Ic) can be referred to the ones as exemplified for the compound (XVII).

Suitable salt of the compound (Id) can be referred to the ones as exemplified for the compound (I).

The reaction is usually carried out in a solvent such as water, acetone, tetrahydrofuran, ethanol, ether, N,N-dimethylformide or any other solvent which does not adversely influence the reaction.

The reaction temperature is not critical and the reaction is usually carried out under cooling to heating.

The present invention includes, within the scope of the invention, a case that the compound (Id) wherein $R^3$ is carboxy is transformed into its intramolecular quaternary salt by conventionaal method, e.g., by treating the compound (Id) with base.

Process 3

The object compound (If) or a salt thereof can be prepared by subjecting the compound (Ie) or a salt thereof to elimination reaction of amino protective group.

suitable salts of the compounds (Ie) and (If) can be referred to the ones as exemplified for the compound (I).

The present elimination reaction is carried out in accordance with a conventional method such as hydrolysis; reduction; a method by reacting the compound (Ie) wherein the protective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarboyl, t-butoxycarbonyl, etc.), alkanoyl (e.g. formyl, etc.), cycloalkoxycarbonyl, substituted or unsubstituted aralkoxycarbonyl, (e.g. benzyloxycarbonyl, substituted benzyloxycarbonyl, etc.), ar(lower)alkyl (e.g. benzyl, trityl, etc.) or the like.

Suitable acid may include an organic or an inorganic acid, for example, formic acid, trifluoroacetic acid, benzenesulfonic acid, p-toluenesufonic acid, hydrochloric acid and the like, and preferable acid is, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent (e.g. methanol, ethanol, tetrahydrofuran, etc.), water or a mixture thereof. When trifluoracetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g. dichloroacetyl, trifluoracetyl, etc.) etc. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.) alkali metal carbonate (e.g. sodium carbonate, potassium carbonate, cesium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo [4,3,0]non-5-ene, 1,4-diazabicyclo [2,2,2]octane, 1,5-diazabicyclo[5,4,-0]undecene-5 or the like. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g. sodium borohydride, etc.) and the like.

The reaction temperature is not critical and may be suitably selected in accordance with the kind of the protective group of the amino group and the elimination method as described above, and the present reaction is preferably carried out under a mild condition such as under cooling, at ambient temperature or slightly elevated temperature.

Process 4

The object compound (Ih) or a salt thereof can be prepared by subjecting the compound (Ig) or a salt thereof to elimination reaction of the carboxy protective group.

Suitable salts of the compounds (Ig) and (Ih) can be referred to the salt exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid including Lewis acid. Suitable base may include an inorganic base, and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]non -5-ene, 1,4diazabicyclo[2,2,2]octane, 1,8-diazabicyclo[5,4,0]undecene-7, or the like. Suitable acid may include an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, etc.). The elimination using Lewis acid such as trihaloacetic acid (e.g. trichloroacetic acid, trifluoroacetic acid, etc.) or the like is preferably carried out in the presence of cation trapping agents (e.g. anisole, phenol, etc.).

The reaction is usually carried out in a solvent such as water, an alcohol (e.g. methanol, ethanol, etc.), methylene chloride, tetrahydrofuran, a mixture thereof or any other solvent which does not adversely influence the reaction. A liquid base or acid can also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromus chloride, chromus acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.). The present invention includes, within the scope of the invention, a case that the protected carboxy(-lower)alkoxyimino group or cyclo(lower)-alkenyloxyimino group in $R^1$ is converted into carboxy(lower)alkoxyimino group or hydroxyimino group respectively during this reaction or the post-treating step of this reaction.

Further, the present invention includes, within the scope of the invention, a case that the compound (Ih) in a form of intramolecular quaternary salt is transformed into its intramolecular quaternary salt by a conventional method, e.g., by treating the compound (Ih) with base.

Process 5

The object compound (I) or a salt thereof can be prepared by reacting a compound (III) or a salt thereof with a compound (IV) or a salt thereof.

Suitable salt of the compound (III) can be referred to the ones as exemplified for the compound (XVII).

Suitable salt of the compound (IV) may include the ones as exemplified for the compound (I) and silver salt. The reaction may be carried out in the presence of sodium iodide, sodium thiocyanate and the like.

The reaction is usually carried out in a solvent such as water, acetone, chloroform, nitrobenzene, methylene chloride, ethylene chloride, acetonitrile, N,N-dimethylformamide, methanol, ethanol, ether, tetrahydrofuran or any other conventional solvents which do not adversely influence the reaction. When the compound (III), which has amino and/or carboxy, is used in the present reaction, the said compound (III) is, in advance, preferably treated with the silyl compound such as bis(trimethylsilyl)acetamide, mono(trimethylsilyl)acetamide, bis(trimethylsilyl)-urea or the like.

When the compound (IV) is used in free form in the reaction, the reaction is preferably carried out in the presence of a base, for example, an organic or an inorganic base such as alkali metal hydroxide, alkali metal carbonate, alkali metal bicarbonate, alkali metal alkoxide (e.g., sodium methoxide, sodium ethoxide etc.), trialkylamine, pyridine or the like, and preferably carried out around neutral conditions. The reaction temperature is not critical and the reaction is usually carried out under cooling, at ambient temperature or under warming.

Process 6

The compound (Ia) or a salt thereof can be prepared by subjecting the compound (Ib) or a salt thereof to deacylation reaction.

This reaction can be carried out in a similar manner to that of aforementioned Process 3.

Process 7

The compound (Ig) or a salt thereof can be prepared by introducing a carboxy protective group into the compound (Ih) or a salt thereof.

An introducing agent of a carboxy-protective group to be used in this reaction may include a conventional esterifying agent such as an alcohol or its reactive equivalent (e.g. halide, sulfonate, sulfate, diazo compound, etc.) or the like.

This reaction is usually carried out in the presence of a base as aforementioned in Process 3, in a conventional solvent which does not adversely influence the reaction such as ethyl acetate, dimethylsulfoxide, N,N-dimethylformamide, tetrahydrofuran or a mixture thereof.

The reaction temperature is not critical and the reaction is usually carried out under cooling, at ambient temperature or under warming.

Processes for the preparation of some of the compound (III) and the compound (IV) are explained as follows.

Process A

The compound (IIIa) or a salt thereof can be prepared by reacting a compound (V) or its reactive derivative at the amino group or a salt thereof with a compound (VI) or its reactive derivative at the carboxy group of a salt thereof.

Suitable salts of the compounds (V), (VI) and (IIIa) can be referred to the ones as exemplified for the compound (XVII).

Suitable reactive derivative at the amino group of the compound (V) and reactive derivative at the carboxy exemplified for the compounds (Ia) and (XVII), respectively.

This reaction can be carried out in a similar manner to that of aforementioned Process 1.

Process B

The compound (IIIc) or a salt thereof can be prepared by subjecting the compound (IIIb) or a salt thereof to the elimination reaction of the carboxy protective group.

Suitable salts or the compounds (IIIb) and (IIIc) can be referred to the ones as exemplified for the compound (XVII).

This reaction can be carried out in a similar manner to that of aforementioned Process 4.

Process C

The compound (VIIb) or a salt thereof can be prepared by introducing a carboxy protective group into the compound (VIIa) or a salt thereof.

Suitable salts of the compounds (VIIa) and (VIIb) can be referred to the ones as exemplified for the compound (XVII).

This reaction can be carried out in a similar manner to that of aforementioned Process 7.

Process D-1

The compound (IX) or a salt thereof can be prepared by reacting the compound (VII) or its reactive derivative at the amino group or a salt thereof with the compound (VIII) or its reactive derivative or a salt thereof.

Suitable salts of the compound (VII) can be referred to the ones as exemplified for the compound (XVII).

Switable salts of the compounds (VIII) and (IX) may include a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc; and the like.

Suitable reactive derivative of the amino group of the compound (VII) and reactive derivative of the compound (VIII) can be referred to the ones as exemplified for the compounds (Ia) and (XVII), respectively.

This reaction can be carried out in a similar manner to that of aforementioned Process 1.

Process D-2

The compound (X) or a salt thereof can be prepared by subjecting the compound (IX) or a salt thereof to the dehydrogenation reaction.

Suitable salt of the compound (X) can be referred to the ones as exemplified for the compound (IX).

The dehydrogenation method may include dehydrogenation by using a combination of an acid anhydride (e.g., acetic anhydride, trifluoroacetic anhydride, etc.) and dimethylsulfoxide, and the like.

This reaction is usually carried out in the presence of a base as aforementioned in Process 3, in a conventional solvent which does not adversely influence the reaction such as methylene chloride, dimethyl sulfoxide or the like.

The reaction temperature is not critical and the reaction is usually carried out under cooling.

Process 3

The compound (IIId) or a salt thereof can be prepared by subjecting the compound (X) or a salt thereof to conversion reaction of hydroxy to an acid residue.

Suitable salts of the compound (IIId) can be referred to the ones as exemplified for the compound (IX).

Suitable reagent for this reaction may be acid halide such as lower alkanesulfonyl halide (e.g. mesyl chloride, mesyl bromide, ethanesulfonyl chloride, ethanesulfonyl bromide, etc.), arenesulfonyl halide (e.g. benzenesulfonyl chloride, benzenesulfonyl bromide, tosyl chloride, tosyl bromide, etc.) etc.; thionyl halide (e.g. thionyl chloride, thionyl bromide, etc.); phosphorus trihalide (e.g., phosphorus trichloride, phosphorus tribromide, etc.); or the like.

This reaction is usually carried out in the presence of a base as mentioned in Process 3.

The reaction is usually carried out in a solvent such as N,N-dimethylformamide, tetrahydrofuran, or any other solvent which does not adversely affect the reaction.

The reaction temperature is not critical and the reaction is usually carried out under cooling or at ambient temperature.

Process E-1

The compound (XII) or a salt thereof can be prepared by reacting the compound (XI) or its reactive derivatvee at the amino group or a salt thereof with the compound (VIII) or its reactive derivative or a salt thereof.

Suitable salts of the compound (XI) can be referred to the ones as exemplified for the compound (XVII).

Suitable salts of the compound (XII) can be referred to the ones as exemplified for the compound (IX).

Suitable reactive derivative at the amino group of the compound (XI) can be referred to the ones as exemplified for the compound (Ia).

This reaction can be carried out in a similar manner to that of aforementioned Process 1.

Process E-2

The compound (X) or a salt thereof can be prepared by reacting the compound (XII) or a salt thereof with an oxidizing agent which is applicable to oxidative cleavage of carbon-carbon double bond. Suitable oxidizing agent may be ozone or a metal compound such as a manganese compound (e.g. potassium permanganate, sodium permanganate, etc.), an osmium compound (e.g. osmium tetroxide, etc.) and the like.

Suitable salts of the compound (X) can be referred to the ones as exemplified for the compound (IX).

In case that ozone is used as an oxidizing agent, it is necessary to treat the resultant compound (i.e. ozonide) with a boron compound (e.g. sodium borohydride, diboran, etc.) or di(lower)alkyl sulfide (e.g. dimethylsulfide, etc.).

The reaction is preferably conducted in a solvent such as lower alkanol (e.g. methanol, ethanol, propanol, butanol, pentanol, hexanol, etc.), chloroform, methylene chloride, acetone, tetrahydrofuran, benzene, diethyl ether, N,N-dimethylformamide, or any other solvent which does not adversely influence the reaction. The reaction temperature is not critical and the reaction can preferably be carried out under cooling.

Process F

The compound (XIIb) can be prepared by introducing a carboxy protective group into the compound (XIIa) or a salt thereof.

Suitable salts of the compound (XIIa) can be referred to the ones as exemplified for the compound (IX).

This reaction can be carried out in a similar manner to that of aforementioned Process 7.

Process G

The compound (XV) or a salt thereof can be prepared by reacting the compound (XIII) or a salt thereof with the compound (XIV) or a salt thereof.

When the compound (XIV) is used in free form in the reaction, the reaction is preferably carried out in the presence of a base such as alkali metal alkoxide (e.g., sodium methoxide, potassium methoxide, sodium ethoxide, potassium ethoxide, potassium t-butoxide, etc.), alkali metal hydroxide (e.g., sodium hydroxide, potassium hydroxide, etc.) or the like.

The reaction is usually carried out in a solvent such as water, tetrahydrofuran or any other solvent which does not adversely influence the reaction.

The reaction temperature is not critical and the reaction is usually carried out under cooling to warming.

Process H

The compound (XVIa) can be prepared by subjecting the compound (XVa) to dehydration.

The dehydrating agent to be used is this dehydration reaction may include phosphoryl chloride, thionyl chloride, phosphorus pentoxide, phosphorus pentachloride, phosphorus pentabromide and the like.

The present reaction is usually carried out in a solvent such as tetrahydrofuran, N,N-dimethylformamide or any other solvent which does not adversely affect the reaction.

The reaction temperature is not critical and the reaction is usually carried out under cooling at ambient temperature or under warming.

Process I

The compound (IV) or a salt thereof can be prepared by subjecting the compound (XVI) or a salt thereof to the elimination reaction of the mercapto-protective group.

The present elimination reaction may be carried out in accordance with a conventional method such as hydrolysis using an organic or inorganic acid (e.g. acetic acid, hydrobromic acid, etc.), hydrolysis using an organic or inorganic base (e.g. sodium methoxide, sodium ethoxide, etc.), alcoholysis using nitrate (e.g., silver nitrate, etc.) or the like.

The present reaction is usually carried out in a solvent such as water, alcohol (e.g., methanol, ethanol, etc.), tetrahydrofuran or a mixture thereof, or any other solvents which does not adversely affect the reaction.

The reaction temperature is not critical and the reaction is preferably carried out under cooling to heating.

The object compounds (I) and pharmaceutically acceptable salts thereof of the present invention are novel compounds which exhibit high antimicrobial activity and inhibit the growth of a wide variety of pathogenic microorganisms including Gram-positive and Gram-negative bacteria and are useful as antimicrobial agents. For therapeutic purpose, the compounds according to the present invention can be used in the form of conventional pharmaceutical preparation which contain said compounds, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives such as lactose, fumaric acid, citric acid, tartaric acid, stearic acid, maleic acid, succinic acid, malic acid, magnesium stearate, terra alba, sucrose, corn starch, talc, gelatin, agar, pectin, peanut oil, olive oil, cacao butter, ethylene glycol, and the like.

While the dosage of the compounds will vary depending upon the age and condition of the patient, an average single dose of about 10 mg, 50 mg, 100 mg, 250 mg, 500 mg, and 1000 mg of the compounds according to the present invention may be effective for treating infectious diseases caused by pathogenic bacteria. In general, amounts between 1 mg/body and about 6,000 mg/body or even more may be administered per day.

In order to illustrate the usefulness of the object compound, anti-microbial activities of representative compounds of the present invention are shown below.

Minimal inhibitory concentration (A) Test Method

In vitro antibacterial activity was determined by the two-fold agar-plate dilution method as described below.

One loopful of an overnight culture of each test strain in trypticase-soy broth ($10^8$ viable cells per ml) was streaked on heart infusion agar (HI-agar) containing graded concentrations of representative test compounds, and the minimal inhibitory concentration (MIC) was expressed in terms of $\mu g/ml$ after incubation at 37° C for 20 hours.

(B) Test Compounds (1) 7-[2-(2-Aminothiazol-4-yl)-2-methoxyiminoacetamido]-3-[(Z)-2-(1-methyl-3-pyridinio)-vinylthio]-3-cephem-4-carboxylate (syn isomer)

(2) 7-[2-(2-Aminothiazol-4-yl)-2-methoxyiminoacetamido]-3-[(Z)-2-(3-pyridyl)vinylthio]-3-cephem-4-carboxylic acid (syn isomer)

(3) 7-[2-Allyloxyimino-2-(5-amino-1,2,4-thiadiazol-3-yl)acetamido]-3-[(Z)-2-(3-pyridyl)vinylthio]-3-cephem-4-carboxylic acid (syn isomer)

(4) 7-[2-(2-Aminothiazol-4-yl)-2-ethoxyiminoacetamido]3-[(Z)-2-(1-methyl-3-piridinio)vinylthio]-3-cephem-4-carboxylate (syn isomer)

(C) Test Results

| | MIC ($\mu g/ml$) | | | |
| | Test compounds | | | |
| Test strain | (1) | (2) | (3) | (4) |
|---|---|---|---|---|
| Escherichia coli 31 | <0.025 | <0.025 | 0.05 | <0.025 |

The following preparations and examples are given for the purpose of illustrating the present invention in more detail.

Preparation 1

To an ice-cooled solution of propiolamide (1 g) in tetrahydrofuran (10 ml) and water (10 ml) was added a mixture of triphenylmethanethiol (4.2 g), tetrahydrofuran (10 ml) and 1N aqueous solution (1 ml) of sodium hydroxide at 0°–5° C. The mixture was stirred for 30 minutes at 0°–10° C. To the reaction mixture was added water (40 ml) and the mixture was cooled. The resultant precipitates were collected by filteration to give (Z)-3-tritylthioacrylamide (4.2 g).

IR (Nujol): 3380, 3180, 1640, 1570 cm$^{-1}$

Preparation 2

To an ice-cooled suspension of (Z)-3-tritylthioacrylamide (3.9 g) in N,N-dimethylformamide (40 ml) was added phosphorus pentachloride (3.65 g) and the mixture was stirred for 30 minutes at 20°. The reaction mixture was poured into ice-water and extracted with ethyl acetate. The separated organic layer was washed with brine, dried over magnesium sulfate and evaporated in vacuo to give (Z)-3-tritylthioacrylonitrile (2.85 g).

IR (Nujol): 2200 cm$^{-1}$

NMR (DMSO-$d_6$, $\delta$): 5.65 (1H, d, J=10 Hz), 6.88 (1H, d, J=10 Hz), 7—7.67 (15H, m)

Preparation 3

To a solution of triphenylmethanethiol (1.41 g) and 3-ethynylpyridine (0.5 g) in anhydrous tetrahydrofuran (10 ml) was added potassium t-butoxide (571 mg) at ambient temperature. The mixture was refluxed for 2 hours. After the reaction mixture was cooled to ambient temperature, the reaction mixture was poured into ice-water. The mixture was extracted with ethyl acetate. The extract was washed with a saturated aqueous solution of sodium chloride, dried over magnesium sulfate and concentrated in vacuo to give a crystal. The crystal was washed with ethanol and dried to give 3-[(Z)-2-(tritylthio)vinyl]pyridine (1.11 g).

mp: 140°–141° C.

IR (Nujol): 1590, 1560, 1470, 1450, 1410 cm$^{-1}$

NMR (CDCl$_3$, δ): 6.03 (1H, d, J=11 Hz), 6.27 (1H, d, J=11 Hz), 7.27 (15H, s), 7.13–7.23 (1H, m), 7.90 (1H, d, t, J=2, 8 Hz), 8.40 (1H, dd, J=2, 5 Hz), 8.63 (1H, d, J=2 Hz)

Preparation 4

The following compounds were obtained according to a similar manner to that of Preparation 3.

(1)

2-[(Z)-2-(Tritylthio)vinyl]pyridine

IR (Nujol): 1595, 1580, 1545, 1490, 1440, 1430 cm$^{-1}$

NMR (CDCl$_3$, δ) 6.30 (2H, s), 6.87–7.73 (18H, m), 8.63 (1H, dd, J=2 Hz, 5 Hz)

(2)

2-[(Z)-2-(Tritylthio)vinyl]thiophene

IR (Nujol): 1690, 1490, 1440, 1360 cm$^{-1}$

NMR (DMSO-d$_6$, δ): 5.80 (1H, d, J=11 Hz), 6.52 (1H, d, J=11 Hz), 6.80–7.60 (18H, m)

Preparation 5

To a solution of 3-[(Z)-2-(tritylthio)vinyl]pyridine (690 mg) in a mixture of tetrahydrofuran (3 ml), methanol (5 ml) and pyridine (0.147 ml) was dropwise added a solution of silver nitrate (371 mg) in methanol (20 ml) at ambient temperature. The reaction mixture was stirred at 40° C. in dark. The precipitate was collected, washed with methanol and dried over phosphorus pentoxide to give [(Z)-2-(3-pyridyl)vinylthio]silver (487 mg).

IR (Nujol): 1590, 1580, 1560, 1420 cm$^{-1}$

Preparation 6

The following compound was obtained according to a similar manner to that of Preparation 5. [(Z) -2-cyanovinylthio]silver IR (Nujol): 2200, 1530 cm$^{-1}$ Preparation 7

To a suspension of 2-[(Z)-2-(tritylthio)vinyl]-pyridine (14.5 g) in a mixture of tetrahydrofuran (80 ml) and methanol (90 ml) was added a solution of silver nitrate (7.79 g) in a mixture of water (20 ml) and methanol at ambient temperature. The mixture was stirred at 60° C. for 6 hours. The precipitate was collected, washed with methanol and tetrahydrofuran in turn and dried to give [(Z and E)-2-(2-pyridyl)vinylthio]silver (10.54 g).

IR (Nujol): 1590 cm$^{-1}$

Preparation 8

To a solution of benzhydryl 7-amino-3-mesyloxy-3cephem-4-carboxylate (6.91 g) and bis(trimethylsilyl)-urea (18.4 g) in methylene chloride (69 ml) was added 2-allyloxyimino-2-(5-amino-1,2,4-thiadiazol-3-yl)acetyl chloride hydrochloride (syn isomer) (4.08 g) at −10° C. under stirring and the mixture was stirred at the same temperature for 30 minutes. After the reaction mixture was added to a stirred mixture of water and methylene chloride, the solution was adjusted to pH 7.0 with a saturated aqueous solution of sodium bicarbonate. The separated organic layer was washed with brine, dried over magnesium sulfate and evaporated in vacuo to give benzhydryl 7-[2-allyloxyimino-2-(5-amino-1,2,4-thiadiazol-3-yl)acetamido]-3-mesyloxy-3-cephem-4-carboxylate (syn isomer) (8.90 g).

IR (Nujol): 1780, 1740, 1680, 1620 cm$^{-1}$

NMR (DMSO-d$_6$, δ): 3.17 (3H, s), 3.5–4.23 (2H, m), 4.65 (2H, d, J=5 Hz), 5.06–6.15 (5H, m), 6.90 (1H, s), 7.05–7.60 (10H, m), 8.12 (2H, broad s), 9.67 (1H, d, J=8 Hz)

Preparation 9

The following compounds were obtained according to a similar manner to that of Preparation 8.

(1) Benzhydryl 7-[2-(5-amino-1,2,4-thiadiazol-3-yl)-2-ehtoxyiminoacetamido]-3-mesyloxy-3-cephem-4-carboxylate (syn isomer)

IR (Nujol): 3300, 3150, 1770, 1725, 1660, 1600 cm$^{-1}$

NMR (DMSO-d$_6$, δ): 1.17 (3H, t, J=7 Hz), 3.4 and 3.9 (2H, ABq, J=16 Hz), 4.1 (2H, q, J=7 Hz), 5.23 (1H, d, J=5 Hz), 5.87 (1H, dd, J=8 Hz, 5 Hz), 6.82 (1H, s), 7.27 (10H, s), 9.53 (1H, d, J=8 Hz)

(2) Benzhydryl 7-[2-(5-amino-1,2,4-thiadiazol-3-yl)-2-methoxyiminoacetamido]-3-mesyloxy-3-cephem-4-carboxylate (syn isomer)

IR (Nujol): 1780, 1730, 1670, 1610, 1590, 1520 cm$^{-1}$

NMR (DMSO-d$_6$, δ): 3.16 (3H, s), 3.44–4.12 (2H, m), 3.92 (3H, s), 5.30 (1H, d, J=5 Hz), 5.92 (1H, dd, J=5, 8 Hz), 6.90 (1H, s), 7.04–7.60 (10H, m), 7.96–8.32 (2H, m), 9.64 (1H, d, J=8 Hz)

Preparation 10

A solution of dipheyldiazomethane (1.7 mol) in ethyl acetate (2.13 l) was added to a mixture of 7-amino-3-hydroxycepham-4-carboxylic acid (186 g) in dimethyl sulfoxide (1.5 l). The mixture was stirred at room temperature for 32 hours and filtered. To the filtrate was added water and the mixture was extracted with ethyl acetate. The extract was washed three times with water, dried over magnesium sulfate and filtered, and the filtrate was evaporated in vacuo. The residue was triturated with diisopropyl ether to give benzhydryl 7-amino-3-hydroxycepham-4-carboxylate (223 g) as powder.

IR (Nujol): 3350, 1750, 1720 cm$^{-1}$

NMR (DMSO-d$_6$, δ): 2.6–3.2 (2H, m), 3.8–4.3 (1H, m), 4.44 (1H, d, J=5 Hz), 4.65 (1H, d, J=6 Hz), 5.0 (1H, d, J=5 Hz), 6.0 (1H, d, J=4 Hz), 6.83 (1H, s), 7.37 (10H, s)

Preparation 11

Formic acid (0.4 ml) and acetic anhydride (1 ml) were stirred at 40° C. for 30 minutes. The reaction mixture was cooled in an ice-water bath and added dropwise to a mixture of benzhydryl 7-amino-3-hydroxycepham-4-carboxylate (1.0 g) in methylene chloride (30 ml) at 3° C.. The mixture was stirred at 3° C. for 10 minutes and adjusted to pH 7.0 with 5% aqueous solution of sodium bicarbonate, washed with water, dried over magnesium sulfate and evaporated in vacuo. The residue was triturated with diisopropyl ether to give benzhydryl 7-formamido-3-hydroxycepham-4-carboxylate (1.05 g) as powder.

IR (Nujol): 3450, 3300, 1770, 1730, 1665 cm$^{-1}$

NMR (DMSO-d$_6$, δ): 2.6–3.2 (2H, m), 3.8–4.3 (1H, m), 4.7 (1H, d, J=6 Hz), 5.11 (1H, d, J=4 Hz), 5.47 (1H, dd, J=9 Hz, 4 Hz), 6.05 (1H, d, J=4 Hz), 6.83 (1H, s), 7.37 (10H, s), 8.08 (1H, s), 8.93 (1H, d, J=9 Hz)

Preparation 12

A solution of trifluoroacetic anhydride (2.12 ml) in methylene chloride (5 ml) was added dropwise to a solution of dimethyl sulfoxide (1.56 g) in methylene chloride (10 ml) at −50° C. The mixture was stirred at −50° C. for 10 minutes. To the mixture was added a solution of benzhydryl 7-formamido-3-hydroxycepham-4-carboxylate (4.12 g) in methylene chloride (10 ml) and dimethylsulfoxide (1 ml). The mixture was stirred at −50° C. for 30 minutes and triethylamine (4 ml) was added dropwise thereto at −50° C. The reaction mixture was allowed to warm up to ambient temperature, poured into ice-water and extracted with methylene chloride. The extract was washed three times with water, dried over magnesium sulfate and filtered, and the filtrate was evaporated in vacuo. The residue was triturated with diisopropyl ether to give benzhydryl 7-formamido-3-hydroxy-3-cephem-4-carboxylate (3.42 g) as powder.

IR (Nujol): 3300, 1760, 1660 cm$^{-1}$

NMR (DMSO-d$_6$, δ): 2.9–4.9 (2H, m), 5.23 (1H, d, J=5 Hz), 5.61 (1H, dd, J=9 Hz, 5 Hz), 6.9 (1H, s), 7.37 (10H, s), 8.22 (1H, s), 9.18 (1H, d, J=9 Hz)

Preparation 13

Mesyl chloride (0.66 ml) and potassium carbonate (1.38 g) were added to a solution of benzhydryl 7-formamido-3-hydroxy-3-cephem-4-carboxylate (2.05 g) in N,N-dimethylformamide (6 ml) at −30° C. The mixture was stirred at −30°°C. for 30 minutes. Mesyl chloride (0.4 ml) was added to the mixture. The reaction mixture was stirred at −30°C for 20 minutes, poured into ice-water and extracted with ethyl acetate. The extract was washed with water, dried over magnesium sulfate and filtered, and the filtrate was evaporated in vacuo. The residue was dissolved in a small amount of ethyl acetate and the mixture was subjected to column chromatography on silica gel and eluted with a mixture of benzene and ethyl acetate (1:1). The eluent was evaporated in vacuo. The residue was triturated with diisopropyl ether to give benzhydryl 7-formamido-3-mesyloxy-3-cephem-4-carboxylate (0.85 g).

IR (Nujol): 3290, 1790, 1720, 1665 cm$^{-1}$

NMR (DMSO-d$_6$, δ): 3.2 (3H, s), 3.72 (1H, d, J=18 Hz), 4.1 (1H, d, J=18 Hz), 5.31 (1H, d, J=5 Hz), 5.9 (1H, dd, J=9 Hz, 5 Hz), 6.92 (1H, s), 7.38 (10H, s), 8.17 (1H, s), 9.14 (1H, d, J=9 Hz)

Preparation 14

A mixture of formic acid (1 l) and acetic anhydride (2.5 l) was stirred at 50° C. for 1 hour and cooled at 40°C. To the mixture were added 7-amino-3-methylenecepham-4-carboxylic acid (1,070 g) and N,N-dimethylformamide (500 ml). The mixture was stirred for 1 hour at 55° C. and cooled in an ice-water bath. A resultant precipitate was collected by filtration and washed with a small amount of a mixture of ethyl acetate and diisopropyl ether (1:1) to give 7-formamido-3-methylenecepham-4-carboxylic acid (1.02 g).

IR (Nujol): 3360, 2500, 1770, 1730, 1610 cm$^{-1}$

NMR (DMSO-d$_6$, δ): 3.38 (1H, d, J=13.4 Hz), 3.60 (1H, d, J=13.4 Hz), 5.07 (1H, s), 5.27 (1H, d, J=4.6 Hz), 5.27 (2H, s), 5.51 (1H, dd, J=8.4 Hz, 4.6 Hz), 8.1 (1H, s), 8.96 (1H, d, J=8.4 Hz)

Preparation 15

7-Formamido-3-methylenecepham-4-carboxylic acid (1.570 g) was added to a solution (0.93M, 8.36 l) of diphenyldiazomethane in ethyl acetate by portions. The mixture was stirred at 45° C. for 1 hour and evaporated in vacuo. The residue was triturated with diisopropyl ether to give benzhydryl 7-formamido-3-methylenecepham-4-carboxylate (2.337 g).

IR (Nujol): 3360, 1765, 1725, 1660 cm$^{-1}$

NMR (DMSO-d$_6$, δ): 3.46 (2H, s), 5.32 (1H, dd, j=9 Hz, 4 Hz), 5.47 (2H, s), 5.65 (1H, J=4 Hz), 6.85 (1H, s), 7.32 (10H, s), 8.11 (1H, s), 9.0 (1H, d, J=9 Hz)

Preparation 16

A solution of benzhydryl 7-formamido-3-methylenecepham-4-carboxylate (40.8 g) in methylene chloride (300 ml) and methanol (1.2 l) was cooled at −74° C. in a dry ice-acetone bath. A theoretical amount of ozone was blown through the solution at −74° C. for 10 minutes with stirring, and nitrogen gas was blown through the solution at −74° C. for 10 minutes. Dimethyl sulfide (20 ml) was added to the solution at −74° C. The mixture was slowly warmed to ambient temperature and evaporated in vacuo. The residue was subjected to column chromatography on silica gel and eluted with ethyl acetate. The eluent was evaporated in vacuo to give benzhydryl 7-formamido-3-hydroxy-3-cephem-4-carboxylate (34.4 g).

IR (Nujol): 3300, 1760, 1660 cm$^{-1}$

NMR (DMSO-d$_6$, δ): 2.94–4.9 (2H, m), 5.23 (1H, d, J=5 Hz), 5.61 (1H, dd, J=9 Hz, 5 Hz), 6.9 (1H, s), 7.37 (10H, s), 8.22 (1H, s), 9.18 (1H, d, J=9 Hz)

Preparation 17

To a solution of phosphorus pentachloride (57 g) in methylene chloride (1 l) was added to pyridine (22 ml) at −20° C. and the mixture was stirred for 30 minutes at −20° C. p-Nitrobenzyl 7-(2-phenylacetamido)-3-mesyloxy-3-cephem-4-carboxylate (50 g) was added to the solution at 5° C. and stirred at the same temperature for 1 hour. Methanol (56 ml) was added to the solution at −30° C. and stirred at −15° C. for 30 minutes. To the solution were added pyridine (80 ml) and diisopropylethylamine (31.4 ml) at −30° C. 2-(5-Amino-1,2,4-thiadiazol-3-yl)-2-ethoxyiminoacetyl chloride hrydrochloride (syn isomer) (26.7 g) was added to the solution at −30° C. by portions and stirred at −15° C. for 1 hour. Water (1 l) was added to the solution and stirred for 30 minutes. A resultant precipitate was collected by filtration and washed with diisopropyl ether and air-dried to give p-nitrobenzyl 7-[2-(5-amino-1,2,4-thiadiazol-3-yl)-2-ethoxyiminoacetamido]-3-mesyloxy-3-cephem-4-carboxylate (syn isomer) (40 g).

NMR (DMSO-d$_6$, δ):1.25 (3H, t, J=7 Hz), 3.47 (3H, s), 3.50–4.33 (2H, m), 4.23 (2H, g, J=7 Hz), 5.27–5.62 (2H, s), 5.98 (1H, dd, J=7 Hz), 5.27–5.62 (1H, m), 5.42 (2H, s), 5.98 (1H, dd, J=8 Hz, J=5 Hz), 8.0–8.33 (2H, m), 9.65 (1H, d, J=8 Hz)

Preparation 18 p-Nitrobenzyl 7-[2-(5-amino-1,2,4-thidiazol-3-yl)-2-ethoxyiminoacetamido]-3-mesyloxy-3-cephem-4-carboxylate (syn isomer) (40 g) was dissolved in a mixed solution of acetic acid (4.8 ml), methanol (200 ml) and tetrahydrofuran (1200 ml). After adding 10% palladium on carbon (30 g) to the solution, the mixture was subjected to catalytic reduction at room temperature under atmospheric pressure.

The catalyst was filtered off and washed with a mixture of tetrahydrofuran and methanol. The filtrate and washing were combined and concentrated in vacuo.

The concentrated solution was adjusted to pH 7.0 with an aqueous solution of sodium bicarbonate and evaporated in vacuo. To the residue was added ethyl acetate. An insoluble material was filtered off. The filtrate was washed with ethyl acetate. The seperated aqueous layer was concentrated in vacuo and adjusted to pH 2.5 with hydrochloric acid. A resultant precipitate was collected by filtration and washed with water and dried over phosphorus pentoxide to give 7-[2-(5-amino-1,2,4-thiadiazol-3-yl)-2-ethoxyiminoacetamido]-3-mesyloxy-3-cephem-4-carboxylic acid (syn isomer) (17.5 g).

NMR (DSMO-d$_6$, δ): 1.27 (3H, t, J=7 Hz), 3.40 (3H, s), 3.81 (2H, dd, J=18 Hz, 10 Hz), 4.20 (2H, q, J=7 Hz), 5.2 (1H, d, J=5 Hz), 5.83 (1H, dd, J=5 Hz, 8 Hz), 8.20 (2H, s), 9.60 (1H, d, J=8 Hz)

EXAMPLE 1

Vilsmeier reagent was prepared from N,N-dimethylformamide (1.26 g) and phosphorus oxychloride (2.64 g) in ethyl acetate (26.5 ml) in a usual manner. 2-(2-Formamidothiazol-4-yl) -2-methoxyiminoacetic acid (syn isomer) (3.29 g) was added to the stirred suspension of Vilsmeier reagent under ice-cooling and the mixture was stirred for 30 minutes at the same temperature to give an activated acid solution. To a solution of benzhydryl 7-amino-3-[(Z)-2-(3-pyridyl)vinylthio]-3-cephem-4-carboxylate (6 g) and bis(trimethylsilyl)urea (9.78 g) in tetrahydrofuran (60 ml) was added the activated solution obtained above at −30°, and the mixture was stirred at −20° to −10° C. for 30 minutes. Water and ethyl acetate were added to the resultant solution under stirring and the separated organic layer was washed with a saturated aqueous solution of sodium bicarbonate and brine, dried over magnesium sulfate. The organic solution was evaporated in vacuo to give a residue. The residue was subjected to column chromatography on silica gel and eluted with a mixture of ethyl acetate and methylene chloride (1:1). The fractions containing the object compound were combined and evaporated in vacuo to give benzhydryl 7-[2-(2-formamidothiazol-4-yl)-2-methoxyiminoacetamido]-3-[(Z)-2-(3-pyridyl)-vinylthio]-3-cephem-4-carboxylate (syn isomer) (3.09 g).

IR (Nujol): 3250, 1770, 1705, 1680, 1650 cm$^{-1}$

NMR (DSMO-d$_6$, δ): 3.6-4.3 (2H, m), 3.90 (3H, s), 5.30 (1H, d, J=5 Hz), 5.92 (1H, dd, J=8 Hz, 5 Hz), 6.67 (1H, d, J=12 Hz), 6.87 (1H, d, J=12 Hz), 6.92 (1H, s), 7.2-7.6 (12H, m), 7.65-8.65 (3H, m), 8.50 (1H, s), 9.73 (1H, d, J=8 Hz)

EXAMPLE 2

To a solution of phosphorus petachloride (455 mg) in methylene chloride (15 ml) was added 2-(5-amino-1,2,4-thiadiazol-3-yl)-2-(2-cyclopenten-1-yl) oxyiminoacetic acid (syn isomer) (557 mg) at −20°C. The mixture was stirred at −21~−10° C. for 30 minutes. The resultant mixture was added to a solution of benzhydryl 7-amino-3-[(Z)-2-(3-pyridyl)vinylthio]-3-cephem-4-carboxylate (1 g) and bis(trimethylsilyl)urea (2 g) in methylene chloride (20 ml) at −20° C. The mixture was stirred at −20~−10° C. for 30 minutes. The mixture was concentrated in vacuo and the residue was dissolved in a mixture of water (100 ml), sodium bicarbonate (920 mg), ethyl acetate and tetrahydrofuran. The organic layer was separated, washed with water and a saturated aqueous solution of sodium chloride in turn, dried over magnesium sulfate, concentrated in vacuo, and the residue was triturated with diethyl ether to give benzhydryl 7-[2-(5-amino-1,2,4-thiadiazol-3-yl)-2-(2-cyclopenten-1-yl-oxyiminoacetamido]-3-[(Z)-2-(3-pyridyl)vinylthio]-3-cehem-4-carboxylate (syn isomer) (1.12 g).

IR (Nujol): 3300, 3150, 1780, 1675, 1610, 1530, 1280, 1220 cm$^{-1}$

NMR (DMSO-d$_6$, δ): 1.8-2.6 (4H, m), 3.70 and 4.11 (2H, ABq, J=18 Hz), 5.1-5.5 (1H, m), 5.22 (1H, d, J=5 Hz), 5.7-6.2 (3H, m), 6.77 (2H, s), 6.92 (1H, s), 7.1-7.6 (1H, m), 7.6-7.9 (1H, m), 8.1 (2H, broad s), 8.3-8.7 (2H, m), 9.57 (1H, d, J=8 Hz)

EXAMPLE 3

To a solution of benzhydryl 7-amino-3-[(Z)-2-(3-pyridyl)vinylthio]-3-cephem-4-carboxylate (3 g) and bis(trimethylsilyl)urea (3.70 g) in tetrahydrofuran (45 ml) was added 2-(5-amino-1,2,4-thiadiazol-3yl)-2-carboxymethoxyiminoacetic methanesulfonic anhydride (syn isomer) (1.45 g) at −30° C. The mixture was stirred at −20~−10° C. for 1 hour, at 0° C. overnight and at ambient temperature for 2 days. The mixture was poured into a mixture of ethyl acetate and a saturated aqueous solution of sodium chloride. The organic layer was separated, dried over sodium sulfate and concentrated in vacuo to give a precipitate. The precipitate was collected and washed with ethyl acetate and diisopropyl ether in turn to give benzhydryl 7-[2-(5-amino-1,2,4-thiadiazol-3yl)-2-carboxymethoxyiminoacetamido]-3-[(Z)-2-(3-pyridyl)vinylthio]-3-cephem-4-carboxylate (syn isomer) (1.95 g).

IR (Nujol): 1770, 1730, 1670, 1610, 1520 cm$^{-1}$

NMR (DMSO-d$_6$, δ): 3.73, 4.13 (2H, ABq, J=18 Hz), 4.73 (2H, broad s), 5.30 (1H,d, J=5 Hz), 5.97 (1H, dd, J=5 Hz, J=8 Hz), 6.80 (2H, broad s), 6.93 (1H, s), 7.13-7.67 (11H, m), 7.67-7.93 (1H, m), 8.07-8.33 (2H, m), 8.43-8.70 (2H, m), 9.67 (1H, d, J=8 Hz)

EXAMPLE 4

To a suspension of D-N-(4-ethyl-2,3-dioxo-1-piperazinylcarbonoyl)-2-(4-hydroxyphenyl)glycine (2 g) in methylene cloride (12 ml) was added trimethylchlorosilane (1.59 ml) at room temperature, to the mixture was added triethylamine (1.67 ml) under ice-cooling and the mixture was stirred at 15°~20° C. for 1 hour. To the above mixture were added N,N-dimethylformamide (0.47 ml) and trichloromethyl chloroformate (0.39 ml) at −20° C. and the mixture was stirred for 2 hours at −10°~15° C. To the mixture was added a suspension of benzhydryl 7-amino-3-[(Z)-2-(3-pyridyl)vinylthio]-3-cephem-4-carboxylate (3 g) and bis(trimethylsilyl) urea (4.9 g) in methylene chloride (30 ml) at −15°~−10° C. and the mixture was stirred for 30 minutes under ice-cooling. Water and ethyl acetate were successively added to the resultant reaction mixture under stirring, and the separated organic layer was washed with a saturated aqueous solution of sodium bicarbonate and brine, dried over magnesium sulfate and evaporated in vacuo to give a residue. The residue was purified by column chromatography on silica gel to give benzhydryl 7-[D-N-(4-ethyl-2,3-dioxo-1-piperazinylcarbonyl) -2-(4-hydroxyphenyl)-glycinamido]-3-[(Z)-2-(3-pyridyl)vinylthio]-3-cephem-4-carboxylate (1.7 g).

IR (Nujol): 3250, 1780, 1705, 1670, 1605 cm$^{-1}$

NMR (DMSO-d$_6$, δ): 1.0 (3H, t, J=7 Hz), 3.16-3.67 (4H, m), 3.67-4.07 (4H, m), 5.1 (1H, d, J=5 Hz), 5.47 (1H, d, J=8 Hz), 5.8 (1H, dd, J=8 Hz, 5 Hz), 6.6 (1H, d, J=10 Hz), 6.71 (2H, d, J=8 Hz), 6.8 (1H, d, J=10

Hz), 6.89 (1H, s), 7–7.6 (16H, m), 9.37 (1H, d, J=8 Hz), 9.7 (1H, d, J=8 Hz)

EXAMPLE 5

A mixture of benzhydryl 7-amino-3-[(Z)-2-(2-pyridyl)-vinylthio]-3-cephem-4-carboxylate (600 ml) and bis-(trimethylsilyl)urea (981 mg) in methylene chloride (6 ml) was stirred at 30°~35° C. for 30 minutes to give a clear solution. To the clear solution was added 2-allyloxyimino-2-(5-amino-1,2,4-thiadiazol-3yl) acetyl chloride monohydrochloride (syn isomer) (480 mg) at −20° C. and the mixture was stirred for 30 minutes at −10°~−15° C. The mixture was poured into a mixture of chloroform and water. The organic layer was separated and concentrated in vacuo to give a residue. The residue was dissolved in a mixture of tetrahydrofuran, ethyl acetate and dilute aqueous solution of sodium bicarbonate. The organic layer was separated, washed with dilute aqueous solution of sodium bicarbonate and a saturated aqueous solution of sodium chloride in turn, dried over magnesium sulfate and concentrated in vacuo, and the residue was triturated with diisopropyl ether to give benzhydryl 7-[2-allyloxyimino-2-(5-amino-1,2,4-thiadiazol-3-yl) -acetamido]-3-[(Z)-2-(2-pyridyl)-vinylthio]-3-cephem-4-carboxylate (syn isomer) (848 mg).

IR (Nujol): 1780, 1680, 1620, 1600, 1530 cm$^{-1}$

NMR (DMSO-d$_6$, δ): 3.76, 4.12 (2H, ABq, J=18 Hz), 4.68 (2H, d, J=4 Hz), 5.12–5.48 (3H, m), 5.76–6.24 (2H, m), 6.68 (1H, d, J=11 Hz), 6.88 (1H, d, J=11 Hz), 6.92 (1H, s), 7.00–7.56 (12H, m), 7.68–8.40 (3H, m), 8.60 (1H, d, J=4 Hz), 9.64 (1H, d, J=8 Hz)

EXAMPLE 6

The following compounds were obtained according to similar manners to those of Examples 1–5.

(1) Benzhydryl 7-[2-(2-formamidothiazol-4-yl)-2-methoxyiminoacetamido]-3-[(Z)-2-(1-methyl-3-pyridinio)vinylthio]-3-cephem-4-carboxylate iodide (syn isomer)

IR (Nujol): 1775, 1720, 1640, 1540 cm$^{-1}$ (2) Benzhydryl 7-[2-(2-aminothiazol-4yl)-2-methoxyiminoacetamido]-3-[(Z)-2-(3-pyridyl)-vinylthio]-3-cephem-4-carboxylate (syn isomer)

IR (Nujol): 1775, 1720, 1670, 1605, 1530 cm$^{-1}$ (3) 7-[2-(2-Aminothiazol-4-yl)-2-methoxyiminoacetamido]-3-[(Z)-2-(3-pyridyl)vinylthio]-3-cephem-4- carboxylic acid (syn isomer)

IR (Nujol): 3300, 1770, 1660, 1610, 1530 cm$^{-1}$ (4) Benzhydryl 7-[2-(2-aminothiazol-4yl)-2-methoxyiminoacetamido]-3-[(Z)-2-(1-methyl-3-pyridinio)vinylthio]-3-cephem-4-carboxylate iodide (syn isomer)

IR (Nujol): 1770, 1710, 1660, 1620 cm$^{-1}$ (5) 7-[2-(2-Aminothiazol-4-yl)-2methoxyiminoacetamido]-3-[(Z)-2-(1-methyl-3-pyridinio)vinylthio]-3-cephem-4carboxylate (syn isomer)

IR (Nujol): 3300, 1765, 1660, 1605, 1530 cm$^{-1}$ (6) Benzhydryl 7-[2-allyloxyimino-2-(5-amino-1,2,4-thiadiazol-3-yl)acetamido]-3-[(Z)-2-(3-pyridyl) -vinylthio]-3-cephem-4-carboxylate (syn isomer)

IR (Nujol): 1760, 1730, 1660, 1605 cm$^{-1}$ (7) 7-[2-Allyloxyimino-2-(5-amino-1,2,4-thiadiazol-3-yl) acetamido]-3-[(Z)-2-(3-pyridyl)vinylthio]-3-cephem-4-carboxylic acid (syn isomer)

IR (Nujol): 1770, 1670, 1610, 1530 cm$^{-1}$ (8) Benzhydryl 7-[2-allyloxyimino-2-(5-amino-1,2,4-thiadiazol-3yl)acetamido]-3-[(Z)-2-(1-methyl-3-pyridinio)vinylthio(3-cephem-4-carboxylate iodide (syn isomer)

IR (Nujol): 1775, 1720, 1650, 1600 cm$^{-1}$ (9) 7-[2-Allyloxyimino-2-(5-amino-1,2,4-thiadiazol-3-yl) acetamido]-3-[benzhydryl(Z)-2-(1-methyl-3-pyridinio) vinyl thio]-3-cephem-4-carboxylate (syn isomer)

IR (Nujol): 3300, 1765, 1670, 1610 cm$^{-1}$

(10) 7-[2-(5-Amino-1,2,4-thiadiazol-3-yl)-2-ethoxyiminoacetamido]-3-[benzhydryl (Z)-2-(3-pyridyl)vingylthio]-3-cephem-4-carboxylic acid (syn isomer)

mp: 171° C. (dec.)

IR (Nujol): 3300, 3250, 1770, 1670, 1610 cm$^{-1}$

(11) Benzhydryl 7-[2-(5-amino-1,2,4-thiadiazol-3-yl)-2-ethoxyiminoacetamido]-3-[(Z)-2-(3-pyridyl)vinylthio]-3-cephem-4-carboxylate (syn isomer)

IR (Nujol): 3350, 3150, 1780, 1730, 1675, 1615 cm$^{-1}$

(12) Benzhydryl 7-[2-(5-amino-1,2,4-thiadiazol-3-yl)-2-methoxyiminoacetamido]-3-[(Z)-2-(3-pyridyl)vinylthio]-3-cephem-4-carboxylate (syn isomer)

IR (Nujol): 1770, 1670, 1610, 1520 cm$^{-1}$

(13) 7-[2-(5-Amino-1,2,4-thiadiazol-3-yl)-2-methoxyiminoacetamido]-3-[(Z)-2-(3-pyridyl)-vinylthio]-3-cephem-4-carboxylic acid (syn isomer)

mp: 164° C. (dec.)

IR (Nujol): 1770, 1670, 1530 cm$^{-1}$

(14) Benzhydryl 7-[2-(2-formamidothiazol-4-yl)-2-(2-propynyloxyimino)acetamido]-3-[(Z)-2-(3-pyridyl)-vinylthio]-3-cephem-4-carboxylate (syn isomer)

IR (Nujol): 1780, 1680, 1550, 1280, 1225 cm$^{-1}$

NMR (DMSO-d$_6$, δ): 3.5 (1H, m), 3.74 and 4.15 (2H, q, J=18 Hz), 4.8 (2H, m), 5.32 (1H, d, J=5 Hz), 5.94 (1H, dd, J=5 Hz and 8 Hz), 6.79 (2H, s), 6.94 (1H, s), 7.1–7.6 (15H, m), 7.6–7.9 (1H, m), 8.4–8.7 (2H, m), 8.55 (1H, s), 9.87 (1H, d, J=8 Hz)

(15) Benzhydryl 7-[2-allyloxyimino-2-(2-formamidothiazol-4-yl)acetamido]-3-[(Z)-2-(3-pyridyl)vinylthio]-3-cephem-4-carboxylate (syn isomer)

IR (Nujol): 1780, 1690, 1670, 1550, 1280, 1220 cm$^{-1}$

NMR (DMSO-d$_6$, δ): 4.15 and 3.75 (2H, ABq, J=8 Hz), 4.6–4.8 (2H, m), 5.0–5.6 (2H, m), 5.32 (1H, d, J=5 Hz), 5.7–6.3 (2H, m), 6.80 (2H, s), 6.95 (1H, s), 7.2–7.6 (12H, m), 7.6–8.0 (1H, m), 8.4–8.8 (2H, m), 8.55 (1H, s), 9.78 (1H, d, J=8 Hz), 12.6 (1H, s)

(16) Benzhydryl 7-[2-benzhydryloxycarbonylmethoxyimino-2-(2-formamidothiazol-4-yl)acetamido]-3-[(Z)-2(3-pyridyl)vinylthio]-3-cephem-4-carboxylate (syn isomer)

IR (Nujol): 1780, 1730, 1680, 1540 cm$^{-1}$

NMR (DMSO-d$_6$, δ): 3.75 and 4.18 (2H, ABq, J=18 Hz), 4.97 (2H, broad s), 5.33 (1H, d, J=5 Hz), 5.93 (1H, dd, J=8 Hz, 5 Hz), 6.73 (1H, d, J=10 Hz), 6.9 (1H, d, J=10 Hz), 6.93 (1H, s), 6.97 (1H, s), 7.12–8.67 (25H, m), 8.57 (1H, s), 9.83 (1H, d, J=8 Hz)

(17) Benzhydryl 7-[2-ethoxyimino-2-(2-formamidothiazol-4-yl)acetamido]-3-[(Z)-2-(3-pyridyl)vinylthio]-3-cephem-4-carboxylate (syn isomer)

IR (Nujol): 1780, 1680, 1540 cm$^{-1}$

NMR (DMSO-d$_6$, δ): 1.27 (3H, t, J=7 Hz), 3.6–4.3 (2H, m), 4.17 (2H, q, J=7 Hz), 5.3 (1H, d, J=5 Hz), 5.95 (1H, dd, J=8 Hz, 5 Hz), 6.7 (1H, d, J=10 Hz), 6.85 (1H, d, J=10 Hz), 6.9 (1H, s), 7.1–8.67 (15H, m), 8.52 (1H, s), 9.73 (1H, d, J=8 Hz)

(18) Benzhydryl 7-[2-allyloxyimino-2-(5-amino-1,2,4-thiadiazol-3-yl)acetamido]-3-[(E)-2-(2-pyridyl)-vinylthio]-3-cephem-4-carboxylate (syn isomer)

IR (Nujol): 1775, 1675, 1610, 1520 cm$^{-1}$

NMR (DMSO-d$_6$, δ): 3.50–4.37 (2H, m), 4.67 (2H, d, J=5 Hz), 5.07–5.53 (3H, m), 5.67–6.27 (2H, m), 6.77 (1H, d, J=15 Hz), 6.90 (1H, s), 7.13–7.73 (13H, m), 7.77–8.40 (3H, m), 8.50–8.76 (1H, m), 9.70 (1H, d, J=9 Hz)

(19) Benzhydryl 7-[2-allyloxyimino-2-(5-amino-1,2,4-thiadiazol-3-yl)acetamido]-3-[(Z)-2-cyanovinylthio]-3-cephem-4-carboxylate (syn isomer)

IR (Nujol): 3300, 2210, 1780, 1675, 1610 cm$^{-1}$

NMR (DMSO-d$_6$, δ): 3.7 (2H, broad s), 4.69 (2H, d, J=5 Hz), 5.1–6.12 (4H, m), 5.27 (1H, d, J=5 Hz), 5.9 (1H, d, J=10 Hz), 6.95 (1H, s), 7.2–7.67 (10H, m), 7.78 (1H, d, J=10 Hz), 9.67 (1H, d, J=8 Hz)

(20) Benzhydryl 7-[2-benzhydryloxycarbonylmethooxyimino-2-(2-formamidothiazol-4-yl)acetamido]-3-[(Z)-2-(1-methyl-3-pyridinio)vinylthio]-3-cephem-4-carboxylate iodide (syn isomer)

IR (Nujol): 3350, 1760, 1735, 1660 cm$^{-1}$

NMR (DMSO-d$_6$, δ): 3.59 and 4.2 (2H, d, J=18 Hz), 4.33 (3H, s), 4.92 (1H, broad s), 5.33 (1H, d, J=5 Hz), 5.97 (1H, dd, J=8 Hz, 5 Hz), 6.68 (1H, d, J=10 Hz), 6.9 (2H, s), 7 (1H, d, J=10 Hz), 7.12–9(25H, m), 8.5 (1H, s), 9.8 (1H, d, J=8 Hz)

(21) Benzhydryl 7-[2-ethoxyimino-2-(2-formamidothiazol-4-yl)acetamido]-3-[(Z)-2-(1-methyl-3-pyridinio)-vinylthio]-3-cephem-4-carboxylate iodide (syn isomer)

IR (Nujol): 1780, 1720, 1650 cm$^{-1}$

(22) Benzhydryl 7-[2-(2-aminothiazol-4-yl)-2-(2-propynyloxyimino)acetamido]-3-[(Z)-2-(3-pyridyl)vinylthio] -3-cephem-4-carboxylate (syn isomer)

IR (Nujol): 1770, 1670, 1530, 1270, 1215 cm$^{-1}$

NMR (DMSO-d$_6$, δ): 3.5 (1H, m), 3.77 and 4.1 (2H, ABq, J=18 Hz), 4.7 (2H, m), 5.31 (1H, d, J=5 Hz), 5.90 (1H, dd, J=5 Hz and 8 Hz), 6.82 (2H, s), 6.86 (1H, s), 6.97 (1H, s), 7.1–7.6 (11H, m), 7.6–7.9 (1H, m), 8.4–8.7 (2H, m), 9.76 (1H, d, J=8 Hz)

(23) Benzhydryl 7-[2-allyloxyimino-2-(2-aminothiazol-4-yl)acetamido]-3-[(Z)-2(3-pyridyl)vinylthio]-3-cephem-4-carboxylate (syn isomer)

IR (Nujol):·3300, 1780, 1670, 1610, 1535, 1280, 1220 cm$^{-1}$

(24) Benzhydryl 7-[2-(2-aminothiazol-4-yl)-2-benzhydryloxycarbonylmethoxyiminoacetamido]-3-[(Z)-2-(1-methyl-3-pyridinio)vinylthio]-3-cephem-4-carboxylate iodide (syn isomer)

NMR (DMSO-d$_6$, δ): 3.6–4.2 (2H, m), 4.3 (3H, s), 4.9 (2H, s), 5.28 (1H, d, J=5 Hz), 5.9 (1H, dd, J=8 Hz, 5 Hz), 6.75 (1H, d, J=10 Hz), 6.87 (3H, s), 7.03 (1H, d, J=10 Hz), 6.87 (24H, m), 9.83 (1H, d, J=8 Hz)

(25) Benzhydryl 7-[2-(2-aminothiazol-4-yl)-2-ethoxyimino -acetamido]-3-[(Z)-2-(3-pyridyl)vinylthio]-3-cephem-4-carboxylate (syn isomer)

IR (Nujol): 1780, 1720, 1675 cm$^{-1}$

(26) Benzhydryl 7-[2-(2-aminothiazol-4-yl)-2-ethoxyimino -acetamido]-3-[(Z)-2-(1-methyl-3-pyridinio)-vinylthio]- 3-cephem-4-carboxylate iodide (syn isomer)

IR (Nujol): 1770, 1670, 1625 cm$^{-1}$

(27) 7-[2-(5-Amino-1,2,4-thiadiazol-3-yl)-2-carboxy -methoxyiminoacetamido]-3-[(Z)-2-(3-pyridyl)vinylthio]-3-cephem-4-carboxylic acid (syn isomer)

mp: 178° C. (dec.)

IR (Nujol): 1770, 1675, 1620, 1520 cm$^{-1}$

(28) 7-[2-(2-Aminothiazol-4-yl)-2-(2-propynyloxyimino) -acetamido]-3-[(Z)-2-(3-pyridyl)vinylthio]-3-cephem-4-carboxylic acid (syn isomer)

IR (Nujol): 3200, 1770, 1670, 1190 cm$^{-1}$

(29) 7-[2-Allyloxyimino-2-(2-aminothiazol-4-yl) acetamido]-3-[(Z)-2-(3-pyridyl)vinylthio]-3-cephem-4-carboxylic acid (syn isomer)

IR (Nujol): 1770, 1670, 1530 cm$^{-1}$

(30) 7-[2-Allyloxyimino-2-(5-amino-1,2,4-thiadiazol-3-yl) acetamido]-3-[(Z)-2-(2-pyridyl)vinylthio]-3-cephem-4-carboxylic acid (syn isomer)

mp: 168° C. (dec.)

IR (Nujol): 1780, 1670, 1620, 1530 cm$^{-1}$

(31) 7-[2-Allyloxyimino-2-(5-amino-1,2,4-thiadiazol-3-yl) acetamido]-3-[(E)-2-(2-pyridyl)vinylthio]-3-cephem-4-carboxylic acid (syn isomer)

mp: 160° C. (dec.)

IR (Nujol): 1770, 1670, 1615, 1580, 1530 cm$^{-1}$

(32) 7-[2-(2-Aminothiazol-4-yl)-2-ethoxyiminoacetamido]-3-[(Z)-2-(3-pyridyl)vinylthio]-3-cephem-4-carboxylic acid (syn isomer)

IR (Nujol): 3250, 1770, 1660 cm$^{-1}$

(33) 7-[2-(2-Aminothiazol-4-yl)-2-ethoxyiminoacetamido]-3-[(Z)-2-(1-methyl-3-pyridinio)vinylthio]-3-cephem-4-carboxylate (syn isomer)

IR (Nujol): 3300, 1760, 1650, 1600 cm$^{-1}$

(34) 7-[2-Allyloxyimino-2-(5-amino-1,2,4-thiadiazol-3-yl) -acetamido]-3-[(Z)-2-cyanovinylthio]-3-cephem-4-carboxylic acid (syn isomer)

IR (Nujol): 3300, 2210, 1760, 1660, 1610 cm$^{-1}$

(35) 7-[D-N-(4-Ethyl-2,3-dioxo-1-piperazinylcarbonyl)-2-(4-hydroxyphenyl)glycinamido]-3-[(Z)-2-(3-pyridyl) -vinylthio]-3-cephem-4-carboxylic acid IR (Nujol): 3200, 1770, 1710, 1675, 1605 cm$^{-1}$

(36) 7-[2-(2-Aminothiazol-4-yl)-2-carboxymethoxyiminoacetamido ]-3-[(Z)-2-(1-methyl-3-pyridinio)-vinylthio]-3-cephem-4-carboxylate (syn isomer)

mp: 188° C. (dec.)

IR (Nujol): 3300, 1765, 1670, 1600 cm$^{-1}$

(37) 7-[2-(5-Amino-1,2,4-thiadiazol-3-yl)-2-ethoxyiminoacetamido ]-3-[(Z)-2-phenylvinylthio]-3-cephem-4-carboxylic acid (syn isomer)

mp: 165° C. (dec.)

IR (Nujol): 3275, 3175, 1770, 1680, 1670, 1540, 1520, 1400 cm$^{-1}$

(38) Benzhydryl 7-formamido-3-[(Z)-2-(2-pyridyl)-vinylthio]-3-cephem-4-carboxylate IR (Nujol): 1770, 1690–1660, 1590, 1580 cm$^{-1}$

(39) Benzhydryl 7-formamido-3-[(E)-2-(2-pyridyl) vinylthio]-3-cephem-4-carboxylate IR (Nujol): 1780, 1690, 1660, 1600, 1580 cm$^{-1}$

(40) Benzhydryl 7-formamido-3-[(Z)-2-cyanovinylthio]-3-cephem-4-carboxylate

IR (Nujol): 3300, 2210, 1780, 1730, 1680 cm$^{-1}$

(41) Benzhydryl 7-formamido-3-[(Z)-2-(3-pyridyl)-vinylthio]-3-cephem-4-carboxylate IR (Nujol): 1785, 1705, 1690, 1560, 1220 cm$^{-1}$

(42) 7-[2-(5-Amino-1,2,4-thiadiazol-3-yl)-2-hydroxyiminoacetamido ]-3-[(Z)-2-(3-pyridyl)vinylthio]-3-cephem-4-carboxylic acid (syn isomer)

mp: 178°–182° C. (dec.)

IR (Nujol): 3300, 3150, 1770, 1670, 1610, 1530 cm$^{-1}$

(43) 7-[2-(2-Cyclopenten-1-yl)oxyimino-2-(2-formamidothiazol -4-yl)acetamido]-3-[(Z)-2-(3-pyridyl) -vinylthio]-3-cephem-4-carboxylic acid (syn isomer)

IR (Nujol): 3250, 1765, 1650, 1610 cm$^{-1}$

NMR (DMSO-d$_6$, δ): 1.60–2.47 (4H, m), 3.70–4.20 (2H, m), 5.13–5.47 (2H, m), 5.60–6.50 (3H, m), 6.92 (2H, dd, J=11 Hz, 4 Hz), 7.35 (1H, s), 7.67–9.0 (5H, m), 9.58 (1H, d, J=8 Hz)

(44) Benzhydryl 7-[2-(2-formamidothiazol-4-yl)-2-propoxyiminoacetamido]-3-[(Z)-2-(3-pyridyl)vinylthio]-3-cephem-4-carboxylate (syn isomer)

NMR (DMSO-d$_6$, δ): 0.95 (3H, t, J=7 Hz), 1.35–2.0 (2H, m), 3.73–4.37 (4H, m), 5.28 (1H, d, J=4 Hz), 5.90 (1H, dd, J=4 Hz, 8 Hz), 6.67–6.87 (2H, m), 6.92 (1 H, s), 7.0–7.63 (12H, m) 7.63–8.83 (3H, m), 8.5 (1H, s), 9.68 (1H, d, J=8 Hz)

(45) Benzhydryl 7-[2-(5-amino-1,2,4-thiadiazol-3-yl)-2-cyclopentyloxyiminoacetamido]-3-[(Z)-2-(3-pyridyl)-vinylthio]-3-cephem-4-carboxylate (syn isomer)

NMR (DMSO-d$_6$, δ): 1.27–2.07 (8H, m), 3.73–4.17 (2H, m), 4.53–4.90 (1H, m), 5.23 (1H, d, J=5 Hz), 5.9

(1H, dd, J=5 Hz, 9 Hz), 6.50–7.05 (2H, m), 6.90 (1H, s), 7.05–7.90 (13H, m), 7.90–8.80 (3H, m), 8.08 (1H, s), 9.57 (1H, d, J=9 Hz)

(46) Benzhydryl 7-[2-(5-amino-1,2,4-thiadiazol-3-yl)-2-(2-propynyloxyimino)acetamido]-3-[(Z)-2-(3-pyridyl)-vinylthio]-3-cephem-4-carboxylate (syn isomer)

NMR (DMSO-d$_6$, δ): 3.50–4.05 (2H, m), 3.31 (1H, s), 5.31 (1H, d, J=4 Hz), 5.97 (1H, dd, J=5 Hz, 8 Hz), 6.79 (2H, dd, J=4 Hz, 10 Hz), 6.96 (1H, s), 7.03–7.64 (1H, m), 7.62–7.99 (1H, m), 7.97–8.58 (2H, m), 8.56–8.75 (2H, m), 9.79 (1H, d, J=8 Hz)

(47) Benzhydryl 7-[2-(5-amino-1,2,4-thiadiazol-3-yl)-2-methoxyiminoacetamido]-3-[(Z)-2(1-methyl-3-pyridinio)vinylthio]-3-cephem-4-carboxylate iodide (syn isomer)

NMR (DMSO-d$_6$, δ): 3.90 (3H, s), 4.03 (3H, s), 3.57–4.27 (2H, m), 5.25 (1H, d, J=5 Hz), 5.92 (1H, dd, J32 5 Hz, 9 Hz), 6.75 (1H, d, J=11 Hz), 6.87 (1H, s), 7.07–7.62 (11H, m), 7.93–9.06 (6H, m), 9.58 (1H, d, J=9 Hz)

(48) 7-[2-(2-Aminothiazol-4-yl)-2-(2-cyclopenten-1-yl)-oxyiminoacetamido]-3-[(Z)-2-(3-pyridyl)vinylthio]-3-cephem-4-carboxylic acid (syn isomer)

MNR (DMSO-d$_6$, δ): 1.86–2.57 (4H, m), 3.66 and 4.15 (2H, ABq, J=18 Hz), 5.13–5.40 (2H, m), 5.60–6.23 (3H, m), 6.50 (1H, s), 6.66 (1H, d, J=11 Hz), 6.87 (1H, d, J=11 Hz), 7.33–8.83 (4H, m), 9.53 (1H, d, J=8 Hz)

(49) Benzhydryl 7-[2-(2-aminothiazol-4-yl)-2-propoxyiminoacetamido]-3-[(Z)-2-(3-pyridyl)vinylthio]-3-cephem-4-carboxylate (syn isomer)

NMR (DMSO-d$_6$, δ): 0.95 (3H, t, J=7 Hz), 1.35–2.0 (2H, m), 3.73–4.37 (4H, m), 5.28 (1H, d, J=4 Hz), 5.9 (1H, dd, J=4 Hz, 8 Hz), 6.67–6.87 (2H, m), 6.92 (1H, s), 7.0–7.63 (12H, m), 7.63–8.82 (3H, m), 9.68 (1H, d, J=8 Hz)

(50) 7-[2-(5-Amino-1,2,4-thiadiazol-3-yl)-2-methoxyiminoacetamido ]-3-[(Z)-2-(1-methyl-3-pyridinio)-vinylthio]-3-cephem-4-carboxylate (syn isomer)

IR (Nujol): 3260, 1765, 1660, 1610 cm$^{-1}$

(51) 7-[2-(5-Amino-1,2,4-thiadiazol-3-yl)-2-ethoxyiminoacetamido]-3-[(Z)-2-(1-methyl-3-pyridinio)vinylthio]-3-cephem-4-carboxylate (syn isomer)

IR (Nujol): 3300, 1770, 1670, 1610 cm$^{-1}$

NMR (DMSO-d$_6$, δ): 1.25 (3H, t, J=7 Hz), 3.0–3.93 (2H, m), 4.20 (2H, q, J=7 Hz), 4.36 (3H, s), 5.05 (1H, d, J=5 Hz), 5.50 (1H, dd, J=5 Hz, 8 Hz), 6.65 (1H, d, J=10 Hz), 7.04 (1H, d, J=10 Hz), 7.80–9.30 (4H, m), 8.17 (2H, s), 9.40 (1H, d, J=8 Hz)

(52) 7-[2-(2-Aminothiazol-4-yl)-2-propoxyiminoacetamido]-3-[(Z)-2-(3-pyridyl)vinylthio]-3-cephem-4-carboxylic acid (syn isomer)

IR (Nujol): 3280, 3180, 1775, 1665 cm$^{-1}$

NMR (DMSO-d$_6$, δ): 0.90 (3H, t, J=7 Hz), 1.66–2.0 (2H, m), 3.43–4.43 (4H, m), 5.19 (1H, d, J=5 Hz), 5.79 (1H, dd, J=5 Hz, 9 Hz), 6.48–6.95 (3H, m), 7.24–8.85 (6H, m), 9.60 (1H, d, J=9 Hz)

(53) 7-[2-(5-Amino-1,2,4-thiadiazol-3-yl)-2-cyclopenthyloxyiminoacetamido]-3-[(Z)-2-(3-pyridyl)vinylthio]-3-cephem-4-carboxylic acid (syn isomer)

IR (Nujol): 3270, 1770, 1670, 1615 cm$^{-1}$

NMR (DMSO-d$_6$, δ): 1.33–2.33 (8H, m), 3.50–4.27 (2H, m), 5.23 (1H, d, J=5 Hz), 5.90 (1H, dd, J=5 Hz, 9 Hz), 6.53–7.00 (2H, m), 7.27–8.83 (4H, m), 8.02 (1H, s), 9.57 (1H, d, J=9 Hz)

(54) 7-[2-(5-Amino-1,2,4-thiadiazol-3-yl)-2-(2-propynyloxyimino) acetamido]-3-[(Z)-2-(3-pyridyl)-vinylthio]-3-cephem-4-carboxylic acid (syn isomer)

IR (Nujol): 3270, 1770, 1670, 1615 cm$^{-1}$

NMR (DMSO-d$_6$, δ): 3.52 (1H, m), 3.66–4.08 (2H, m), 4.82 (2H, d, J=2 Hz), 5.19 (1H, d, J=4 Hz), 5.81 (1H, dd, J=4 Hz, 10 Hz), 6.92 (2H, dd, J=4 Hz, 10 Hz), 7.17–8.92 (6H, m), 9.15 (1H, d, J=10 Hz)

(55) 1-Acetoxyethyl 7-[2-(2-aminothiazol-4-yl)-2-allyloxyiminoacetamido]-3-[(Z)-2-(3-pyridyl)vinylthio]-3-cephem-4-carboxylate (syn isomer)

IR (Nujol): 3300, 1760–1780, 1670, 1240, 1210, 1070 cm$^{-1}$

EXAMPLE 7

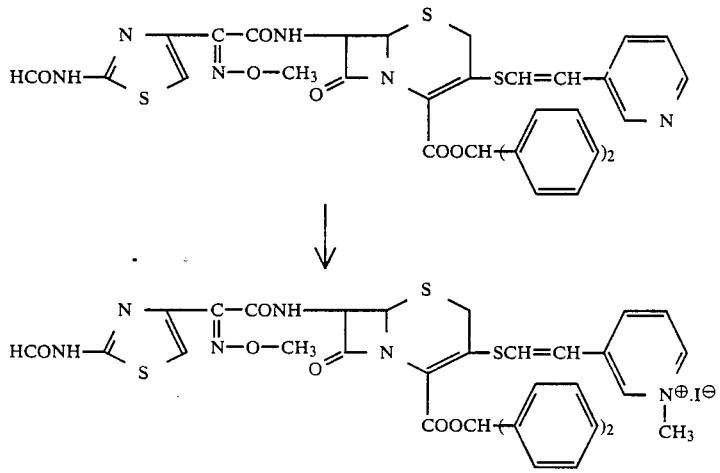

To a solution of benzhydryl 7-[2-(2-formamidothiazol-4-yl)-2-methoxyiminoacetamido]-3-[(Z)-2-(3-pyridyl)vinylthio]-3-cephem-4-carboxylate (syn isomer) (2 g) in N,N-dimethylformamide (10 ml) was added methyl iodide (2 ml) at ambient temperature and the mixture was stirred at the same temperature for hours. The reaction mixture was evaporated in vacuo to give benzhydryl 7-[2-(2-formamidothiazol-4-yl)-2-methoxyiminoacetamido]-3-[(Z)-2-(1-methyl-3-pyridinio)vinylthio]-3-cephem-4-carboxylate iodide (syn isomer) (2.4 g).

IR (Nujol): 1775, 1720, 1640, 1540 cm$^{-1}$

NMR (DMSO-d$_6$, δ): 3.55–4.16 (2H, m), 3.92 (3H, s), 4.35 (3H, s), 5.33 (1H, d, J=5 Hz), 5.97 (1H, dd, J=8 Hz, 5 Hz), 6.78 (1H, d, J=11 Hz), 6.92 (1H, s), 7.2 (1H, d, J=11 Hz), 7.17–7.67 (11H, m), 7.97–9.03 (4H, m), 8.53 (1H, s), 9.75 (1H, d, J=8 Hz)

EXAMPLE 8

To a solution of benzhydryl 7-[2-allyloxyimino-2-(5-amino-1,2,4-thiadiazol-3-yl) acetamido]-3-[(Z)-2-(3-pyridyl)vinylthio]-3-cephem-4-carboxylate (syn isomer) (2.3 g) in N,N-dimethylformamide (12 ml) was added methyl iodide (2.3 ml) at ambient temperature and the mixture was stirred at the same temperature for 3 hours. The reaction mixture was evaporated in vacuo to give benzhydryl 7-[2-allyloxyimino-2-(5-amino-1,2,4-thiadiazol-3-yl)acetamido]-3-[(Z)-2-(1-methyl-3-pyridinio)vinylthio]-3-cephem-4-carboxylate iodide (syn isomer) (2.71 g).

IR (Nujol): 1775, 1720, 1650, 1600 cm$^{-1}$

NMR (DMSO-d$_6$, δ): 3.67–4.20 (2H, m), 4.35 (3H, s), 4.70 (2H, d, J=5 Hz), 4.7–6.2 (5H, m), 6.8 (1H, d, J=11 Hz), 6.9 (1H, s), 7.2 (1H, d, J=11 Hz), 7.12–7.6 (10H, m), 7.9–9.05 (4H, m), 9.67 (1H, d, J=8 Hz)

EXAMPLE 9

The following compounds were obtained according to similar manners to those of Examples 7 and 8.

(1) Benzhydryl 7-[2-(2-aminothiazol-4-yl)-2-methoxyiminoacetamido ]-3-[(Z)-2-(1-methyl-3-pyridinio)-vinylthio]-3-cephem-4-carboxylate iodide (syn isomer)

IR (Nujol): 1770, 1710, 1660, 1620 cm$^{-1}$ (2) 7-[2-(2-Aminothiazol-4-yl)-2-methoxyiminoacetamido]-3-[(Z)-2(1-methyl-3-pyridinio)vinylthio]-3-cephem-4-carboxylate (syn isomer)

IR (Nujol): 3300, 1765, 1660, 1605, 1530 cm$^{-1}$ (3) 7-[2-Allyloxyimino-2-(5-amino-1,2,4-thiadiazol-3-yl) acetamido]-3-[(Z)-2-(1-methyl-3-pyridinio)vinylthio]-3-cephem-4-carboxylate (syn isomer)

IR (Nujol): 3300, 1765, 1670, 1610 cm$^{-1}$ (4) Benzhydryl 7-[2-benzhydryloxycarbonylmethoxyimino-2-(2-formamidothiazol-4-yl)acetamdio]-3-[(Z)-2-(1-methyl-3-pyridinio)vinylthio]-3-cephem-4-carboxylate iodide (syn isomer)

IR (Nujol): 3350, 1760, 1735, 1660 cm$^{-1}$

NMR (DMSO-d$_6$, δ): 3.59 and 4.2 (2H, d, J=18 Hz), 4.33 (3H, s), 4.92 (1H, broad s), 5.33 (1H, d, J=5 Hz), 5.97 (1H, dd, J=8 Hz, 5 Hz), 6.68 (1H, d, J=10 Hz), 6.9 (2H, s), 7 (1H, d, J=10 Hz), 7.12–9 (25H, m), 8.5 (1H, s), 9.8 (1H, d, J=8 Hz)

(5) Benzhydryl 7-[2-ethoxyimino-2-(2-formamidothiazol-4-yl)acetamido]-3-[(Z)-2-(1-methyl-3-pyridinio)-vinylthio]-3-cephem-4-carboxylate iodide (syn isomer)

IR (Nujol): 1780, 1720, 1650 cm$^{-1}$

NMR (DMSO-d$_6$, δ): 1.3 (3H, t, J=7 Hz), 3.6–4.3 (2H, m), 4.2 (2H, q, J=7 Hz), 4.37 (3H, s), 5.37 (1H, d, J=5 Hz), 6.0 (1H, dd, J=8 Hz, 5 Hz), 6.82 (1H, d, J=10 Hz), 6.93 (1H, s), 7.05 (1H, d, J=10 Hz), 7.1–9.05 (15H, m), 8.55 (1H, s), 9.75 (1H, d, J=8 Hz)

(6) Benzhydryl 7-[2-(2-aminothiazol-4-yl)-2-benzhydryloxycarbonylmethoxyiminoacetamido]-3-[(Z)-2-(1-methyl-3-pyridinio)vinylthio]-3-cephem-4-carboxylate iodide (syn isomer)

NMR (DMSO-d$_6$, δ): 3.6–4.2 (2H, m) 4.3 (3H, s), 4.9 (2H, s), 5.28 (1H, d, J=5 Hz), 5.9 (1H, dd, J=8 Hz, 5 Hz), 6.75 (1H, d, J=10 Hz), 6.87 (3H, s), 7.03 (1H, d, J=10 Hz), 7–9.05 (24H, m), 9.83 (1H, d, J=8 Hz)

(7) Benzhydryl 7-[2-(2-aminothiazol-4-yl)-2-ethoxyiminoacetamido]-3-[(Z)-2-(1-methyl-3-pyridinio) vinylthio]-3-cephem-4-carboxylate iodide (syn isomer)

IR (Nujol): 1770, 1670, 1625 cm$^{-1}$ (8) 7-[2-(2-Aminothiazol-4-yl)-2-ethoxyiminoacetamido]- 3-[(Z)-2-(1-methyl-3-pyridinio)-vinylthio]-3-cephem-4-carboxylate (syn isomer)

IR (Nujol): 3300, 1760, 1650, 1600 cm$^{-1}$ (9) 7-[2-(2-Aminothiazol-4-yl)-2-carboxymethoxyiminoacetamido ]-3-[(Z)-2-(1-methyl-3-pyridinio)-vinylthio]-3-cephem-4-carboxylate (syn isomer)

IR (Nujol): 3300, 1765, 1670, 1600 cm$^{-1}$

(10) Benzhydryl 7-[2-(5-amino-1,2,4-thiadiazol-3-yl)-2-methoxyiminoacetamido]-3-[(Z)-2-(1-methyl-3-pyridinio)vinylthio]-3-cephem-4-carboxylate iodide (syn isomer)

NMR (DMSO-d$_6$, δ): 3.90 (3H, s), 4.03 (3H, s), 3.57–4.27 (2H, m), 5.25 (1H, d, J=5 Hz), 5.92 (1H, dd, J=5 Hz, 9 Hz), 6.75 (1H, d, J=11 Hz), 6.87 (1H, s), 7.07–7.62 (11H, m), 7.93–9.06 (6H, m), 9.58 (1H, d, J=9 Hz)

(11) 7-[2-(5-Amino-1,2,4-thiadiazol-3-yl)-2-methoxyiminoacetamido]-3-[(Z)-2-(1-methyl-3-pyridinio)vinylthio]-3-cephem-4-carboxylate (syn isomer)

IR (Nujol): 3260, 1765, 1660, 1610 cm$^{-1}$

(12) 7-[2-(5-Amino-1,2,4-thiadiazol-3-yl)-2-ethoxyiminoacetamido]-3-[(Z)-2-(1-methyl-3-pyridinio)vinylthio]-3-cephem-4-carboxylate (syn isomer)

IR (Nujol): 3300, 1770, 1670, 1610 cm$^{-1}$

EXAMPLE 10

To a suspension of benzhydryl 7-[2-(2-formamidothiazol-4yl)-2-methoxyiminoacetamido-3-[(Z)-2-(1-methyl-3-pyridinio) vinylthio]-3-cephem-4-carboxylate iodide (syn isomer) (2.35 g) in methanol (12 ml) was added conc. hydrochloric acid (0.61 ml) at ambient temperature and the mixture was stirred at the same temperature for 4 hours. To the reaction mixture were added water, tetrahydrofuran and ethyl acetate. The mixture was adjusted to pH 7 with a saturated aqueous solution of sodium bicarbonate. The separated organic layer was washed with brine and dried over magnesium sulfate. The organic solution was evaporated in vacuo to give benzhydryl 7-[2-(2aminothiazol-4-yl)-2-methoxyiminoacetamido]-3-[(Z)-2-(1-methyl-3-pyridinio)vinylthio]-3-cephem-4-carboxylate iodide (syn isomer) (2.2 g).

IR (Nujol): 1770, 1710, 1660, 1620 cm$^{-1}$

NMR (DMSO-d$_6$, δ): 3.5–4.2 (2H, m), 3.93 (3H, s), 4.33 (3H, s), 5.32 (1H, d, J=5 Hz), 5.9 (1H, dd, J=8 Hz, 5 Hz), 6.83 (1H, d, J=11 Hz), 6.92 (1H, s), 6.95 (1H, s), 7.23 (1H, d, J=11 Hz), 7.02–7.67 (10H, m), 7.97–9.1 (4H, m), 9.87 (1H, d, J=8 Hz)

EXAMPLE 11

To a solution of benzhydryl 7-[2-(2-formamidothiazol-4-yl)-2-methoxyiminoacetamido]-3-[(Z)-2-(3-pyridyl)-vinylthio]-3-cephem-4-carboxylate (syn isomer) (1 g) in a mixture of methanol (10 ml) and tetrahydrofuran (5 ml) was added conc. hydrochloric acid (0.31 ml) at ambient temperature and the mixture was stirred at the same temperature for 4 hours. To the reaction mixture were added water and ethyl acetate and the mixture was adjusted to pH 7 with a saturated aqueous solution of sodium bicarbonate. The separated organic layer was washed with brine, dried over magnesium sulfate and evaporated in vacuo to give benzhydryl 7-[2-(2-aminothiazol-4-yl)-2-methoxyiminoacetamido]-3-[(Z)-2-(3-pyridyl)vinylthio]-3-cephem-4-carboxylate (syn isomer) (0.86 g).

IR (Nujol): 1775. 1720, 1670, 1605, 1530 cm$^{-1}$

NMR (DMSO-d$_6$, δ): 3.68 and 4.18 (2H, ABq, J=18 Hz), 3.88 (3H, s), 5.24 (1H, d, J=4 Hz), 5.88 (1 Hz, dd, J=8 Hz, 4 Hz), 6.75 (1H, d, J=12 Hz), 6.8 (1H, s), 6.85 (1H, d, J=12 Hz), 6.95 (1H, s), 7.05–7.6 (11H, m), 7.7–8.4 (3H, m), 9.65 (1H, d, J=8 Hz)

EXAMPLE 12

The following compounds were obtained according to similar manners to those of Examples 10 and 11.

(1) 7-[2-(2-Aminothiazol-4-yl)-2-methoxyiminoacetamido]-3-[(Z)-2-(3-pyridyl)vinylthio]-3-cephem-4-carboxylic acid (syn isomer)
IR (Nujol): 3300, 1770, 1660, 1610, 1530 cm$^{-1}$ (2) 7-[2-(2-Aminothiazol-4-yl)-2-methoxyiminoacetamido]-3-[(Z)-2-(1-methyl-3-pyridinio)vinylthio]-3-cephem-4-carboxylate (syn isomer)
IR (Nujol): 3300, 1765, 1660, 1605, 1530 cm$^{-1}$ (3) Benzhydryl 7-[2-allyloxyimino-2-(5-amino-1,2,4-thiadiazol-3-yl) acetamido]-3-[(Z)-2-(3-pyridyl)vinylthio]-3-cephem-4-carboxylate (syn isomer)
IR (Nujol): 1760, 1730, 1660, 1605 cm$^{-1}$ (4) 7-[2-Allyloxyimino-2-(5-amino-1,2,4-thiadiazol-3-yl) acetamido]-3-[(Z)-2-(3-pyridyl)vinylthio]-3-cephem-4-carboxylic acid (syn isomer)
IR (Nujol): 1770, 1670, 1610, 1530 cm$^{-1}$ (5) Benzhydryl 7-[2-allyloxyimino-2-(5-amino-1,2,4-thiadiazol-3-yl)acetamido]-3-[(Z)-2-(1-methyl-3-pyridinio)vinylthio]-3-cephem-4-carboxylate iodide (syn isomer)
IR (Nujol): 1775, 1720, 1650, 1600 cm$^{-1}$ (6) 7-[2-Allyloxyimino-2-(5-amino-1,2,4-thiadiazol-3-yl)acetamido]-3-[(Z)-2-(1-methyl-3-pyridinio) vinylthio]-3-cephem-4-carboxylate (syn isomer)
IR (Nujol): 3300, 1765, 1670, 1610 cm$^{-1}$ (7) 7-[2-(5-Amino-1,2,4-thiadiazol-3-yl)-2-ethoxyiminoacetamido ]-3-[(Z)-2-(3-pyridyl)vinylthio]-3-cephem-4-carboxylic acid (syn isomer)
mp 171° C. (dec.)
IR (Nujol): 3300, 3250, 1770, 1670, 1610 cm$^{-1}$ (8) Benzhydryl 7-[2-(5-amino-1,2,4-thiadiazol-3-yl)-2-ethoxyiminoacetamido]-3-[(Z)-2-(3-pyridyl)vinylthio]-3-cephem-4-carboxylate (syn isomer)
IR (Nujol): 3350, 3150, 1780, 1730, 1675, 1615 cm$^{-1}$ (9) Benzhydryl 7-[2-(5-aminio-1,2,4-thiadiazol-3-yl)-2-methoxyiminoacetamido]-3-[(Z)-2-(3-pyridyl)vinylthio]-3-cephem-4-carboxylate (syn isomer)
IR (Nujol): 1770, 1670, 1610, 1520 cm$^{-1}$

(10) 7-[2-(5-Amino-1,2,4-thiadiazol-3-yl)-2-methoxyiminoacetamido]-3-[(Z)-2-(3-pyridyl) vinylthio]-3-cephem-4-carboxylate acid (syn isomer)
mp: 164° C. (dec.)
IR (Nujol): 1770, 1670, 1530 cm$^{-1}$

(11) Benzhydryl 7-[2-(5-amino-1,2,4-thiadiazol-3-yl)-2-(2-cyclopenten-1-yl)oxyiminoacetamido]-3-[(Z)-2-(3-pyridyl)vinylthio]-3-cephem-4-carboxylate (syn isomer)
IR (Nujol): 3300, 3150, 1780, 1675, 1610, 1530, 1280, 1220

(12) Benzhydryl 7-[2-(5-amino-1,2,4-thiadiazol-3-yl)-2-carboxymethoxyiminoacetamido]-3-[(Z)-2-(3-pyridyl)vinylthio]-3-cephem-4-carboxylate (syn isomer)
IR (Nujol): 1770, 1730, 1670, 1610, 1520 cm$^{-1}$

(13) Benzhydryl 7-[2-allyloxyimino-2-(5-amino-1,2,4-thiadiazol-3-yl)acetamido]-3-[(E)-2-(2-pyridyl)vinylthio]-3-cephem-4-carboxylate (syn isomer)
IR (Nujol): 1775, 1675, 1610, 1520 cm$^{-1}$

(14) Benzhydryl 7-[2-allyloxyimino-2-(5-amino-1,2,4-thiadiazol-3-yl)acetamido]-3-[(Z)-2-(2-pyridyl)vinylthio]-3-cephem-4-carboxylate (syn isomer)
IR (Nujol): 1780, 1680, 1620, 1600, 1530 cm$^{-1}$

(15) Benzhydryl 7-[2-allyloxyimino-2-(5-amino-1,2,4-thiadiazol-3-yl)acetamido]-3-[(Z)-2-cyanovinylthio]-3-cephem-4-carboxylate (syn isomer)
IR (Nujol): 3300, 2210, 1780, 1675, 1610 cm$^{-1}$

(16) Benzhydryl 7-[2-(2-aminohiazol-4-yl)-2-(2-propynyloxyimino)acetamido]-3-[(Z)-2-(3-pyridyl)-vinylthio]-3-cephem-4-carboxylate (syn isomer)
IR (Nujol): 1770, 1670, 1530, 1270, 1215 cm$^{-1}$
NMR (DMSO-d$_6$, δ): 3.5 (1H, m), 3.77 and 4.1 (2H, ABq, J=18 Hz), 4.7 (2H, m), 5.31 (1H, d, J=5 Hz), 5.90 (1H, dd, J=5 Hz and 8 Hz), 6.82 (2H, s), 6.86 (1H, s), 6.97 (1H, s), 7.1–7.6 (11H, m), 7.6–7.9 (1H, m), 8.4–8.7 (2H, m), 9.76 (1H, d, J=8 Hz)

(17) Benzhydryl 7-[2-allyloxyimino-2-(2-aminothiazol-4-yl)acetamido]-3-[(Z)-2-(3-pyridyl)vinylthio]-3-cephem-4-carboxylate (syn isomer)
IR (Nujol): 3300, 1780, 1670, 1610, 1535, 1280, 1220 cm$^{-1}$
NMR (DMSO-d$_6$, δ): 3.79 and 4.11 (2H, ABq, J=18 Hz), 4.62 (2H, d, J=5 Hz), 5.0–5.5 (2H, m), 5.31 (1H, d, J=5 Hz), 5.7–6.2 (2H, m), 6.81 (2H, s), 7.96 (1H, s), 7.0–7.6 (12H, m), 7.6–7.9 (1H, m), 8.3–8.7 (2H, m), 9.64 (1H, d, J=8 Hz)

(18) Benzhydryl 7-[2-(2-aminothiazol-4-yl)-2-Benzhydryloxycarbonylmethoxyiminoacetamido]-3-[(Z)-2-(1-methyl-3-pyridinio)vinylthio]-3-cephem-4-carboxylate iodide (syn isomer)
NMR (DMSO-d$_6$, δ): 3.6–4.2 (2H, m), 4.3 (3H, s), 4.9 (2H, s), 5.28 (1H, d, J=5 Hz), 5.9 (1H, dd, J=8 Hz, 5 Hz), 6.75 (1H, d, J=10 Hz), 6.87 (3H, s), 7.03 (1H, d, J=10 Hz), 7–9.05 (24H, m), 9.83 (1H, d, J=8 Hz)

(19) Benzhydryl 7-[2-(2-aminothiazol-4-yl)-2-ethoxyiminoacetamido ]-3-[(Z)-2-(3-pyridyl)vinylthio]-3-cephem- 4-carboxylate (syn isomer)
IR (Nujol): 1780, 1720, 1675 cm$^{-1}$
NMR (DMSO-d$_6$, δ): 1.27 (3H, t, J=7 Hz), 3.63–4.33 (2H, m), 4.17 (2H, q, J=7 Hz), 5.31 (1 H, d, J=5 Hz), 5.95 (1H, dd, J=8 Hz, 5 Hz), 6.7 (1H, d, J=11 Hz), 6.8 (1H, s), 6.9 (1H, d, J=11 Hz), 6.97 (1H, s), 7.12–8.67 (14H, m), 9.68 (1H, d, J=8 Hz)

(20) Benzhydryl 7-[2-(2-aminothiazol-4-yl)-2-ethoxyiminoacetamido]-3-[(Z)-2-(1-methyl-3-pyridinio)vinylthio]-3-cephem-4-carboxylate iodide (syn isomer)
IR (Nujol): 1770, 1670, 1625 cm$^{-1}$
NMR (DMSO-d$_6$, δ): 1.3 (3H, t, J=7 Hz), 3.7–4.4 (2H, m), 4.25 (2H, q, J=7 Hz), 4.4 (3H, s), 5.38 (1H, d, J=5 Hz), 5.95 (1H, dd, J=8 Hz, 5 Hz), 6.85 (1H, d, J=10 Hz), 6.97 (1H, s), 7 (1H, s) 7.1 (1H, d, J=10 Hz), 7.1–9.13 (14H, m), 9.9 (1H, d, J=8 Hz)

(21) 7-[2-(5-Amino-1,2,4-thiadiazol-3-yl)-2-carboxymethoxyiminoacetamido]-3-[(Z)-2-(3-pyridyl)vinylthio]-3-cephem-4-carboxylic acid (syn isomer)
mp: 178° C. (dec.)
IR (Nujol): 1770, 1675, 1620, 1520 cm$^{-1}$

(22) 7-[2-(2-Aminothiazol-4-yl)-2-(2-propynyloxyimino)acetamido]-3-[(Z)-2-(3-pyridyl)vinylthio]-3-cephem-4-carboxylic acid (syn isomer)
IR (Nujol): 3200, 1770, 1670, 1190 cm$^{-1}$

(23) 7-[2-Allyloxyimino-2-(2-aminothiazol-4-yl) acetamido]-3-[(Z)-2-(3-pyridyl)vinylthio]-3-cephem-4-carboxylic acid (syn isomer)
IR (Nujol): 1770, 1670, 1530 cm$^{-1}$

(24) 7-[2-Allyloxyimino-2-(5-amino-1,2,4-thiadiazol-3-yl)acetamido]-3-[(Z)-2-(2-pyridyl)vinylthio]-3-cephem-4-carboxylic acid (syn isomer)
mp: 168° C. (dec.)
IR (Nujol): 1780, 1670, 1620, 1530 cm$^{-1}$
NMR (DMSO-d$_6$, δ): 3.70, 4.17 (2H, ABq, J=18 Hz), 4.73 (2H, d, J=5 Hz), 5.07–5.57 (2H, m), 5.23 (1H, d, J=5 Hz), 5.70–6.33 (2H, m), 6.67 (1H, d, J=11 Hz), 6.90 (1H, d, J=11 Hz), 7.07–7.50 (2H, m), 7.67–7.97 (1H, m), 8.00–8.30 (2H, m), 8.53–8.77 (1H, m), 9.67 (1H, d, J=8 Hz)

(25) 7-2-Allyloxyimino-2-(5-amino-1,2,4-thiadiazol-3-yl) acetamido]-3-[(E)-2-(2-pyridyl)vinylthio]-3-cephem-4-carboxylic acid (syn isomer)

mp: 160° C. (dec.)

IR (Nujol): 1770, 1670, 1615, 1580, 1530 cm$^{-1}$

NMR (DMSO-d$_6$, δ): 3.67, 4.10 (2H, ABq, J=18 Hz), 4.70 (2H, d, J=5 Hz), 5.07–6.40 (2H, m), 5.27 (1H, d, J=5 Hz), 5.70–6.40 (2H, M), 6.73 (1H, d, J=15 Hz), 7.23–7.97 (3H, m), 7.90 (1H, d, J=15 Hz), 8.00–8.27 (2H, m), 8.50–8.67 (1H, m), 9.63 (1H, d, J=9 Hz)

(26) 7-[2-(2-Aminothiazol-4-yl)-2-ethoxyiminoacetamido]-3-[(Z)-2-(3-pyridyl)vinylthio]-3-cephem-4-carboxylic acid (syn isomer)

IR (Nujol): 3250, 1770, 1660 cm$^{-1}$

(27) 7-[2-(2-Aminothiazol-4-yl)-2-ethoxyiminoacetamido]-3[(Z)-2-(1-methyl-3-pyridinio)vinylthio]-3-cephem-4-carboxylate (syn isomer)

IR (Nujol): 3300, 1760, 1650, 1600 cm$^{-1}$

(28) 7-[2-Allyloxyimino-2-(5-amino-1,2,4-thiadiazol-3-yl)acetamido]-3-[(Z)-2-cyanovinylthio]-3-cephem-4-carboxylic acid (syn isomer)

IR (Nujol): 3300, 2210, 1760, 1660, 1610 cm$^{-1}$

(29) 7-[2-(2-Aminothiazol-4-yl)2-carboxymethoxyiminoacetamido ]-3-[(Z)-2-(1-methyl-3-pyridinio)-vinylthio]-3-cephem-4-carboxylate (syn isomer)

IR (Nujol): 3300, 1765, 1670, 1600 cm$^{-1}$

(30) 7-[2-(5-Amino-1,2,4-thiadiazol-3-yl)-2-ethoxyiminoacetamido]-3-[(Z)-2-phenylvinylthio]-3-cephem-4-carboxylic acid (syn isomer)

mp: 165° (dec.)

IR (Nujol): 3275, 3175, 1770, 1680, 1670, 1540, 1520, 1400 cm$^{-1}$

(31) 7-[2-(5-amino-1,2,4-thiadiazol-3-yl)-2-hydroxyiminoacetamido]-3-[(Z)-2-(3-pyridyl)vinylthio])-3-cephem-4-carboxylic acid (syn isomer)

mp: 178°–182° (dec.)

IR (Nujol): 3300, 3150, 1770, 1670, 1610, 1530 cm$^{-1}$

(32) Benzhydryl 7-[2-(5-amino-1,2,4-thiadiazol-3-yl)-2-cyclopentyloxyiminoacetamido]-3-[(Z)-2(3-pyridyl)-vinylthio]-3-cephem-4-carboxylate (syn isomer)

NMR (DMSO-d$_6$, δ): 1.27–2.07 (8H, m), 3.73–4.17 (2H, m), 4.53–4.90 (1H, m), 5.23 (1H, d, J=5 Hz), 5.9 (1H, dd, J=5 Hz, 9 Hz), 6.50–7.05 (2H, m), 6.90 (1H, s), 7.05–7.90 (13H, m), 7.90–8.80 (3H, m), 8.08 (1H, s), 9.57 (1H, d, J=9 Hz)

(33) Benzhydryl 7-[2-(5-amino-1,2,4-thiadiazol-3-yl)-2(2-propynyloxyimino) acetamido]-3-[(Z)-2-(3-pyridyl)vinylthio]-3-cephem-4-carboxylate (syn isomer)

NMR (DMSO-d$_6$, δ): 3.50–4.05 (2H, m), 3.31 (1H, s), 5.31 (1H, d, J=4 Hz), 5.97 (1H, dd, J=5 Hz, 8 Hz), 6.79 (2H, dd, J=4 Hz, 10 Hz), 6.96 (1H, s), 7.03–7.64 (1H, m), 7.62–7.99 (1H, m), 7.97–8.58 (2H, m), 8.56–8.75 (2H, m), 9.79 (1H, d, J=8 Hz)

(34) Benzhydryl 7-[2-(5-amino-1,2,4-thiadiazol-3-yl)-2-methoxyiminoacetamido]-3-[(Z)-2-(1-methyl-3-pyridinio)vinylthio]-3-cephem-4-carboxylate iodide (syn isomer)

NMR (DMSO-d$_6$, δ): 3.90 (3H, s), 4.03 (3H, s), 3.57–4.27 (2H, m), 5.25 (1H, d, J=5 Hz), 5.92 (1H, d, J=5 Hz, 9 Hz), 6.75 (1H, d, J=11 Hz), 6.87 (1H, s), 7.07–7.62 (11H, m), 7.93–9.06 (6H, m), 9.58 (1H, d, J=9 Hz)

(35) 7-[2-(2-Aminothiazol-4-yl)-2-(2-cyclopenten-1-yl)oxyiminoacetamido]-3-[(Z)-2-(3-pyridyl)vinylthio]-3-cephem-4-carboxylic acid (syn isomer)

NMR (DMSO-d$_6$, δ): 1.86–2.57 (4H, m), 3.66 and 4.15 (2H, ABq, J=18 Hz), 5.13–5.40 (2H, m), 5.60–6.23 (3H, m), 6.50 (1H, s), 6.66 (1H, d, J=11 Hz), 6.87 (1H, d, J=11 Hz), 7.33–8.83 (4H, m), 9.53 (1H, d, J=8 Hz)

(36) Benzhydryl 7-[2-(2-aminothiazol-4-yl)-2-propoxyiminoacetamido]-3-[(Z)-2-(3-pyridyl)vinylthio]-3-cephem-4-carboxylate (syn isomer)

NMR (DMSO-d$_6$, δ): 0.95 (3H, t, J=7 Hz), 1.35–2.0 (2H, m), 3.73–4.37 (4H, m), 5.28 (1H, d, J=4 Hz), 5.9 (1H, dd, J=4 Hz, 8 Hz), 6.67–6.87 (2H, m), 6.92 (1H, s), 7.0–7.63 (12H, m), 7.63–8.82 (3H, m), 9.68 (1H, d, J=8 Hz)

(37) 7-[2-(5-Amino-1,2,4-thiadiazol-3-yl)-2-methoxyiminoacetamido]-3-[(Z)-2-(1-methyl-3-pyridinio)vinylthio]-3-cephem-4-carboxylate (syn isomer)

IR (Nujol): 3260, 1765, 1660, 1610 cm$^{-1}$

(38) 7-[2-(5-Amino-1,2,4-thiadiazol-3-yl)-2-ethoxyiminoacetamido]-3-[(Z)-2-(1-methyl-3-pyridinio)vinylthio]-3-cephem-4-carboxylate (syn isomer)

IR (Nujol): 3300, 1770, 1670, 1610 cm$^{-1}$

(39) 7-[2-(2-Aminothiazol-4-yl)-2-propoxyiminoacetamido]-3-[(Z)-2-(3-pyridyl)vinylthio]-3-cephem-4-carboxylic acid (syn isomer)

IR (Nujol): 3280, 3180, 1775, 1665 cm$^{-1}$

(40) 7-[2-(5-Amino-1,2,4-thiadiazol-3-yl)-2-cyclopenthyloxyiminoacetamido]-3-[(Z)-2-(3-pyridyl)vinylthio]-3-cephem-4-carboxylic acid (syn isomer)

IR (Nujol): 3270, 1770, 1670, 1615 cm$^{-1}$

(41) 7-[2-(5-Amino-1,2,4-thiadiazol-3-yl)-2-(2-propynyloxyimino)acetamido]-3-[(Z)-2-(3-pyridyl)-vinylthio]-3-cephem-4-carboxylic acid (syn isomer)

IR (Nujol): 3270, 1770, 1670, 1615 cm$^{-1}$

(42) 1-Acetoxyethyl 7-[2-(2-aminothiazol-4-yl)-2-allyloxyiminoacetamido]-3-[(Z)-2-(3-pyridyl)vinylthio]-3-cephem-4-carboxylate (syn isomer)

IR (Nujol): 3300, 1760–1780, 1670, 1240, 1210 1070 cm$^{-1}$

EXAMPLE 13

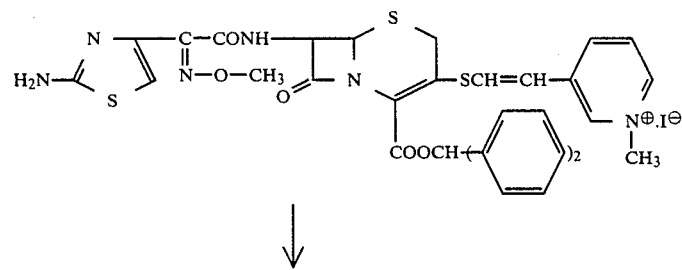

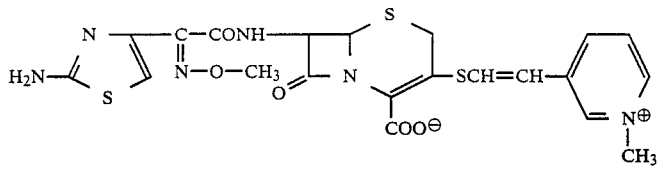

To a suspension of benzhydryl 7-[2-(2-aminothiazol-4-yl)2-methoxyiminoacetamido]-3-[(Z)-2-(1-methyl-3-pyridinio)vinylthio]-3-cephem-4-carboxylate iodide (syn isomer) (2.15 g) and anisole (2.81 g) in methylene chloride (5.5 ml) was added trifluoroacetic acid (5.93 g) under ice-cooling and the mixture was stirred at the same temperature for 1 hour. The reaction mixture was dropwise added isopropyl ether (200 ml) and the precipitates were collected by filtration. The precipitates were suspended in water and the suspension was adjusted to pH 5 with an aqueous solution of sodium bicarbonate, and an insoluble material was filtered off. The filtrate was subjected to column chromatography on macroporous non-ionic adsorption resin "Diaion HP-20" [Trademark: prepared byMitsubishi Chemical Industries] (40 ml) After the column was washed with water, the elution was carried out with 10% aqueous solution of isopropyl alcohol. The eluates containing the object compound were collected and evaporated to remove isopropyl alcohol under reduced pressure and the residue was lyophilized to give 7-[2-(2-aminothiazol-4-yl)-2-methoxyiminoacetamido]-3-[(Z)-2-(1-methyl-3-pyridinio)vinylthio]-3-cephem-4-carboxylate (syn isomer) (0.84 g).

mp:174°–178° C.

IR (Nujol): 3300, 1765, 1660, 1605, 1530 cm$^{-1}$

NMR (DMSO-d$_6$, δ): 3.02–4.05 (2H, m), 3.83 (3H, s), 4.38 (3H, s), 5.05 (1H, d, J=5 Hz), 5.58 (1H, dd, J=8 Hz, 5 Hz), 6.67 (1H, d, J=11 Hz), 6.72 (1H, s), 7.03 (1H, d, J=11 Hz), 7–9.23 (4H, m), 9.47 (1H, d, J=8 Hz)

EXAMPLE 14

To a suspension of benzhydryl 7-[2-allyloxyimino-2-(5-amino-1,2,4-thiadiazol-3-yl) acetamido]-3-[(Z)-2-(1-methyl-3-pyridinio)vinylthio]-3-cephem-4-carboxylate iodide (syn isomer) (2.71 g) and anisole (3.49 g) in methylene chloride (7 ml) was added trifluoroacetic acid (7.36 g) under ice-cooling and the mixture was stirred at the same temperature for 1 hour. The reaction mixture was dropwise added isopropyl ether (200 ml) and the precipitates were collected by filtration. The precipitates were suspended in water and the suspension was adjusted to pH 5 with an aqueous solution of sodium bicarbonate and an insoluble material was filtered off. The filtrate was subjected to column chromatography on macroporouos non-ionic adsorption resin "Diaion HP-20" (55 ml).

After the column was washed with water, the elution was carried out with 10% aqueous solution of isopropyl alcohol. The eluates containing the object compound were collected and evaporated to remove isopropyl alcohol under reduced pressure and the residue was lyophilized to give 7-[2-allyloxyimino-2-(5-amino-1,2,4-thiadiazol-3-yl) acetamido]-3-[(Z)-2-(1-methyl-3-pyridinio)vinylthio]-3-cephem-4-carboxylate (syn isomer) (0.44 g)

IR (Nujol): 3300, 1765, 1670, 1610 cm$^{-1}$

NMR (DMSO-d$_6$, δ): 3–3.9 (2H, m), 4.4 (3H, s), 4.67 (2H, d, J=5 Hz), 5–6.05 (5H, m), 6.67 (1H, d, J=11 Hz), 7.05 (1H, d, J=11 Hz), 7.92–9.25 (4H, m), 8.20 (2H, broad s), 9.45 (1H, d, J=8 Hz)

EXAMPLE 15

To a solution of benzhydryl 7-[2-(2-aminothiazol-4-yl)-2-methoxyiminoacetamido]-3-[(Z)-2-(3-pyridyl)vinylthio]-3-cephem-4-carboxylate (syn isomer) (0.8 g) and anisole (1.26 g) in methylene chloride (2 ml) was added trifluoroacetic acid (2.66 g) under ice-cooling and the mixture was stirred at the same temperature for 1 hour.

The reaction mixture was dropwise added to isopropyl ether (200 ml) and the precipitates were collected by filtration. The precipitates were added to a mixture of water and ethyl acetate and the mixture was adjusted to pH 7 with a saturated aqueous solution of sodium bicarbonate. The separated aqueous layer was added to ethyl acetate, and the mixture was adjusted to pH 3 with 10% hydrochloric acid. The separated organic layer was washed with brine, dried over magnesium sulfate and evaporated in vacuo to give 7-[2-(2-aminothiazol-4-yl)-2-methoxyiminoacetamido]-3-[(Z)-2-(3-pyridyl)vinylthio]-3-cephem-4-carboxylic acid (syn isomer) (0.37 g).

IR (Nujol): 3300, 1770, 1660, 1610, 1530 cm$^{-1}$

NMR (DMSO-d$_6$, δ): 3.52–4.26 (2H, m), 3.83 (3H, s), 5.20 (1H, d, J=5 Hz), 5.80 (1H, dd, J=8 Hz, 5 Hz), 6.67 (1H, d, J=11 Hz), 6.77 (1H, s), 6.87 (1H, d, J=11 Hz), 7–8.67 (4H, m), 9.6 (1H, d, J=8 Hz)

EXAMPLE 16

To a solution of benzhydryl 7-[2-allyloxyimino-2-(5-amino-1,2,4-thiadiazol-3-yl)acetamido]-3-[(Z)-2-(3-pyridyl)vinylthio]-3-cephem-4-carboxylate (syn isomer) (1.2 g) and anisole (1.82 g) in methylene chloride (3 ml) was added trifluoroacetic acid (3.84 g) under ice-cooling and the mixture was stirred at the same temperature for 1 hour. The reaction mixture was dropwise added to isopropyl ether (200 ml) and the precipitates were collected by filtration.

The precipitates were added to a mixture of water and ethyl acetate, and the mixture was adjusted to pH 7.0 with a saturated aqueous solution of sodium bicarbonate. The separated aqueous layer was acidified to pH 3.0 with 10% hydrochloric acid and the precipitates were collected by filtration to give 7-[2-allyloxyimino-2-(5-amino-1,2,4-thiadiazol-3-yl) acetamido]-3-[(Z)-2-(3-pyridyl)vinylthio]-3-cephem-4-carboxylic acid (syn isomer) (0.58 g).

IR (Nujol): 1770, 1670, 1610, 1530 cm$^{-1}$

NMR (DMSO-d$_6$, δ): 3.67 and 4.13 (2H, ABq, J=18 Hz), 4.67 (2H, d, J=5 Hz), 5–6.05 (5H, m), 6.69 (1H, d, J=12 Hz), 6.90 (1H, d, J=12 Hz), 7.33–8.67 (4H, m), 8.12 (2H, broad s), 9.63 (1H, d, J=8 Hz)

EXAMPLE 17

To a solution of benzhydryl 7-[2-(5-amino-1,2,4-thiadiazol-3-yl)-2-carboxymethoxyiminoacetamido]-3-[(Z)- 2(3-pyridyl)vinylthio]-3-cephem-4-carboxylate (syn isomer) (1.28 g) in a mixture of methylene chloride (3.8 ml) and anisole (1.28 ml) was added trifluoroacetic acid (2.6 ml) under ice-cooling. The mixture was stirred for 45 minutes at the same temperature. The mixture was poured into diisopropl ether (200 ml) to give a precipitate. The precipitate was collected, washed with diisopropyl ether and dissolved in a mixture of ethyl acetate and dilute aqueous solution of sodium bicarbonate at pH 5. The insoluble material was filtered off. The aqueous layer was separated and concentrated in vacuo in order to remove ethyl acetate. The aqueous solution was adjusted to pH 4.5 with dilute hydrochloric acid, subjected to column chromatography on macroporous non-ionic adsorption resin "Diaion HP-20" (20 ml) and eluted with water. The fractions containing the object compound were combined and concentrated in vacuo to about 20 ml. The concentrated solution was adjusted to pH 2 with dilute hydrochloric acid under ice-cooling to give a precipitate. The precipitate was collected, washed with cold water and dried over phosphorus pentoxide to give 7-[2-(5-amino-1,2,4-thiadiazol-3-yl)-2-carboxymethoxyiminoacetamido]-3-[(Z)-2-(3-pyridyl)-vinylthio]-3-cephem-4-carboxylic acid (syn isomer) (220 mg).

mp: 178° C. (dec.)

IR (Nujol): 1770, 1675, 1620, 1520 $cm^{-1}$

NMR (DMSO-$d_6$, $\delta$): 3.67, 4.13 (2H, ABq, J=18 Hz), 4.70 (2H, s), 5.23 (1H, d, J=5 Hz), 5.87 (1H, dd, J=5 Hz, 8 Hz), 6.87 (2H, s), 7.63 (1H, dd, J=6 Hz, 8 Hz), 8.00-8.50 (3H, m), 8.60 (1H, dd, J=2 Hz), 6 Hz), 8.77 (1H, d, J=2 Hz), 9.60 (1H, d, J=8 Hz)

EXAMPLE 18

The following compounds were obtained according to similar manners to those of Examples 13 to 17.

(1) 7-[2-(5-Amino-1,2,4-thiadiazol-3-yl)-2-ethoxyiminoacetamido]-3-[(Z)-2-(3-pyridyl)vinylthio]-3-cephem-4-carboxylic acid (syn isomer)

mp: 171° C. (dec.)

IR (Nujol): 3300, 3250, 1770, 1670, 1610 $cm^{-1}$

NMR (DMSO-$d_6$, $\delta$): 1.27 (3H, t, J=7 Hz), 3.66 and 4.12 (2H, ABq, J=18 Hz), 4.2 (2H, q, J=7 Hz), 5.23 (1H, d, J=5 Hz), 5.87 (1H, dd, J=8 Hz, 5 Hz), 6.71 (1H, d, J=11 Hz), 6.89 (1H, d, J=11 Hz), 7.48 (1H, dd, J=7 Hz), 7.95 (1H, dd, J=7.5 Hz, 2 Hz), 8.13 (2H, broad s), 8.49 (1H, d, J=5 Hz), 8.68 (1H, broad s), 9.58 (1H, d, J=8 Hz)

(2) 7-[2-(5-Amino-1,2,4-thiadiazol-3-yl)-2-methoxyiminoacetamido]-3-[(Z)-2-(3-pyridyl)vinylthio]-3-cephem-4-carboxylic acid (syn isomer)

mp: 164° C. (dec.)

IR (Nujol): 1770, 1670, 1530 $cm^{-1}$

NMR (DMSO-$d_6$, $\delta$): 3.30 and 4.13 (2H, ABq, J=18 Hz), 3.93 (3H, s), 5.20 (1H, d, J=5 Hz), 5.83 (1H, dd, J=5, 8 Hz), 6.73 (1H, d, J=12 Hz), 6.93 (1H, d, J=12 Hz), 7.50-7.73 (1H, m), 7.90-8.30 (3H, m), 8.40-8.90 (2H, m), 9.60 (1H, d, J=8 Hz)

(3) 7-[2-(2-Aminothiazol-4-yl)-2-(2-propynyloxyimino)acetamido]-3-[(Z)-2-(3-pyridyl)vinylthio]-3-cephem-4-carboxylic acid (syn isomer)

mp: 105°-110° C. (dec.)

IR (Nujol): 3200, 1770, 1670, 1190 $cm^{-1}$

NMR (DMSO-$d_6$, $\delta$): 3.47 (1H, s), 3.70 and 4.10 (2H, ABq, J=18 Hz), 4.74 -(2H, s), 5.26 (1H, d, J=5 Hz), 5.82 (1H, dd, J=5 Hz, 8 Hz), 6.86 (3H, broad s), 7.5-7.8 (1H, m), 7.9-8.2 (1H, m), 8.4-8.8 (2H, m), 9.74 (1H, d, J=8 Hz)

(4) 7-[2-Allyloxyimino-2-(2-aminothiazol-4-yl) acetamido]-3-[(Z)-2-(3-pyridyl)vinylthio]-3-cephem-4-carboxylic acid (syn isomer)

IR (Nujol): 1770, 1670, 1530 $cm^{-1}$

NMR (DMSO-$d_6$, $\delta$): 3.68 and 4.06 (2H, ABq, J=18 Hz), 4.60 (2H, d, J=5 Hz), 4.9-5.5 (2H, m), 5.23 (1H, d, J=5 Hz), 5.5-6.2 (2H, m), 6.80 (3H, s), 7.4-8.8 (4H, m), 9.66 (1H, d, J=8 Hz)

mp: 143°-146° C. (dec.)

(5) 7-[2-Allyloxyimino-2-(5-amino-1,2,4-thiadiazol-3-yl)acetamido]-3-[(Z)-2-(2-pyridyl)vinylthio]-3-cephem-4-carboxylic acid (syn isomer)

mp: 168° C. (dec.)

IR (Nujol): 1780, 1670, 1620, 1530 $cm^{-1}$

NMR (DMSO-$d_6$, $\delta$): 3.70, 4.17 (2H, ABq, J=18 Hz), 4.73 (2H, d, J=5 Hz), 5.07-5.57 (2H, m), 5.23 (1H, d, J=5 Hz), 5.70-6.33 (2H, m), 6.67 (1H, d, J=11 Hz), 6.90 (1H, d, J=11 Hz), 7.07-7.50 (2H, m), 7.67-7.97 (1H, m), 8.00-8.30 (2H, m), 8.53-8.77 (1H, m), 9.67 (1H, d, J=8 Hz)

(6) 7-[2-Allyloxyimino-2-(5-amino-1,2,4-thiadiazol-3-yl)acetamido]-3-[(E)-2-(2-pyridyl)vinylthio]-3-cephem-4-carboxylic acid (syn isomer)

mp: 160° C. (dec.)

IR (Nujol): 1770, 1670, 1615, 1580, 1530 $cm^{-1}$

NMR (DMSO-$d_6$, $\delta$): 3.67, 4.10 (2H, ABq, J=18 Hz), 4.70 (2H, d, J=5 Hz), 5.07-6.40 (2H, m), 5.27 (1H, d, J=5 Hz), 5.70-6.40 (2H, m), 6.73 (1H, d, J=15 Hz), 7.23-7.97 (3H, m), 7.90 (1H, d, J=15 Hz), 8.00-8.27 (2H, m), 8.50-8.67 (1H, m), 9.63 (1H, d, J=9 Hz (7) 7-[2-(2-Aminothiazol-4yl)-2-ethoxyiminoacetamido]-3-[(Z)-2-(3-pyridyl)vinylthio]-3-cephem-4-carboxylic acid (syn isomer)

IR (Nujol): 3250, 1770, 1660 $cm^{-1}$

NMR (DMSO-$d_6$, $\delta$): 1.27 (3H, t, J=7 Hz), 3.6-4.23 (2H, m), 4.2 (2H, q, J=7 Hz), 5.27 (1H, d, J=5 Hz), 5.85 (1H, dd, J=8 Hz, 5 Hz), 6.80 (1H, d, J=10 Hz), 6.81 (1H, s), 6.95 (1H, d, J=10 Hz), 7.53-8.63 (5H, m), 9.7 (1H, d, J=8 Hz)

(8) 7-[2-(2-Aminothiazol-4-yl)-2-ethoxyiminoacetamido]-3[(Z)-2-(1-methyl-3-pyridinio)vinylthio]-3cephem-4-carboxylate (syn isomer)

IR (Nujol): 3300, 1760, 1650, 1600 $cm^{-1}$

NMR (DMSO-$d_6$, $\delta$): 1.2 (3H, t, J=7 Hz), 3-3.9 (2H, m), 4.1 (2H, q, J=7 Hz), 4.37 (3H, s), 5.08 (1H, d, J=5 Hz), 5.6 (1H, dd, J=8 Hz, 5 Hz), 6.6 (1H, d, J=10 Hz), 6.7 (1H, s), 7.02 (1H, d, J=10 Hz), 7.12-9.27 (6H, m), 9.43 (1H, d, J=8 Hz), (9) 7-[2-Allyloxyimino-2-(5-amino-1,2,4-thiadiazol-3-yl) acetamido]-3-[(Z)-2-cyanovinylthio]-3-cephem-4-carboxylic acid (syn isomer)

mp: 182°-190° C. (dec.)

IR (Nujol): 3300, 2210, 1760, 1660, 1610 $cm^{-1}$

NMR (DMSO-$d_6$, $\delta$): 3.67 and 4.13 (2H, ABq, J=18 Hz), 4.67 (2H, d, J=5 Hz), 5.05-6.2 (5H, m), 5.2 (1H, d, J=5 Hz), 5.9 (1H, d, J=10 Hz), 7.77 (1H, d, J=10 Hz), 8.1 (2H, broad s), 9.6 (1H, d, J=8 Hz)

(10) 7-[D-N-(4-Ethyl-2,3-dioxo-1-piperazinylcarbonyl)-2-(4-hydroxyphenyl)glycinamido]-3-[(Z)-2-(3-pyridyl)vinylthio]-3-cephem-4-carboxylic acid IR (Nujol): 3200, 1770, 1710, 1675, 1605 $cm^{-1}$ NMR (DMSO-$d_6$, $\delta$): 1.07 (3H, t, J=7 Hz), 3.2-4.2 (6H, m), 3.42 (2H, q, J=7 Hz), 5.1 (1H, d, J=5 Hz), 5.5 (1H, d, J=8 Hz), 5.73 (1H, dd, J=8 Hz, 5 Hz), 6.67 (1H, d, J=10 Hz), 6.7 (2H, d, J=8 Hz), 6.73 (1H, s), 6.87 (1H, d, J=10 Hz), 7.2 (2H, d, J=8 Hz), 7.3-8.7 (4H, m), 9.4 (1H, d, J=8 Hz), 9.67 (1H, d, J=8 Hz)

(11) 7-[2-(2-Aminothiazol-4-yl)-2-carboxymethoxyiminoacetamido ]-3-[(Z)-2-(1-methyl-3-pyridinio)-vinylthio]-3-cephem-4-carboxylate (syn isomer)

IR (Nujol): 3300, 1765, 1670, 1600 cm$^{-1}$

(12) 7-[2-(5-Amino-1,2,4-thiadiazol-3-yl)-2-ethoxyiminoacetamido]-3-[(Z)-2-phenylvinylthio]-3-cephem-4-carboxylic acid (syn isomer)

mp: 165° C. (dec.)

IR (Nujol): 3275, 3175, 1770, 1680, 1670, 1540, 1520, 1400 cm$^{-1}$

(13) 7-[2-(5-Amino-1,2,4-thiadiazol-3-yl)-2-hydroxyiminoacetamido]-3-[(Z)-2-(3-pyridyl)vinylthio]-3-cephem-4-carboxylic acid (syn isomer)

mp: 178°-182° C. (dec.)

IR (Nujol): 3300, 3150, 1770, 1670, 1610, 1530 cm$^{-1}$

(14) 7-[2-(2-Cyclopenten-1-yl) oxyimino-2-(2-formamidothiazol-4-yl)acetamido]-3-[(Z)-2-(3-pyridyl)-vinylthio]-3-cephem-4-carboxylic acid (syn isomer)

IR (Nujol): 3250, 1765, 1650, 1610 cm$^{-1}$

(15) 7-[2-(2-Aminothiazol-4-yl)-2-(2-cyclopenten-1-yl) oxyiminoacetamido]-3-[(Z)-2-(3-pyridyl)vinylthio]-3-cephem-4-carboxylic acid (syn isomer)

NMR (DMSO-d$_6$, δ): 1.86-2.57 (4H, m), 3.66 and 4.15 (2H, ABq, J=18 Hz), 5.13-5.40 (2H, m), 5.60-6.23 (3H, m), 6.50 (1H, s), 6.66 (1H, d, J=11 Hz), 6.87 (1H, d, J=11 Hz), 7.33-8.83 (4H, m), 9.53 (1H, d, J=8Hz)

(16) 7-[2-(5-Amino-1,2,4-thiadiazol-3-yl)-2-methoxyiminoacetamido]-3-[(Z)-2-(1-methyl-3-pyridinio) vinylthio]-3-cephem-4-carboxylate (syn isomer)

IR (Nujol): 3260, 1765, 1660, 1610 cm$^{-1}$

NMR (DMSO-d$_6$, δ): 3.00-3.93 (2H, m), 3.87 (3H, s), 4.34 (3H, s), 5.00 (1H, d, J=5 Hz), 5.60 (1H, dd, J=5 Hz, 8 Hz), 6.80 (1H, d, J=11 Hz), 7.03 (1H, d, J=11 Hz), 7.77-9.09 (4H, m), 9.2 (2H, s), 9.43 (1H, d, J=8 Hz)

(17) 7-[2-(5-Amino-1,2,4-thiadiazol-3-yl)-2-ethoxyiminoacetamido]-3-[(Z)-2-(1-emthyl-3-pyridinio) vinylthio]-3-cephem-4-carboxylate (syn isomer)

IR (Nujol): 3300, 1770, 1670, 1610 cm$^{-1}$

NMR (DMSO-d$_6$, δ): 1.25 (3H, t, J=7 Hz), 3.0-3.93 (2H, m), 4.20 (2H, q, J=7 Hz), 4.36 (3H, s), 5.05 (1H, d, J=5 Hz), 5.50 (1H, dd, J=5 Hz, 8 Hz), 6.65 (1H, d, J=10 Hz), 7.04 (1H, d, J=10 Hz), 7.80-9.30 (4H, m), 8.17 (2H, s), 9.40 (1H, d, J=8 Hz)

(18) 7-[2-(2-Aminothiazol-4-yl)-2-propoxyiminoacetamido]-3-[(Z)-2-(3-pyridyl)vinylthio]-3-cephem-4-carboxylic acid (syn isomer)

IR (Nujol): 3280, 3180, 1775, 1665 cm$^{-1}$

NMR (DMSO-d$_6$, δ): 0.90 (3H, t, J=7 Hz), 1.66-2.0 (2H, m), 3.43-4.43 (4H, m), 5.19 (1H, d, J=5 Hz), 5.79 (1H, dd, J=5 Hz, 9 Hz), 6.48-6.95 (3H, m), 7.24-8.85 (6H, m), 9.60 (1H, d, J=9 Hz)

(19) 7-[2-(5-Amino-1,2,4-thiadiazol-3-yl)-2-cyclopenthyloxyiminoacetamido]-3-[(Z)-2-(3-pyridyl)vinylthio]-3-cephem-4-carboxylic acid (syn isomer)

IR (Nujol): 3270, 1770, 1670, 1615 cm$^{-1}$

NMR (DMSO-d$_6$, δ): 1.33-2.33 (8H, m), 3.50-4.27 (2H, m), 5.23 (1H, d, J=5 Hz), 5.90 (1H, dd, J=5 Hz, 9 Hz), 6.53-7.00 (2H, m), 7.27-8.83 (4H, m), 8.02 (1H, s), 9.57 (1H, d, J=9 Hz)

(20) 7-[2-(5-Amino-1,2,4-thiadiazol-3-yl)-2-(2-propynyloxyimino) acetamido]-3-[(Z)-2-(3-pyridyl)-vinylthio]-3-cephem-4-carboxylic acid (syn isomer)

IR (Nujol): 3270, 1770, 1670, 1615 cm$^{-1}$

NMR (DMSO-d$_6$, δ): 3.52 (1H, m), 3.66-4.08 (2H, m), 4.82 (2H, d, J=2 Hz), 5.19 (1H, d, J=4 Hz), 5.81 (1H, dd, J=4 Hz, 10 Hz), 6.92 (2H, dd, J=4 Hz, 10 Hz), 7.17-8.92 (6H, m), 9.15 (1H, d, J=10 Hz)

EXAMPLE 19

To a suspension of benzhydryl 7-[2-(2-aminothiazol-4-yl) -2-benzhydryloxycarbonylemethoxyiminoacetamido]-3-[(Z)-2-(1-methyl-3-pyridinio) vinylthio]-3-cephem-4-carboxylate iodide (syn isomer) (1.7 g) and anisole (1.77 g) in methylene chloride (43 ml) was added trifluoroacetic acid (3.74 g) under ice-cooling and the mixture was stirred at the same temperature for 2 hours. The reaction mixture was dropwise added to diisopropyl ether (200 ml) and the resulting precipitates were collected by filtration. The precipitates were suspended in water, adjusted to pH 3 with an aqueous solution of sodium bicarbonate, and the insoluble material was filtered off. The filtrate was subjected to column chromatography on macroporous non-ionic adsorption resin "Diaion HP-20" (30 ml). After the column was washed with water, the elution was carried out with 10% aqueous isopropyl alcohol. The eluates containing an object compound were collected and evaporated to remove isopropyl alcohol under reduced pressure, and the residue was lyophilized to give 7-[2-(2-aminothiazol-4-yl)-2-carboxymethoxyiminoacetamido]-3-[(Z)-2-(1-methyl-3-pyridinio)vinylthio]-3-cephem-4-carboxylate (syn isomer) (0.73 g).

mp: 188° C. (dec.)

IR (Nujol): 3300, 1765, 1670, 1600 cm$^{-1}$

NMR (DMSO-d$_6$, δ): 3.1 and 3.7 (2H, ABq, J=18 Hz), 4.3 (3H, s), 4.5 (2H, broad s), 5.02 (1H, d, J=5 Hz), 5.67 (1H, dd, J=8 Hz, 5 Hz), 6.67 (1H, d, J=10 Hz), 6.73 (1H, s), 6.92 (1H, d, J=10 Hz), 7-9.2 (6H, m), 10 (1 H, d, J=8 Hz)

EXAMPLE 20

The following compound was obtained according to a similar manner to that of Example 19.

7-[2-(5-Amino-1,2,4-thiadiazol-3-yl)-2-carboxymethoxyiminoacetamido]-3-[(Z)-2-(3-pyridyl)vinylthio]-3-cephem-4-carboxylic acid (syn isomer)

mp: 178° C. (dec.)

IR (Nujol): 1770, 1675, 1620, 1520 cm$^{-1}$

EXAMPLE 21

To a suspension of benzhydryl 7-[2-(5-amino-1,2,4-thiadiazol-3-yl)-2-(2-cyclopenten-1-yl) oxyiminoacetamido]-3-[(Z)-2-(3-pyridyl)vinylthio]-3-cephem-4-carboxylate (syn isomer) (1.06 g) in anisole (2 ml) was added trifluoroacetic acid (4 ml) under ice-cooling and the mixture was stirred for 35 minutes at the same temperature. The mixture was poured into diisopropyl ether (250 ml). The precipitate was collected, washed with diisopropyl ether and dried over phosphorus pentoxide. The precipitate was dissolved in a mixture of tetrahydrofuran (50 ml), sodium bicarbonate (242 mg), water (40 ml) and ethyl acetate (50 ml). The aqueous layer was separated and adjusted to pH 2 with 1N hydrochloric acid. The resultant precipitate was collected, washed with cold water and dried over phosphorus pentoxide to give 7-[2-(5-amino-1,2,4-thiadiazol-3-yl)-2-hydroxyiminoacetamido]-3-[(Z)-2-(3-pyridyl)-vinylthio]-3-cephem-4-carboxylic acid (syn isomer) (390 mg). mp 178°-182° C. (dec.)

IR (Nujol): 3300, 3150, 1770, 1670, 1610, 1530 cm$^{-1}$

NMR (DMSO-d$_6$, δ): 3.65 and 4.12 (2H, ABq, J=18 Hz), 5.22 (1H, d, J=5 Hz), 5.85 (1H, dd, J=5 Hz and 8 Hz), 6.80 (2H, s), 7.4-7.8 (1H, m), 7.8-8.2 (3H, m), 8.4-8.6 (1H, m), 8.6-8.8 (1H, m), 9.47 (1H, d, J=8 Hz), 11.9 (1H, broad s).

EXAMPLE 22

To a suspension of [(Z)-2-(3-pyridyl)vinylthio]silver (5.86 g) in acetonitrile (176 ml) was added sodium iodide (21.58 g) at ambient temperature.

The mixture was stirred for 30 minutes. To the mixture was added a solution of benzhydryl 7-amino-3-mesyloxy-3-cephem-4-carboxylate (9.21 g) and bis(trimethylsilyl)urea (12.26 g) in acetonitrile (276 ml) under ice-cooling. The reaction mixture was stirred for 10 minutes at the same temperature. The insoluble material was filtered off. The filtrate was concentrated in vacuo and the residue was dissolved in ethyl acetate. The ethyl acetate solution was washed with water and brine, dried over magnesium sulfate and evaporated in vacuo to give benzhydryl 7-amino-3-[(Z)-2-(3-pyridyl)vinylthio]-3-cephem-4-carboxylate (6.17 g).

IR (Nujol): 1765, 1720, 1650 cm$^{-1}$

NMR (DMSO-d$_6$, δ): 3.70 and 4.13 (2H, ABq, J=18 Hz), 4.90 (1H, d, J=5 Hz), 5.11 (1H, d, J=5 Hz), 6.67 (1H, d, J=11 Hz), 6.83 (1H, d, J=11 Hz), 6.93 (1H, s), 7.17–7.62 (11H, m), 7.62–8.65 (3H, m)

EXAMPLE 23

To a suspension of [(Z)-2-(3-pyridyl)vinylthio]-silver (2.86 g) in acetonitrile (90 ml) was added sodium iodide (8.77 g) at ambient temperature. The mixture was stirred for 30 minutes. To the resultant mixture was added a solution of benzhydryl 7[2-allyloxyimino-2-(5-amino-1,2,4-thiadiazol-3-yl)-acetamido]-3-mesyloxy-3-cephem-4-carboxylate (syn isomer) (6.54 g) in acetonitrile (196 ml) under ice-cooling.

The mixture was stirred for 10 minutes at the same temperature. The insoluble material was filtered off. The filtrate was concentrated in vacuo and the residue was dissolved in ethyl acetate. The ethyl acetate solution was washed with water and brine, dried over magnesium sulfate and evaporated in vacuo to give a residue. The residue was subjected to column chromatography on silica gel and eluted with a mixture of ethyl acetate and methylene chloride (1:1). The fractions containing the object compound were combined and evaporated in vacuo to give benzhydryl 7-[2-allyloxyimino-2-(5-amino-1,2,4-thiadiazol-3-yl)acetamido] -3-[(Z)-2-(3-pyridyl)vinylthio]-3-cephem-4-carboxylate (syn isomer) (3.5 g).

IR (Nujol): 1760, 1730, 1660, 1605 cm$^{-1}$

NMR (DMSO-d$_6$, δ): 3.52–4.12 (2H, m), 4.67 (2H, d, J=5 Hz), 5.05–6.15 (5H, m), 6.67 (1H, d, J=12 Hz), 6.87 (1H, d, J=12 Hz), 6.93 (1H, s), 7.04–7.62 (11H, m), 7.62–8.69 (3H, m), 8.12 (2H, broad s), 9.7 (1H, d, J=8 Hz)

EXAMPLE 24

To a suspension of 7-[2-(5-amino-1,2,4-thiadiazol-3-yl)-2-ethoxyiminoacetamido]-3-mesyloxy-3-cephem-4-carboxylic acid (syn isomer) (1 g) in tetrahydrofuran (30 ml) was added bis(trimethylsilyl) urea (444 mg) at ambient temperature. The mixture was stirred at 30°–35° C. for 30 minutes to give a clear solution. On the other hand, to a solution of (Z)-2-acetylthiovinylbenzene (780 mg) in tetrahydrofuran (6 ml) was added sodium methoxide (240 mg) at 0° C. The mixture was stirred for 30 minutes. This solution was added to the above-mentioned clear solution. The mixture was stirred for 2 hours at −20°~−30° C. The mixture was poured into water (300 ml), and then the mixture was neutralized with sodium bicarbonate and washed with ethyl acetate. After stirring the aqueous layer was separated. The aqueous solution was adjusted to pH 2.5 with 1N hydrochloric acid. To this solution was added ethyl acetate (200 ml). The organic layer was separated, dried over magnesium sulfate and concentrated in vacuo to give a solid. The solid was triturated with diisopropyl ether to give 7-[2-(5-amino-1,2,4-thiadiazol-3-yl)-2-ethoxyiminoacetamido]-3-[(Z)-2-phenylvinylthio]-3-cephem-4-carboxylic acid (syn isomer) (550 mg).

m.p. 165° C. (dec.)

IR (Nujol): 3275, 3175, 1770, 1680, 1670, 1540, 1520, 1400 cm$^{-1}$

NMR (DMSO-d$_6$, δ): 1.24 (3H, t, J=8 Hz), 3.3–3.8 (2H, m), 4.17 (2H, q, J=8 Hz), 3.8–4.4 (2H, m), 5.2 (1H, d, J=5 Hz), 5.84 (1H, dd, J=5 Hz, 8 Hz), 6.55, 6.75 (2H, ABq, J=11 Hz), 7.4–7.5 (5H, broad s), 8.1 (2H, broad s), 9.55 (1H, d, J=8 Hz)

EXAMPLE 25

To a suspension of [(Z and E)-2-(2-pyridyl)vinylthio]-silver (2.26 g) in acetonitrile (140 ml) was added sodium iodide (8.18 g) under ice-cooling. The mixture was stirred at the same temperature for 30 minutes. To this mixture was added benzhydryl 7-formamido-3-mesyloxy-3-cephem-4-carboxylate (4 g) at once at the same temperature. The mixture was stirred under ice-cooling for 30 minutes. The insoluble material was filtered off. The filtrate was concentrated in vacuo to give a residue. The residue was dissolved in a mixture of ethyl acetate and a saturated aqueous solution of sodium chloride. The mixture was stirred for 1 hour. Sellaite was added to the mixture. The insoluble material was filtered off. The separated organic layer was washed with a saturated aqueous solution of sodium chloride, dried over magnesium sulfate and concentrated in vacuo to give a solid. The solid was subjected to column chromatography on silica gel (175 g) and eluted with a mixture of chloroform and ethyl acetate (4:1 v/v). The fractions containing the material having a larger Rf value in thin layer chromatography were combined and concentrated in vacuo to give benzhydryl 7-formamido-3-[(Z)-2-(2-pyridyl)vinylthio]-3-cephem-4-carboxylate (2.15 g) as a solid.

IR (Nujol): 1770, 1690–1660, 1590, 1580 cm$^{-1}$

NMR (DMSO-d$_6$, δ): 3.80, 4.17 (2H, ABq, J=18 Hz), 5.23 (1H, d, J=5 Hz), 5.87 (1H, dd, J=5 Hz, 9 Hz), 6.67 (1H, d, J=11 Hz), 6.87 (1H,d, J=11 Hz), 6.90 (1H, s) 7.03–7.60 (12H, m), 7.63–8.03 (1H, m), 8.17 (1H, s), 8.50–8.70 (1H, m), 9.10 (1H, d, J=9 Hz)

The fractions containing the material having a smaller Rf value in the thin layer chromatography were combined and concentrated in vacuo to give benzhydryl 7-formamido-3-[(E)-2-(2-pyridyl)vinylthio]-3-cephem-4-carboxylate (500 mg) as a solid.

IR (Nujol): 1780, 1690, 1660, 1600, 1580 cm$^{-1}$

NMR (DMSO-d$_6$, δ): 3.77, 4.14 (2H, ABq, J=18 Hz), 5.27 (1H, d, J=5 Hz), 5.90 (1H, dd, J=5 Hz, 8 Hz), 6.77 (1H, d, J=15 Hz), 6.90 (1H, s), 8.43–8.67 (1H, m), 9.13 (1H, d, J=8 Hz)

EXAMPLE 26

The following compounds were obtained according to similar manners to those of Examples 22 to 25.

(1) Benzhydryl 7-[2-(2-formamidothiazol-4-yl)-2-methoxyiminoacetamido]-3-[(Z)-2-(3-pyridyl)vinylthio]-3-cephem-4-carboxylate (syn isomer)

IR (Nujol): 3250, 1770, 1705, 1680, 1650 cm$^{-1}$ (2) Benzhydryl 7-[2-(2-formamidothiazol-4-yl)-2-methoxyiminoacetamido]-3-[(Z)-2-(1-methyl-3- pyridinio)vinylthio]-3-cephem-4-carboxylate iodide (syn isomer)

IR (Nujol): 1775, 1720, 1640, 1540 cm$^{-1}$ (3) Benzhydryl 7-[2-(2-aminothiazol-4-yl)-2-methoxyiminoacetamido]-3-[(Z)-2-(3-pyridyl)vinylthio]-3-cephem-4-carboxylate (syn isomer)

IR (Nujol): 1775, 1720, 1670, 1605, 1530 cm$^{-1}$ (4) 7-[2-(2-Aminothiazol-4-yl)-2-methoxyiminoacetamido]-3-[(Z)-2-(3-pyridyl)vinylthio]-3-cephem-4-carboxylic acid (syn isomer)

IR (Nujol): 3300, 1770, 1660, 1610, 1530 cm$^{-1}$ (5) Benzhydryl 7-[2-(2-aminothiazol-4-yl)-2-methoxyiminoacetamido]-3-[(Z)-2-(1-methyl-3-pyridinio)vinylthio]-3-cephem-4-carboxylate iodide (syn isomer)

IR (Nujol): 1770, 1710, 1660, 1620 cm$^{-1}$ (6) 7-[2-(2-Aminothiazol-4-yl)-2-methoxyiminoacetamido]-3-[(Z)-2-(1-methyl-3-pyridinio)vinylthio]-3-cephem-4-carboxylate (syn isomer)

IR (Nujol): 3300, 1765, 1660, 1605, 1530 cm$^{-1}$ (7) 7-[2-Allyloxyimino-2-(5-amino-1,2,4-thiadiazol-3-yl)acetamido]-3-[(Z)-2-(3-pyridyl)vinylthio]-3-cephem-4-carboxylic acid (syn isomer)

IR (Nujol): 1770, 1670, 1610, 1530 cm$^{-1}$ (8) Benzhydryl 7-[2-allyloxyimino-2-(5-amino-1,2,4-thiadiazol-3-yl) acetamido]-3-[(Z)-2-(1-methyl-3-pyridinio) vinylthio]-3-cephem-4-carboxylate iodide (syn isomer)

IR (Nujol): 1775, 1720, 1650, 1600 cm$^{-1}$ (9) 7-[2-Allyloxyimino-2-(5-amino-1,2,4-thiadiazol-3-yl)acetamido]-3-[(Z)-2-(1-methyl-3-pyridinio)vinylthio]-3-cephem-4-carboxylate (syn isomer)

IR (Nujol): 3300, 1765, 1670, 1610 cm$^{-1}$

(10) Benzhydryl 7-[2-(5-amino-1,2,4-thiadiazol-3-yl)-2-ethoxyiminoacetamido]-3-[(Z)-2-(3-pyridyl)vinylthio]-3-cephem-4-carboxylate (syn isomer)

IR (Nujol): 3350, 3150, 1780, 1730, 1675, 1615 cm$^{-1}$

NMR (DMSO-d$_6$, δ): 1.18, (3H, t, J=7 Hz), 3.77 and 4.11 (2H, ABq, J=18 Hz), 4.19 (2H, q, J=7Ha), 5.29 (1H, d, J=5 Hz), 5.94 (1H, dd, J=9 Hz, 5 Hz), 6.74 (1H, d, J=12 Hz), 6.86 (1H, d, J=12 Hz), 6.96 (1H, s), 7.2–7.6 (12H, m), 7.79 (1H, d, J=10 Hz), 8.12 (2H, broad s), 8.49 (1H, d, J=4 Hz), 8.61 (1H, broad s), 9.65 (1H, d, J=9 Hz)

(11) 7-[2-(5-Amino-1,2,4-thiadiazol-3-yl)-2-ethoxyiminoacetamido]-3-[(Z)-2-(3-pyridyl)vinylthio]-3-cephem-4-carboxylic acid (syn isomer)

mp 171° C. (dec.)

IR (Nujol): 3300, 3250, 1770, 1670, 1610 cm$^{-1}$

(12) Benzhydryl 7-[2-(5-amino-1,2,4-thiadiazol-3-yl)-2-methoxyiminoacetamido]-3-[(Z)-2-(3-pyridyl)vinylthio]-3-cephem-4-carboxylate (syn isomer)

IR (Nujol): 1770, 1670, 1610, 1520 cm$^{-1}$

NMR (DMSO-d$_6$, δ): 3.27 (3H, s), 3.77–4.10 (2H, m), 5.27 (1H, d, J=5 Hz), 5.93 (1H, dd, J=5 Hz, 9 Hz), 6.73 (2H, broad s), 6.90 (1H, s), 7.13–7.60 (11H, m), 7.63–7.90 (1H, m), 7.93–8.23 (2H, m), 8.37–8.63 (2H, m), 9.60 (1H, d, J=9 Hz)

(13) 7-[2-(5-Amino-1,2,4-thiadiazol-3yl)2-methoxyiminoacetamido ]-3-[(Z)-2-(3-pyridyl)vinylthio]-3-cephem-4-carboxylic acid (syn isomer)

mp 164° C. (dec.)

IR (Nujol): 1770, 1670, 1530 cm$^{-1}$

(14) Benzhydryl 7-[2-(5-amino-1,2,4-thiadiazol-3-yl)-2-(2-cyclopenten-1-yl) oxyiminoacetamido]-3-[(Z)-2-(3-pyridyl)vinylthio]-3-cephem-4-carboxylate (syn isomer)

IR (Nujol): 3300, 3150, 1780, 1675, 1610, 1530, 1280, 1220 cm$^{-1}$

(15) Benzhydryl 7-[2-(5-amino-1,2,4-thiadiazol-3-yl)-2-carboxymethoxyiminoacetamido]-3-[(Z)-2-(3-pyridyl)vinylthio]-3-cephem-4-carboxylate (syn isomer)

IR (Nujol): 1770, 1730, 1670, 1610, 1520 cm$^{-1}$

(16) Benzhydryl 7-[D-N-(4-ethyl-2,3-dioxo-1-piperazinylcarbonyl)-2-(4-hydroxyphenyl)-glycinamido]-3-[(Z)-2-(3-pyridyl)vinylthio]-3-cephem-4-carboxylate IR (Nujol): 3250, 1780, 1705, 1670, 1605 cm$^{-1}$

(17) Benzhydryl 7-[2-(2-formamidothiazol-4-yl)-2-(2-propynyloxyimino) acetamido]-3-[(Z)-2-(3-pyridyl)vinylthio]-3-cephem-4-carboxylate (syn isomer)

IR (Nujol): 1780, 1680, 1550, 1280, 1225 cm$^{-1}$

(18) Benzhydryl 7-[2-allyloxyimino-2-(2-formamidothiazol-4-yl) acetamido]-3-[(Z)-2-(3-pyridyl)vinylthio]-3-cephem-4-carboxylate (syn isomer)

IR (Nujol): 1780, 1690, 1670, 1550, 1280, 1220 cm$^{-1}$

(19) Benzhydryl 7-[2-benzhydryloxycarbonylmethoxyimino-2(2-formamidothiazol-4-yl)acetamido]-3-[(Z)-2-(3-pyridyl)vinylthio]-3-cephem-4-carboxylate (syn isomer)

IR (Nujol): 1780, 1730, 1680, 1540 cm$^{-1}$

(20) Benzhydryl 7-[2-ethoxyimino-2-(2-formamidothiazol-4-yl) acetamido]-3-[(Z)-2-(3-pyridyl)vinylthio]-3-cephem-4-carboxylate (syn isomer)

IR (Nujol): 1780, 1680, 1540 cm$^{-1}$

(21) Benzhydryl 7-[2-allyloxyimino-2-(5-amino-1,2,4-thiadiazol-3yl) acetamido]-3-[(E)-2-(2-pyridyl)vinylthio]-3-cephem-4-carboxylate (syn isomer)

IR (Nujol): 1775, 1675, 1610, 1520 cm$^{-1}$

(22) Benzhydryl 7-[2-allyloxyimino-2-(5-amino-1,2,4-thiadiazol-3yl) acetamido]-3-[(Z)-2-(2-pyridyl)vinylthio]-3-cephem-4-carboxylate (syn isomer)

IR (Nujol): 1780, 1680, 1620, 1600, 1530 cm$^{-1}$

(23) Benzhydryl 7-[2-allyloxyimino-2-(5-amino-1,2,4-thiadiazol-3-yl) acetamido]-3-[(Z)-2-cyanovinylthio]-3-cephem-4-carboxylate (syn isomer)

IR (Nujol): 3300, 2210, 1780, 1675, 1610 cm$^{-1}$

(24) Benzhydryl 7-[2-benzhydryloxycarbonylmethoxyimino-2-(2-formamidothiazol-4yl)acetamido]-3-[(Z)-2-(1-methyl-3-pyridinio)vinylthio]-3-cephem-4-carboxylate iodide (syn isomer)

IR (Nujol): 3350, 1760, 1735, 1660 cm$^{-1}$

(25) Benzhydryl 7-[2-ethoxyimino-2-(2-formamidothiazol-4-yl)acetamido]-3-[(Z)-2-(1-methyl-3-pyridinio)-vinylthio]-3-cephem-4-carboxylate iodide (syn isomer)

IR (Nujol): 1780, 1720, 1650 cm$^{-1}$

(26) Benzhydryl 7-[2-(2-aminothiazl-4-yl)-2-(2-propynyloxyimino)acetamido]-3-[(Z)-2-(3-pyridyl)-vinylthio]-3-cephem-4-carboxylate (syn isomer)

IR (Nujol): 1770, 1670, 1530, 1270, 1215 cm$^{-1}$

(27) Benzhydryl 7-[2-allyloxyimino-2-(2-aminothiazol-4-yl)acetamido]-3-[(Z)-2(3-pyridyl)vinylthio]-3-cephem-4-carboxylate (syn isomer)

IR (Nujol): 3300, 1780, 1670, 1610, 1535, 1280, 1220 cm$^{-1}$

(28) Benzhydryl 7-[2-(2-aminothiazol-4-yl)-2-benzhydryloxycarbonylmethoxyenzhydryliminoacetamido]-3-[(Z)-2-(1-methyl-3-pyridinio) vinylthio]-3-cephem-4-carboxylate iodide (syn isomer)

NMR (DMSO-d$_6$, δ): 3.6–4.2 (2H, m), 4.3 (3H, s), 4.9 (2H, s), 5.28 (1H, d, J=5 Hz), 5.9 (1H, dd, J=8 Hz), 6.75 (1H, d, J=10 Hz), 6.87 (3H, s), 7.03 (1H, d, J=10 Hz), 7–9.05 (24H, m), 9.83 (1H, d, J=8 Hz)

(29) B8 7-[2-(2-aminothiazol-4-yl)-2-ethoxyiminoacetamido)-3-[(Z)-2-(3-pyridyl)vinylthio]-3-cephem-4-carboxylate (syn isomer)

IR (Nujol): 1780, 1720, 1675 cm$^{-1}$

(30) Benzhydryl 7-[2-(2-aminothiazol-4-yl)-2-ethoxyiminoacetamido]-3-[(Z)-2-(1-methyl-3-pyridinio) vinylthio]-3-cephem-4-carboxylate iodide (syn isomer)

IR (Nujol): 1770, 1670, 1625 cm$^{-1}$

(31) 7-[2-(5-Amino-1,2,4-thiadiazol-3-yl)-2-carboxymethoxyiminoacetamido ]-3-[(Z)-2-(3-pyridyl)vinylthio]-3-cephem-4-carboxylic acid (syn isomer)

mp: 178° C. (dec.)
IR (Nujol): 1770, 1675, 1620, 1520 cm$^{-1}$

(32) 7-[2-(2-Aminothiazol-4-yl)-2-(2-propynyloxyimino)acetamido]-3-[(Z)-2-(3-pyridyl)vinylthio]-3-cephem-4-carboxylic acid (syn isomer)
IR (Nujol): 3200, 1770, 1670, 1190 cm$^{-1}$

(33) 7-[2-Allyloxyimino-2-(2-aminothiazol-4-yl) acetamido]-3-[(Z)-2-(3-pyridyl)vinylthio]-3-cephem-4-carboxylic acid (syn isomer)
IR (Nujol): 1770, 1670, 1530 cm$^{-1}$

(34) 7-[2-Allyloxyimino-2-(5-amino-1,2,4-thiadiazol-3-yl) acetamido]-3-[(Z)-2-(2-pyridyl)vinylthio]-3-cephem-4carboxylic acid (syn isomer) mp: 168° C. (dec.)
IR (Nujol): 1780, 1670, 1620, 1530 cm$^{-1}$

(35) 7-[2-Allyloxyimino-2-(5-amino-1,2,4-thiadiazol-3-yl)acetamido]-3-[(E)-2-(2-pyridyl)vinylthio]-3-cephem-4-carboxylic acid (syn isomer)
mp: 160° C. (dec.)
IR (Nujol): 1770, 1670, 1615, 1580, 1530 cm$^{-1}$

(36) 7-[2-(2-Aminothiazol-4-yl)-2-ethoxyiminoacetamido]-3-[(Z)-2-(3-pyridyl)vinylthio]-3-cephem-4-carboxylic acid (syn isomer)
IR (Nujol): 3250, 1770, 1660 cm$^{-1}$

(37) 7-[2-(2-Aminothiazol-4-yl)-2-ethoxyiminoacetamido]-3-[(Z)-2-(1-methyl-3-pyridinio)vinylthio]-3-cephem-4-carboxylate (syn isomer)
IR (Nujol): 3300, 1760, 1650, 1600 cm$^{-1}$

(38) 7-[2-Allyloxyimino-2-(5-amino-1,2,4-thiadiazol-3-yl)acetamido]-3-[(Z)-2-cyanovinylthio]-3-cephem-4-carboxylic acid (syn isomer)
IR (Nujol): 3300, 2210, 1760, 1660, 1610 cm$^{-1}$

(39) 7[D-N-(4-Ethyl-2,3-dioxo-1-piperazinylcarbonyl)-2-(4-hydroxyphenyl) glycinamido]-3-[(Z)-2-(3-pyridyl)vinylthio]-3-cephem-4-carboxylic acid
IR (Nujol): 3200, 1770, 1710, 1675, 1605 cm$^{-1}$

(40) 7-[2-(2-Aminothiazol-4-yl)2-carboxymethoxyiminoacetamido]-3-[(Z)-2-(1-methyl-3-pyridinio) vinylthio]-3-cephem-4-carboxylate (syn isomer)
IR (Nujol): 3300, 1765, 1670, 1600 cm$^{-1}$

(41) Benzhydryl 7-formamido-3-[(Z)-2-cyanovinylthio]-3-cephem-4-carboxylate
IR (Nujol): 3300, 2210, 1780, 1730, 1680 cm$^{-1}$
NMR (DMSO-d$_6$, δ): 3.77 and 4.15 (2H, ABq, J=18 Hz), 5.22 (1H, d, J=5 Hz), 5.9 (1H, dd, J=8 Hz, 5 Hz), 5.91 (1H, d, J=10 Hz), 6.97 (1H, s), 7.2–7.6 (10H, m), 7.77 (1H, d, J=10 Hz), 8.17 (1H, s), 9.10 (1H, d, J=8 Hz)

(42) Benzhydryl 7-formamido-3-[(Z)-2-(3-pyridyl)-vinylthio]-3-cephem-4-carboxylate
IR (Nujol): 1785, 1705, 1690, 1560, 1220 cm$^{-1}$
NMR (DMSO-d$_6$, δ): 3.76 and 4.14 (2H, ABq, J=18 Hz), 5.23 (1H, d, J=5 Hz), 5.85 (1H, dd, J=5 Hz and 8 Hz), 6.77 (2H, s), 6.93 (1H, s), 7.1–7.6 (11H, m), 7.77 (1H, dt, J=2 Hz and 8 Hz), 8.17 (1H, s), 8.47 (1H, dd, J=2 Hz and 5 Hz), 8.58 (1H, d, J=2 Hz), 9.12 (1H, d, J=8 Hz)

(43) 7-[2-(5-Amino-1,2,4-thiadiazol-3-yl)-2-hydroxyiminoacetamido]-3-[(Z)-2-(3-pyridyl)vinylthio]-3-cephem-4-carboxylic acid (syn isomer)
mp. 178°–182° C. (dec.)
IR (Nujol): 3300, 3150, 1770, 1670, 1610, 1530 cm$^{-1}$

(44) Benzhydryl 7-amino-3-[(E)-2-(2-pyridyl)vinylthio]-3-cephem-4-carboxylate
IR (Nujol): 1775, 1740 cm$^{-1}$

(45) Benzhydryl 7-amino-3-[(Z)-2-(2-pyridyl vinylthio]- 3-cephem-4-carboxylate.
IR (Nujol): 1765, 1715, 1590, 1580 cm$^{-1}$

(46) 7-[2-(2-Cyclopenten-1-yl)oxyimino-2-(2-formamidothiazol-4-yl) acetamido]-3-[(Z)-2-(3-pyridyl)-vinylthio]-3-cephem-4-carboxylic acid (syn isomer)
IR (Nujol): 3250, 1765, 1650, 1610 cm$^{-1}$

(47) Benzhydryl 7-[2-(2-formamidothiazol-4-yl)-2-propoxyiminoacetamido]-3-[(Z)-2-(3-pyridyl)vinylthio]-3-cephem-4-carboxylate (syn isomer)
NMR (DMSO-d$_6$, δ): 0.95 (3H, t, J=7 Hz), 1.35–2.0 (2H, m), 3.73–4.37 (4H, m), 5.28 (1H, d, J=4 Hz), 5.90 (1H, dd, J=4 Hz, 8 Hz), 6.67–6.87 (2H, m), 6.92 (1H, s), 7.0–7.63 (12H, m), 7.63–8.83 (3H, m), 8.5 (1H, s), 9.68 (1H, d, J=8 Hz)

(48) Benzhydryl 7-[2-(5-amino-1,2,4-thiadiazol-3-yl)-2-cyclopentyloxyiminoacetamido]-3-[(Z)-2-(3-pyridyl)-vinylthio]-3-cephem-4-carboxylate (syn isomer)
NMR (DMSO-d$_6$, δ): 1.27–2.07 (8H, m), 3.73–4.17 (2H, m), 4.53–4.90 (1H, m), 5.23 (1H, d, J=5 Hz), 5.9 (1H, dd, J=5 Hz, 9 Hz), 6.50–7.05 (2H, m), 6.90 (1H, s), 7.05–7.90 (13H, m), 7.90–8.80 (3H, m), 8.08 (1H, s), 9.57 (1H, d, J=9 Hz)

(49) Benzhydryl 7-[2-(5-amino-1,2,4-thiadiazol-3-yl)-2-(2-propynyloxyimino) acetamido]-3-[(Z)-2-(3-pyridyl)vinylthio]-3-cephem-4-carboxylate (syn isomer)
NMR (DMSO-d$_6$, δ): 3.50–4.05 (2H, m), 3.31 (1H, s), 5.31 (1H, d, J=4 Hz), 5.97 (1H, dd, J=5 Hz, 8 Hz), 6.79 (2H, dd, J=4 Hz, 10 Hz), 6.96 (1H, s), 7.03–7.64 (1H, m), 7.62–7.99 (1H, m), 7.97–8.58 (2H, m), 8.56–8.75 (2H, m), 9.79 (1H, d, J=8 Hz)

(50) Benzhydryl 7-[2-(5-amino-1,2,4-thiadiazol-3-yl)-2-emthoxyiminoacetamido]-3-[(Z)-2-(1-methyl-3-pyridinio)vinylthio]-3-cephem-4-carboxylate iodide (syn isomer)
NMR (DMSO-d$_6$, δ): 3.90 (3H, s), 4.03 (3H, s), 3.57–4.27 (2H, m), 5.25 (1H, d, J=5 Hz), 5.92 (1H, dd, J=5 Hz, 9 Hz), 6.75 (1H, d, J=11 Hz), 6.87 (1H, s), 7.07–7.62 (11H, m), 7.93–9.06 (6H, m), 9.58 (1H, d, J=9 Hz)

(51) 7-[2-(2-Aminothiazol-4-yl)-2-(2-cyclopenten-1-yl) -oxyiminoacetamido]-3-[(Z)-2-(3-pyridyl)vinylthio]-3-cephem-4-carboxylic acid (syn isomer)
NMR (DMSO-d$_6$, δ): 1.86–2.57 (4H, m), 3.66 and 4.15 (2H, ABq, J=18 Hz), 5.1–5.40 (2H, m), 5.60–6.23 (3H, m), 6.50 (1H, s), 6.66 (1H, d, J=11 Hz), 6.87 (1H, d, J=11 Hz), 7.33–8.83 (4H, m), 9.53 (1H, d, J=8 Hz)

(52) Benzhydryl 7-[2-(2-aminothiazol-4-yl)-2-propoxyiminoacetamido]-3-[(Z)-2-(3-pyridyl)vinylthio]-3-cephem-4-carboxylate (syn isomer)
NMR (DMSO-d$_6$, δ): 0.95 (3H, t, J=7 Hz), 1.35–2.0 (2H, m), 3.73–4.37 (4H, m), 5.28 (1H, d, J=4 Hz), 5.90 (1H, dd, J=4 Hz, 8 Hz), 6.67–6.87 (2H, m), 6.92 (1H, s), 7.0–7.63 (12H, m), 7.63–8.82 (3H, m), 9.68 (1H, d, J=8 Hz)

(53) 7-[2-(5-Amino-1,2,4-thiadiazol-3-yl)-2-methoxyiminoacetamido]-3-[(Z)-2-(1-methyl-3 -pyridinio)-vinylthio]-3-cephem-4-carboxylate (syn isomer)
IR (Nujol): 3260, 1765, 1660, 1610 cm$^{-1}$

(54) 7-[2-(5-Amino-1,2,4-thiadiazol-3-yl)-2-ethoxyiminoacetamido]-3-[(Z)-2-(1-methyl-3-pyridinio)vinylthio]-3-cephem-4-carboxylate (syn isomer)
IR (Nujol): 3300, 1770, 1670, 1610 cm$^{-1}$

(55) 7-[2-(22-Aminothiazol-4yl)-2-propoxyiminoacetamido]-3-[(Z)-2-(3-pyridyl)vinylthio]-3-cephem-4-carboxylic acid (syn isomer)
IR (Nujol): 3280, 3180, 1775, 1665 cm$^{-1}$

(56) 7-[2-(5-Amino-1,2,4-thiadiazol-3-yl)-2-cyclopenthyloxyiminoacetamido]-3-[(Z)-2-(3-pyridyl)vinylthio]-3-cephem-4-carboxylic acid (syn isomer)
IR (Nujol): 3270, 1770, 1670, 1615 cm$^{-1}$

(57) 7-[2-(5-Amino-1,2,4-thiadiazol-3yl)-2-(2-propynyloxyimino)acetamido]-3-[(Z)-2-(3-pyridyl)-vinylthio]-3-cephem-4-carboxylic acid (syn isomer)
IR (Nujol): 3270, 1770, 1670, 1615 cm$^{-1}$

(58) 1-Acetoxyethyl 7-[2-(2-aminothiazol-4-yl)-2-allyloxyiminoacetamido]-3-[(Z)-2-(3-pyridyl)vinylthio]-3-cephem-4-carboxylate (syn isomer)

IR (Nujol): 3300, 1760–1780, 1670, 1240, 1210, 1070 cm$^{-1}$

EXAMPLE 27

To a suspension of benzhydryl 7-formamido-3 -[(Z)-2-(3-pyridyl)vinylthio]-3-cephem-4-carboxylate (69.8 g) in methanol (350 ml) was added conc. hydrochloric acid (40.7 ml). The mixture was heated at 30°–35° C. for 2 hours. The mixture was poured into a mixture of ethyl acetate (2 l) and water (1 l) and adjusted to pH 6.5 with a saturated aqueous solution of sodium bicarbonate. The organic layer was separated, washed with water and saturated aqueous solution of sodium chloride in turn, dried over magnesium sulfate and concentrated in vacuo to a crystal. The crystal was washed with diethyl ether to give benzhydryl 7-amino-3-[(Z)-2-(3-pyridyl)-vinylthio]-3-cephem-4-carboxylate (52.3 g).

IR (Nujol): 1765, 1720, 1650 cm$^{-1}$

NMR (DMSO-d$_6$, δ): 3.70 and 4.13 (2H, ABq, J=18 Hz), 4.90 (1H, d, J=5 Hz), 5.11 (1H, d, J=5 Hz), 6.67 (1H, d, J=11 Hz), 6.83 (1H, d, J=11 Hz), 6.93 (1H, s), 7.17–7.62 (11H, m), 7.62–8.65 (3H, m)

EXAMPLE 28

The following compounds were obtained according to a similar manner to that of Example 27.

(1) Benzhydryl 7-amino-3-[(E)-2-(2-pyridyl)vinylthio]-3-cephem-4-carboxylate

IR (Nujol): 1775, 1740 cm$^{-1}$ (2) Benzhydryl 7-amino-3-[(Z)-2-(2-pyridyl) vinylthio]-3-cephem-4-carboxylate IR (Nujol): 1765, 1715, 1590, 1580 cm$^{-1}$ NMR (DMSO-d$_6$, δ): 3.67, 4.10 (2H, ABq, J=18 Hz), 4.83 (1H, d, J=4 Hz), 5.07 (1H, d, J=4 Hz), 6.63 (1H, d, J=10 Hz), 6.83 (1H, s), 6.87 (1H, d, J=10 Hz), 7.00–7.97 (13H, m), 8.67–8.50 (1H, m)

EXAMPLE 29

To a solution of 7-[2-(2-aminothiazol-4-yl)-2-allyloxyiminoacetamido]-3-[(Z)-2-(3-pyridyl)vinylthio]-3-cephem-4-carboxylic acid (syn isomer) (1.0 g) in N,N-dimethylformamide (20 ml) was added cesium carbonate (0.31 g). The mixture was stirred for 20 minutes at room temperature, and 1-bromoethyl acetate (0.96 g) was added dropwise thereto at 0°–3° C. After the mixture was stirred for 40 minutes, 1-bromoethyl acetate (0.3 g) was added thereto. After stirring for 1 hour, reaction mixture was poured into ethyl acetate (120 ml) and the insoluble material was filtered off. The filtrate was washed with water (120 ml×2), an aqueous solution of sodium bicarbonate (50 ml × 1) and a saturated aqueous solution of sodium chloride successively and dried over magnesium sulfate. The ethyl acetate was distilled off under reduced pressure, and the residue was pulverized with diisopropyl ether to give 1-acetoxyethyl 7-[2-(2-aminothiazol-4-yl)-2-allyloxyiminoacetamido]-3-[(Z)-2-(3-pyridyl) vinylthio]-3-cephem-4-carboxylate (syn isomer) (0.27 g).

IR (Nujol): 3300, 1760–1780, 1670, 1240, 1210, 1070 cm$^{-1}$

NMR (DMSO-d$_6$, δ): 1.47 (3H, d, J=6 Hz), 2.02 (3H, s), 3.97, (2H, d—d, J=18 Hz, 24 Hz), 4.62 (2H, d, J=5 Hz), 5.26 (1H, d, J=5 Hz), 5.0–5.43 (2H, m), 5.60–5.97 (2H, m), 6.73 (1H, s), 6.83 (2H, s), 6.93–7.30 (1H, m), 7.45 (1H, d—d, J=5 Hz, 9 Hz), 7.93 (1H, d—d, J=2 Hz), 8.50 (1H, d—d, J=2 Hz, 8 Hz), 8.60–8.77 (1H, m), 9.57 (1H, d, J=8 Hz)

EXAMPLE 30

The following compounds were obtained according to a similar manner to that of Example 29.

(1) Benzhydryl 7-amino-3-[(Z)-2-(3-pyridyl)vinylthio]-3-cephem-4-carboxylate

IR (Nujol): 1765, 1720, 1650 cm$^{-1}$ (2) Benzhydryl 7-[2-allyloxyimino-2-(5-amino-1,2,4-thiadiazol-3-yl)acetamido]-3-[(Z)-2-(3-pyridyl)vinylthio]-3-cephem-4-carboxylate (syn isomer)

IR (Nujol): 1760, 1730, 1660, 1605 cm$^{-1}$ (3) Benzhydryl 7-[2-(2-formamidothiazol-4-yl)-2-methoxyiminoacetamido]-3-[(Z)-2-(3-pyridyl)-vinylthio]-3-cephem-4-carboxylate (syn isomer)

IR (Nujol): 3250, 1770, 1705, 1680, 1650 cm$^{-1}$ (4) Benzhydryl 7-[2-(2-formamidothiazol-4-yl)-2-methoxyiminoacetamido]-3-[(Z)-2-(1-methyl-3-pyridinio)vinylthio]-3-cephem-4-carboxylate iodide (syn isomer)

IR (Nujol): 1775, 1720, 1640, 1540 cm$^{-1}$ (5) Benzhydryl 7-[2-(2-aminothiazol-4-yl)-2-methoxyiminoacetamido]-3-[(Z)-2-(3-pyridyl)-vinylthio]-3-cephem-4-carboxylate (syn isomer)

IR (Nujol): 1775, 1720, 1670, 1605, 1530 cm$^{-1}$ (6) Benzhydryl 7-[2-(2-aminothiazol-4-yl)-2-methoxyiminoacetamido]-3-[(Z)-2-(1-methyl-3-pyridinio)vinylthio]-3-cephem-4-carboxylate iodide (syn isomer)

IR (Nujol): 1770, 1710, 1660, 1620 cm$^{-1}$ (7) Benzhydryl 7-[2-allyloxyimino-2-(5-amino-1,2,4-thiadiazol-3-yl)acetamido]-3-[(Z)-2-(1-methyl-3-pyridinio)vinylthio]-3-cephem-4-carboxylate iodide (syn isomer)

IR (Nujol): 1775, 1720, 1650, 1600 cm$^{-1}$ (8) Benzhydryl 7-[2-(5-amino-1,2,4-thiadiazol-3-yl)-2-ethoxyiminoacetamido]-3-[(Z)-2-(3-pyridyl)-vinylthio]-3-cephem-4-carboxylate (syn isomer)

IR (Nujol): 3350, 3150, 1780, 1730, 1675, 1615 cm$^{-1}$ (9) Benzhydryl 7-[2-(5-amino-1,2,4-thiadiazol-3-yl)-2-methoxyiminoacetamido]-3-[(Z)-2-(3-pyridyl)-vinylthio]-3-cephem-4-carboxylate (syn isomer)

IR (Nujol): 1770, 1670, 1610, 1520 cm$^{-1}$

(10) Benzhydryl 7-[2-(5-amino-1,2,4-thiadiazol-3-yl)-2-(2-cyclopenten-1-yl)oxyiminoacetamido]-3-[(Z)-2-(3-pyridyl)vinylthio]-3-cephem-4-carboxylate (syn isomer)

IR (Nujol): 3300, 3150 1780, 1675, 1610, 1530, 1280, 1220 cm$^{-1}$

(11) Benzhydryl 7-[2-(5-amino-1,2,4-thiadiazol-3-yl)-2-carboxymethoxyiminoacetamido]-3-[(Z)-2-(3-pyridyl)vinylthio]-3-cephem-4-carboxylate (syn isomer)

IR (Nujol): 1770, 1730, 1670, 1610, 1520 cm$^{-1}$

(12) Benzhydryl 7-[D-N-(4-ethyl-2,3-dioxo-1-piperazinylcarbonyl)-2-(4-hydroxyphenyl)-glycinamido]-3-[(Z)-2-(3-pyridyl)vinylthio]-3-cephem-4-carboxylate IR (Nujol): 3250, 1780, 1705, 1670, 1605 cm$^{-1}$

(13) Benzhydryl 7-[2-(2-formamidothiazol-4-yl)-2-(2-propynyloxyimino)acetamido]-3-[(Z)-2-(3-pyridyl)vinylthio]-3-cephem-4-carboxylate (syn isomer)

IR (Nujol): 1780, 1680, 1550, 1280, 1225 cm$^{-1}$

(14) Benzhydryl 7-[2-allyloxyimino-2-(2-formamidothiazol-4-yl)acetamido]-3-[(Z)-2-(3-pyridyl)vinylthio]-3-cephem-4-carboxylate (syn isomer)

IR (Nujol): 1780, 1690, 1670, 1550, 1280, 1220 cm$^{-1}$

(15) Benzhydryl 7-[2-benzhydryloxycarbonylmethoxyimino-2-(2-formamidothiazol-4-yl)acetamido]-3-[(Z)-2-(3-pyridyl)vinylthio-3-cephem-4-carboxylate (syn isomer)

IR (Nujol): 1780, 1730, 1680, 1540 cm$^{-1}$

(16) Benzhydryl 7-[2-ethoxyimino-2-(2-formamidothiazol-4-yl)acetamido]-3-[(Z)-2-(3-pyridyl)vinylthio]-3-cephem-4-carboxylate (syn isomer)

IR (Nujol: 1780, 1680, 1540 cm$^{-1}$

(17) Benzhydryl 7-[2-allyloxyimino-2-(5-amino-1,2,4-thiadiazol-3-yl)acetamido]-[(E)-2-(2-pyridyl)-vinylthio]-3-cephem-4-carboxylate (syn isomer) IR (Nujol): 1775, 1675, 1610, 1520 cm$^{-1}$

(18) Benzhydryl 7-[2-allyloxyimino-2-(5-amino-1,2,4-thiadiazol-3-yl)acetamido]-3-[(Z)-2-(2-pyridyl)vinylthio]-3-cephem-4-carboxylate (syn isomer)

IR (Nujol): 1780, 1680, 1620, 1600, 1530 cm$^{-1}$

(19) Benzhydryl 7-[2-allyloxyimino-2-(5-amino-1,2,4-thiadiazol-3-yl)acetamido]-3-[(Z)-2-cyanovinylthio]-3-cephem-4-carboxylate (syn isomer)

IR (Nujol): 3300, 2210, 1780, 1675, 1610 cm$^{-1}$ (20) Benzhydryl 7-[2-benzhydryloxycarbonylmethoxyimino-2-(2-formamidothiazol-4-yl)acetamido]-3-[(Z)-2-(1-methyl-3-pyridinio)vinylthio]-3-cephem-4-carboxylate iodide (syn isomer)

IR (Nujol): 3350, 1760, 1735, 1660 cm$^{-1}$

(21) Benzhydryl 7-[2-ethoxyimino-2-(2-formamidothiazol-4-yl)acetamido]-3-[(Z)-2-(1-methyl-3-pyridinio)vinylthio]-3-cephem-4-carboxylate iodide (syn isomer)

IR (Nujol): 1780, 1720, 1650 cm$^{-1}$

(22) Benzhydryl 7-[2-(2-aminothiazol-4-yl)-2-(2-propynyloxyimino)acetamido]-3-[(Z)-2-(3-pyridyl)vinylthio]-3-cephem-4-carboxylate (syn isomer)

IR (Nujol): 1770, 1670, 1530, 1270, 1215 cm$^{-1}$

(23) Benzhydryl 7-[2-allyloxyimino-2-(2-aminothiazol-4-yl)acetamido]-3-[(Z)-2-(3-pyridyl)vinylthio]-3-cephem-4-carboxylate (syn isomer).

IR (Nujol): 3300, 1780, 1670, 1610, 1535, 1280, 1220 cm$^{-1}$

(24) Benzhydryl 7-[2-(2-aminothiazol-4-yl)-2-benzhydryloxycarbonylmethoxyiminoacetamido]-3-[(Z)-2-(1-methyl-3-pyridinio)vinylthio]-3-cephem-4-carboxylate iodide (syn isomer)

NMR (DMSO-d$_6$, δ): 3.6–4.2 (2H, m), 4.3 (3H, s), 4.9 (2H, s), 5.28 (1H, d, J=5 Hz), 5.9 (1H, dd, J=8 Hz, 5 Hz), 6.75 (1H, d, J=10 Hz), 6.87 (3H, s), 7.03 (1H, d, J=10 Hz), 7.00–9.05 (24H, m), 9.83 (1H, d, J=8 Hz)

(25) Benzhydryl 7-[2-(2-aminothiazol-4-yl)-2-ethoxyiminoacetamido]-3-[(Z)-2-(3-pyridyl)vinylthio]-3-cephem-4-carboxylate (syn isomer)

IR (Nujol): 1780, 1720, 1675 cm$^{-1}$

(26) Benzhydryl 7-[2-(2-aminothiazol-4-yl)-2-ethoxyiminoacetamido]-3-[(Z)-2-(1-methyl-3-pyridino)vinylthio]-3-cephem-4-carboxylate iodide (syn isomer)

IR (Nujol): 1770, 1670, 1625 cm$^{-1}$

(27) Benzhydryl 7-formamido-3-[(Z)-2-(2-pyridyl)vinylthio]-3-cephem-4-carboxylate IR (Nujol): 1770, 1690–1660, 1590, 1580 cm$^{-1}$

(28) Benzhydryl 7-formamido-3-[(E)-2-(2-pyridyl)vinylthio]-3-cephem-4-carboxylate IR (Nujol): 1780, 1690, 1660, 1600, 1580 cm$^{-1}$

(29) Benzhydryl 7-formamido-3-[(Z)-2-cyanovinylthio]-3-cephem-4-carboxylate

IR (Nujol): 3300, 2210, 1780, 1730, 1680 cm$^{-1}$

(30) Benzhydryl 7-formamido-3-[(Z)-2-(3-pyridyl)vinylthio]-3-cephem-4-carboxylate IR (Nujol): 1785, 1705, 1690, 1560, 1220 cm$^{-1}$

(31) Benzhydryl 7-amino-3-[(E)-2-(2-pyridyl)vinylthio]-3-cephem-4-carboxylate

IR (Nujol): 1775, 1740 cm$^{-1}$

(32) Benzhydryl 7-amino-3-[(Z)-2-(2-pyridyl)vinylthio]-3-cephem-4-carboxylate

IR (Nujol): 1765, 1715, 1590, 1580 cm$^{-1}$

(33) Benzhydryl 7-[2-(2-formamidothiazol-4-yl)-2-propoxyiminoacetamido]-3-[(Z)-2-(3-pyridyl)vinylthio]-3-cephem-4-carboxylate (syn isomer)

NMR (DMSO-d$_6$, δ): 0.95 (3H, t, J=7 Hz), 1.35–2.0 (2H, m), 3.73–4.37 (4H, m), 5.28 (1H, d, J=4 Hz), 5.90 (1H, dd, J=4 Hz, 8 Hz), 6.67–6.87 (2H, m), 6.92 (1H, s), 7.0–7.63 (12H, m), 7.63–8.83 (3H, m), 8.5 (1H, s), 9.68 (1H, d, J=8 Hz)

(34) Benzhydryl 7-[2-(5-amino-1,2,4-thiadiazol-3-yl)-2-cyclopentyloxyiminoacetamido]-3-[(Z)-2-(3-pyridyl)vinylthio]-3-cephem-4-carboxylate (syn isomer)

NMR (DMSO-d$_6$, δ): 1.27–2.07 (8H, m), 3.73–4.17 (2H, m), 4.53–4.90 (1H, m), 5.23 (1H, d, J=5 Hz), 5.90 (1H, dd, J=5 Hz, 9 Hz), 6.50–7.05 (2H, m), 6.90 (1H, s), 7.05–7.90 (13H, m), 7.90–8.80 (3H, m), 8.08 (1H, s), 9.57 (1H, d, J=9 Hz),

(35) Benzhydryl 7-[2-(5-amino-1,2,4-thiadiazol-3-yl)-2-(2-propynyloxyimino)acetamido]-3-[(Z)-2-(3-pyridyl)vinylthio]-3-cephem-4-carboxylate (syn isomer)

NMR (DMSO-d$_6$, δ): 3.50–4.05 (2H, m), 3.31 (1H, s), 5.31 (1H, d, J=4 Hz), 5.97 (1H, dd, J=5 Hz, 8 Hz), 6.79 (2H, dd, J=4 Hz, 10 Hz), 6.96 (1H, s), 7.03–7.64 (1H, m), 7.62–7.99 (1H, m), 7.97–8.58 (2H, m), 8.56–8.75 (2H, m), 9.79 (1H, d, J=8 Hz)

(36) Benzhydryl 7-[2-(5-amino-1,2,4-thiadiazol-3-yl)-2-methoxyiminoacetamido]-3-[(Z)-2-(1-methyl-3-pyridinio)vinylthio]-3-cephem-4-carboxylate iodide (syn isomer)

NMR (DMSO-d$_6$, δ): 3.90 (3H, s), 4.03 (3H, s), 3.57–4.27 (2H, m), 5.25 (1H, d, J=5 Hz), 5.92 (1H, dd, J=5 Hz, 9 Hz), 6.75 (1H, d, J=11 Hz), 6.87 (1H, s), 7.07–7.62 (11H, m), 7.93–9.06 (6H, m), 9.58 (1H, d, J=9 Hz)

(37) Benzhydryl 7-[2-(2-aminothiazol-4-yl)-2-propoxyiminoacetamido]-3-[(Z)-2-(3-pyridyl)vinylthio]-3-cephem-4-carboxylate (syn isomer)

NMR (DMSO-d$_6$, δ): 0.95 (3H, t, J=7 Hz), 1.35–2.0 (2H, m), 3.73–4.37 (4H, m), 5.28 (1H, d, J=4 Hz), 5.90 (1H, dd, J=4 Hz, 8 Hz), 6.67–6.87 (2H, m), 6.92 (1H, s), 7.0–7.63 (12H, m), 7.63–8.82 (3H, m), 9.68 (1H, d, J=8 Hz)

Preparation 19

The following compound was obtained according to a similar manner to that of Preparation 3.

2-Methyl-5-[(Z)-2-(tritylthio)vinyl]pyridine

IR (Nujol): 1590, 1490, 1445 cm$^{-1}$

NMR (DMSO-d$_6$, δ): 2.43–2.60 (3H, hidden), 5.93, 6.40 (2H, ABq, J=10 Hz), 6.93–7.50 (16H, m), 7.80 (1H, dd, J=3 Hz, 7 Hz), 8.50 (1H, d, J=3 Hz)

Preparation 20

The following compound was obtained according to a similar manner to that of Preparation 5. [(Z)-2-(2-Methyl-5-pyridyl)vinylthio]silver IR (Nujol): 1570, 1540 cm$^{-1}$ Preparation 21

To a solution of N,N-diisopropylamine (3.39 ml) in anhydrous tetrahydrofuran (80 ml) was added 1.55M n-butyllithium in n-hexane at 60° C. The mixture was stirred for 30 minutes at 0° C. To the solution was added a solution of 2-ethoxy-1,3-oxathiolane (3 ml) in tetrahydrofuran (5 ml) at −60~−70° C. after the mixture was stirred for 30 minutes at −65° C., the mixture was poured into a solution of silver nitrate (8.46 g) in a mixture of water (20 ml) and methanol (80 ml) under ice-cooling, stirred for 30 minutes and adjusted to pH 6.5 with dilute hydrochloric acid. The precipitate was collected by filtration, washed with water, methanol and diethyl ether successively, and dried to give vinylthiosilver (7.41 g).

Preparation 22

2-Chloroethanol (0.83 ml) was allowed to react with sodium azide in an aqueous solution of sodium hydroxide (1.25 N, 30 ml) for 3.5 hours at 50° C. and sodium sulfate was added thereto. The mixture was extracted with methylene chloride. The extracts were dried over anhydrous sodium sulfate and concentrated to give 2-azidoethanol (580 mg).

IR (Film): 2100 cm$^{-1}$
NMR (CDCl$_3$, δ): 2.7 (1H, s), 3.4 (2H, m), 3.75 (2H, m)

Preparation 23

To a solution of 2-azidoethanol (0.9 g) in methylene chloride (25 ml) was added 2,6-lutidine (2.8 ml). After this solution was cooled to −78° C., trifluoromethanesulfonic anhydride (2 ml) was added dropwise thereto. The solution was stirred at −40~−30° C. for 3 hours and washed with water. The organic layer was separated, dried over anhydrous sodium sulfate and concentrated to give 2-azidoethyl trifluoromethanesulfonate (2.4 g).

IR (Film): 2100, 1410 cm$^{-1}$
NMR (CDCl$_3$, δ): 3.63 (2H, t, J=5 Hz), 4.57 (2H, t, J=5 Hz)

EXAMPLE 31

To a solution of benzhydryl 7-amino-3-[(Z)-2-(3-pyridyl)vinylthio]-3-cephem-4-carboxylate (1.50 g) and 2-(2-tritylaminothiazol-4-yl)-3-hydroxypropionic acid (1.42 g) in tetrahydrofuran was added N,N'-dicyclohexyl-carbodiimide (925 mg) under ice-cooling. The resultant mixture was stirred for 1 hour at the same temperature and stirred for 2 hours at ambient temperature. The resultant precipitate was filtered off. To the filtrate was added ethyl acetate (100 ml) and the organic layer was separated, washed with a saturated aqueous solution of sodium chloride (50 ml) and dried over magnesium sulfate. The solvent was distilled off and the residue was subjected to column chromatography on silica gel (120 g) and eluted with a mixture of ethyl acetate and diisopropyl ether (3:1). The fractions containing the object compound were combined and concentrated in vacuo to give benzhydryl 7-[2-(2-tritylaminothiazol-4-yl)-3-hydroxypropionamido]-3-[(Z)-2-(3-pyridyl)vinylthio]-3-cephem-4-carboxylate (1.10 g).

IR (Nujol): 3300, 1780, 1730, 1670, 1520, 1495, 1280, 1220 cm$^{-1}$
NMR (DMSO-d$_6$+D$_2$O, δ): 3.4–4.2 (5H, m), 5.17 (1H, d, J=5 Hz), 5.62 (1H, d, J=5 Hz), 6.22 and 6.25 (1H, s), 6.74 (2H, s), 6.88 (1H, s), 7.0–7.6 (26H, m), 7.6–7.9 (1H, m), 8.4–8.7 (2H, m)

EXAMPLE 32

The following compounds were obtained according to similar manners to those of Examples 1-5 and 31.

(1) 7-[2-Methoxyimino-2-(5-amino-1,2,4-thiadiazol-3-yl)acetamido]-3-[(Z)-2-(1,2-dimethyl-5-pyridinio)-vinylthio]-3-cephem-4-carboxylate (syn isomer).
mp: 190°-200° C. (dec.)
IR (Nujol): 3400−3150, 3300, 1760, 1670, 1600, 1520, 1340 cm$^{-1}$ (2) Benzhydryl 7-[2-(2-formamidothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer).
IR (Nujol): 2125, 2100, 1775, 1680, 1640 cm$^{-1}$ (3) Benzhydryl 7-[2-(2-aminothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer).
IR (Nujol): 2130, 2100, 1780, 1670, 1630 cm$^{-1}$ (4) Benzhydryl 7-[2-(2-aminothiazol-4-yl)-2-methoxyiminoacetamido]-3-[(Z)-2-(1,2-dimethyl-5-pyridinio)-vinylthio]-3-cephem-4-carboxylate iodide hydrochloride (syn isomer).
IR (Nujol): 3350, 3150, 1780, 1670, 1630, 1565, 1545, 1275, 1220 cm$^{-1}$ (5) 7-[2-(2-Aminothiazol-4-yl)-2-carboxymethoxyiminoacetamido]-3-vinylthio-3-cephem-4-carboxylic acid (syn isomer).
mp: 192° C. (dec.)
IR (Nujol): 1760, 1660, 1630 cm$^{-1}$ (6) 7-[2-(2-Aminothiazol-4-yl)-2-ethoxyiminoacetamido]-3-[(Z)-2-(1,2-dimethyl-5-pyridinio)vinylthio]-3-cephem-4-carboxylate (anti isomer).
IR (Nujol): 1760, 1670, 1610, 1520 cm$^{-1}$ (7) 7-[2-(2-Aminothiazol-4-yl)-2-methoxyiminoacetamido]-3-[(Z)-2-{1-(2-azidoethyl)-3-pyridinio}-vinylthio]-3-cephem-4-carboxylate (syn isomer).
IR (Nujol): 2150, 2120, 1770, 1670, 1610 cm$^{-1}$ (8) 7-[2-Carboxymethoxyimino-2-{2-(2,2,2-trifluoroacetamido)thiazol-4-yl}acetamido]-3-vinylthio-3-cephem-4-carboxylic acid (syn isomer).
IR (Nujol): 1750, 1710, 1655, 1530 cm$^{-1}$ (9) 7-[2-((Z)-2-Cyanovinylthio)acetamido]-3-vinylthio-3-cephem-4-carboxylic acid.
mp: 145° C. (dec.)
IR (Nujol): 3270, 2210, 1750, 1710, 1660, 1530 cm$^{-1}$

(10) p-Nitrobenzyl 7-[2-(5-amino-1,2,4-thiadiazol-3-yl)-2-ethoxyiminoacetamido]-3-vinylthio-3-cephem-4-carboxylate (syn isomer).
IR (Nujol): 1770, 1680, 1615, 1525, 1455 cm$^{-1}$

(11) Benzhydryl 7-formamido-3-[(Z)-2-(2-methyl-5-pyridyl)vinylthio]-3-cephem-4-carboxylate.
IR (Nujol): 3150, 1780, 1710, 1690, 1230, 1220 cm$^{-1}$

(12) 7-[2-(5-amino-1,2,4-thiadiazol-3-yl)-2-ethoxyiminoacetamido]-3-vinylthio-3-cephem-4-carboxylic acid (syn isomer).
mp: 145° C. (dec.)
IR (Nujol): 1765, 1670, 1525 cm$^{-1}$

(13) p-Nitrobenzyl 7-(2-phenylacetamido)-3-vinylthio-3-cephem-4-carboxylate.
IR (Nujol): 3280, 1970, 1705, 1665, 1540, 1520 cm$^{-1}$

(14) p-Nitrobenzyl 7-[2-(p-nitrobenzyloxycarbonylmethoxyimino)-2-{2-(2,2,2-trifluoroacetamido)-thiazol-4-yl}acetamido]-3-vinylthio-3-cephem-4-carboxylate (syn isomer).
IR (Nujol): 1780, 1720, 1660, 1610, 1520, 1345 cm$^{-1}$
NMR (DMSO-d$_6$, δ): 3.57, 3.90 (2H, AB$_q$, J=18 Hz), 4.82 (2H, s), 5.20 (1H, d, J=5 Hz), 5.27 (2H, s), 5.33 (2H, s), 5.42 (1H, d, J=16 Hz), 5.50 (1H, d, J=10 Hz), 5.80 (1H, dd, J=5 Hz, 8 Hz), 6.60 (1H, dd, J=10 Hz, 16 Hz), 7.49 (1H, s), 7.52 (2H, d, J=9 Hz), 7.58 (2H, d, J=9 Hz), 8.03 (2H, d, J=9 Hz), 8.11 (2H, d, J=9 Hz), 9.68 (1H, d, J=8 Hz)

(15) p-Nitrobenzyl 7-[2-((Z)-2-cyanovinylthio)-acetamido]-3-vinylthio-3-cephem-4-carboxylate.
IR (Nujol): 3290, 2210, 1760, 1700, 1640, 1515, 1350 cm$^{-1}$
NMR (DMSO-d$_6$, δ): 3.63, 4.03 (2H, AB$_q$, J=18 Hz), 3.77 (2H, s), 5.27 (1H, d, J=5 Hz), 5.43 (2H, s), 5.53 (1H, d, J=16 Hz), 5.60 (1H, d, J=9 Hz), 5.71 (1H, d, J=10 Hz), 5.77 (1H, dd, J=5 Hz, J=8 Hz), 6.73 (1H, dd, J=9

Hz, J=16 Hz), 7.67 (1H, d, J=10 Hz), 7.70 (2H, d, J=9 Hz), 8.27 (2H, d, J=9 Hz), 9.27 (1H, d, J=8 Hz)

(16) 7-[2-(5-Amino-1,2,4-thiadiazol-3-yl)-2-ethoxyiminoacetamido]-3-[(Z)-2-(1,2-dimethyl-5-pyridinio)-vinylthio]-3-cephem-4-carboxylate (syn isomer).

mp: 185°~195° C. (dec.)

IR (Nujol): 3450–3150, 3300, 1775, 1680, 1615, 1530, 1350 cm$^{-1}$

(17) 7-[2-(5-Amino-1,2,4-thiadiazol-3-yl)-2-methoxyiminoacetamido]-3-[(Z)-2-(2-methyl-5-pyridyl)-vinylthio]-3-cephem-4-carboxylic acid (syn isomer).

mp: 179°~185° C. (dec.)

IR (Nujol): 3300, 3200, 1775, 1680, 1620, 1530, 1350 cm$^{-1}$

(18) Benzhydryl 7-[2-(5-amino-1,2,4-thiadiazol-3-yl)-2-methoxyiminoacetamido]-3-[(Z)-2-(2-methyl-5-pyridyl)-vinylthio]-3-cephem-4-carboxylate (syn isomer).

IR (Nujol): 3300, 3150, 1780, 1670, 1610, 1600, 1530, 1280, 1220 cm$^{-1}$

NMR (DMSO-d$_6$, δ): 2.49 (3H, s), 3.6–4.4 (2H, m), 3.93 (3H, s), 5.28 (1H, d, J=5 Hz), 5.95 (1H, dd, J=5 Hz, 8 Hz), 6.72 (2H, s), 6.94 (1H, s), 7.1–7.5 (11H, m), 7.6–7.9 (1H, m), 8.13 (2H, bs), 8.5 (1H, m), 9.68 (1H, d, J=8 Hz)

(19) 7-[2-(2-Aminothiazol-4-yl)-2-methoxyiminoacetamido]-3-[(Z)-2-(1,2-dimethyl-5-pyridinio)-vinylthio]-3-cephem-4-carboxylate (syn isomer).

mp: 190°–195° C. (dec.)

IR (Nujol): 3300, 3200, 1770, 1660, 1610, 1530, 1340 cm$^{-1}$

(20) Benzhydryl 7-[2-(2-formamidothiazol-4-yl)-2-methoxyiminoacetamido]-3-[(Z)-2-(1,2-dimethyl-5-pyridinio)vinylthio]-3-cephem-4-carboxylate iodide (syn isomer)

IR (Nujol): 3400, 3150, 1780, 1660, 1540, 1280, 1220 cm$^{-1}$

(21) 7-[2-(2-Aminothiazol-4-yl)-2-methoxyiminoacetamido]-3-[(Z)-2-(2-methyl-5-pyridyl)vinylthio]-3-cephem-4-carboxylic acid (syn isomer).

mp: 177°~182° C. (dec.)

IR (Nujol): 3300, 3200, 1770, 1670, 1620, 1535, 1350 cm$^{-1}$

(22) Benzhydryl 7-[2-(2-aminothiazol-4-yl)-2-methoxyiminoacetamido]-3-[(Z)-2-(2-methyl-5-pyridyl)-vinylthio]-3-cephem-4-carboxylate (syn isomer).

IR (Nujol): 3300, 3150, 1780, 1670, 1610, 1535, 1490, 1280, 1220 cm$^{-1}$

(23) Benzhydryl 7-[2-(2-formamidothiazol-4-yl)-2-methoxyiminoacetamido]-3-[(Z)-2-(2-methyl-5-pyridyl)-vinylthio]-3-cephem-4-carboxylate (syn isomer).

IR (Nujol): 3250, 3150, 1780, 1690, 1650, 1550, 1280, 1230 cm$^{-1}$

NMR (DMSO-d$_6$, δ): 2.50 (3H, s), 3.77 and 4.17 (2H, ABq, J=18 Hz), 3.92 (3H, s), 5.32 (1H, d, J=5 Hz), 5.95 (1H, dd, J=5 Hz, 8 Hz), 6.74 (2H, s), 6.95 (1H, s), 7.1–7.8 (13H, m), 8.4–8.7 (1H, m), 8.55 (1H, s), 9.77 (1H, d, J=8 Hz)

(24) 7-[2-(5-Amino-1,2,4-thiadiazol-3-yl)-2-ethoxyiminoacetamido]-3-[(Z)-2-(2-methyl-5-pyridyl)-vinylthio]-3-cephem-4-carboxylic acid (syn isomer).

mp: 175°–180° C. (dec.)

IR (Nujol): 3300, 3150, 1770, 1670, 1610, 1530, 1290 cm$^{-1}$

(25) Benzhydryl 7-[2-(5-amino-1,2,4-thiadiazol-3-yl)-2-ethoxyiminoacetamido]-3-[(Z)-2-(2-methyl-5-pyridyl)vinylthio]-3-cephem-4-carboxylate (syn isomer).

IR (Nujol): 3300, 3150, 1780, 1670, 1610, 1530, 1280, 1220 cm$^{-1}$

NMR (DMSO-d$_6$, δ): 1.26 (3H, t, J=7 Hz), 2.53 (3H, s), 3.73 and 4.12 (2H, ABq, J=18 Hz), 4.20 (2H, q, J=7 Hz), 5.25 (1H, d, J=5 Hz), 5.92 (1H, dd, J=5 Hz and 8 Hz), 6.70 (2H, s), 6.90 (1H, s), 7.1–7.8 (12H, m), 8.09 (2H, bs), 8.4–8.5 (1H, m), 9.60 (1H, d, J=8 Hz)

(26) 7-[2-(5-Amino-1,2,4-thiadiazol-3-yl)-2-carboxymethoxyiminoacetamido]-3-[(Z)-2-(1-methyl-3-pyridinio)vinylthio]-3-cephem-4-carboxylate (syn isomer).

mp: 165°–170° C. (dec.)

IR (Nujol): 3400–3100, 1760, 1630, 1600, 1510, 1240 cm$^{-1}$

(27) Benzhydryl 7-[2-(5-amino-1,2,4-thiadiazol-3-yl)-2-carboxymethoxyiminoacetamido]-3-[(Z)-2-(1-methyl-3-pyridinio)vinylthio]-3-cephem-4-carboxylate iodide (syn isomer).

IR (Nujol): 3250, 3150, 1780, 1730, 1655, 1525, 1285, 1225 cm$^{-1}$

(28) 7-[2-(5-Amino-1,2,4-thiadiazol-3-yl)-2-(2-cyclopenten-1-yl)oxyiminoacetamido]-3-[(Z)-2-(3-pyridyl)-vinylthio]-3-cephem-4-carboxylic acid (syn isomer).

mp: 90°–100° C. (dec.)

IR (Nujol): 3400–3100, 1770, 1660, 1525 cm$^{-1}$

NMR (DMSO-d$_6$, δ): 1.7–2.6 (4H, m), 3.0–4.3 (2H, m), 5.2–5.6 (1H, m), 5.21 (1H, d, J=5 Hz), 5.6–6.0 (2H, m), 6.0–6.3 (1H, m), 6.78 (2H, s), 7.3–7.6 (1H, m), 7.7–8.0 (1H, m), 8.07 (2H, bs), 8.4 (1H, m), 8.6 (1H, m), 9.50 (1H, d, J=8 Hz)

(29) 7-[2-(2-Aminothiazol-4-yl)-3-hydroxypropionamido]-3-[(Z)-2-(3-pyridyl)vinylthio]-3-cephem-4-carboxylic acid.

mp: 100°–110° C. (dec.)

IR (Nujol): 3200, 1770, 1670–1520, 1600, 1340, 1250 cm$^{-1}$

(30) 7-(2-Phenylacetamido)-3-vinylthio-3-cephem-4-carboxylic acid.

IR (Nujol): 3300, 1780, 1690, 1630, 1520, 1360, 1230 cm$^{-1}$

(31) 7-[2-(2-Aminothiazol-4-yl)-2-methoxyiminoacetamido]-3-vinylthio-3-cephem-4-carboxylic acid (syn isomer).

mp: 195°–205° C. (dec.)

IR (Nujol): 3200, 1770, 1660, 1530 cm$^{-1}$

(32) 7-[2-Methoxyimino-2-{2-(2,2,2-trifluoroacetamido)thiazol-4-yl}acetamido]-3-vinylthio-3-cephem-4-carboxylic acid (syn isomer).

IR (Nujol): 3200, 1775, 1720, 1655, 1520, 1265, 1235, 1210 cm$^{-1}$

(33) p-Nitrobenzyl 7-[2-methoxyimino-2-{2-(2,2,2-trifluoroacetamido)thiazol-4-yl}acetamido]-3-vinylthio-3-cephem-4-carboxylate (syn isomer).

IR (Nujol): 3230, 1775, 1725, 1700, 1655, 1520, 1515, 1350, 1260, 1215 cm$^{-1}$ NMR (DMSO-d$_6$, δ): 3.58 and 3.90 (2H, ABq, J=18 Hz), 3.83 (3H, s), 5.17 (1H, d, J=5 Hz), 5.31 (2H, s), 5.38 (1H, d, J=16 Hz), 5.47 (1H, d, J=9 Hz), 5.75 (1H, dd, J=5 Hz and 8 Hz), 6.57 (1H, dd, J=9 Hz, and 16 Hz), 7.35 (1H, s), 7.52 (2H, d, J=8 Hz), 8.07 (2H, d, J=8 Hz), 8.57 (1H, d, J=8 Hz)

(34) Benzhydryl 7-[2-allyloxyimino-2-(2-formamidothiazol-4-yl)acetamido]-3-[(Z)-2-(1,2-dimethyl-5-pyridino)vinylthio]-3-cephem-4-carboxylate iodide (syn isomer).

IR (Nujol): 1780, 1670, 1530 cm$^{-1}$

(35) Benzhydryl 7-[2-allyloxyimino-2-(2-aminothiazol-4-yl)acetamido]-3[(Z)-2-(1,2-dimethyl-5-pyridinio)vinylthio]-3-cephem-4-carboxylate iodide (syn isomer).

IR (Nujol): 1780, 1670, 1630, 1520 cm$^{-1}$

(36) 7-[2-Allyloxyimino-2-(2-aminothiazol-4-yl)-acetamido]-3-[(Z)-2-(1,2-dimethyl-5-pyridinio)vinylthio]-3-cephem-4-carboxylate (syn isomer).

IR (Nujol): 1770, 1670, 1610, 1520 cm$^{-1}$

(37) Benzhydryl 7-[2-(2-formamidothiazol-4-yl)-2-ethoxyiminoacetamido]-3-[(Z)-2-(1,2-dimethyl-5-pyridinio)vinylthio]-3-cephem-4-carboxylate iodide (syn isomer).

NMR (DMSO-d$_6$, δ): 1.3 (3H, t, J=7 Hz), 4.18 (3H, s), 5.28 (1H, d, J=5 Hz), 5.90 (1H, dd, J=5 Hz, 8 Hz), 6.70, 7.05 (2H, ABq, J=11 Hz), 6.83 (1H, s), 7.05–7.60 (11H, m), 7.90 (1H, d, J=8 Hz), 8.21 (1H, d, J=8 Hz), 8.40 (1H, s), 8.85 (1H, s), 9.60 (1H, d, J=8 Hz)

(38) Benzhydryl 7-[2-(2-aminothiazol-4-yl)-2-ethoxyiminoacetamido]-3-[(Z)-2-(1,2-dimethyl-5-pyridinio)-vinylthio]-3-cephem-4-carboxylate iodide (syn isomer).

IR (Nujol): 1780, 1670, 1620, 1520 cm$^{-1}$

(39) 7-[2-(2-Aminothiazol-4-yl)-2-ethoxyiminoacetamido]-3-[(Z)-2-(1,2-dimethyl-5-pyridinio)-vinylthio]-3-cephem-4-carboxylate (syn isomer).

IR (Nujol): 1770, 1660, 1600, 1520 cm$^{-1}$

(40) Benzhydryl 7-[2-allyloxyimino-2-(5-amino-1,2,4-thiadiazol-3-yl)acetamido]-3-[(Z)-2-(2-methyl-5-pyridyl)vinylthio]-3-cephem-4-carboxylate (syn isomer).

IR (Nujol): 1770, 1670, 1600, 1520 cm$^{-1}$

NMR (DMSO-d$_6$, δ): 4.65 (2H, d, J=5 Hz), 5.1–5.5 (3H, m), 5.7–6.1 (2H, m), 6.7 (2H, s), 6.87 (1H, s), 7.1–7.5 (11H, m), 7.65 (1H, dd, J=3 Hz, 8 Hz), 8.05 (2H, s), 8.40 (1H, d, J=3 Hz), 9.57 (1H, d, J=8 Hz)

(41) 7-[2-Allyloxyimino-2-(5-amino-1,2,4-thiadiazol-3-yl)acetamido]-3-[(Z)-2-(2-methyl-5-pyridyl)vinylthio]-3-cephem-4-carboxylic acid (syn isomer).

IR (Nujol): 1770 cm$^{-1}$

(42) Benzhydryl 7-[2-allyloxyimino-2-(2-formamidothiazol-4-yl)acetamido]-3-[(Z)-2-(2-methyl-5-pyridyl)-vinylthio]-3-cephem-4-carboxylate (syn isomer).

IR (Nujol): 1780, 1690, 1650, 1540 cm$^{-1}$

NMR (DMSO-d$_6$, δ): 3.93, 4.10 (2H, ABq, J=30 Hz), 4.63 (2H, d, J=5 Hz), 5.10–5.50 (3H, m), 5.70–6.20 (2H, m), 6.67 (2H, s), 6.87 (1H, s), 7.1–7.5 (12H, m), 7.60 (1H, dd, J=3 Hz, 8 Hz), 8.37 (1H, d, J=3 Hz), 8.43 (1H, s), 9.65 (1H, d, J=8 Hz)

(43) Benzhydryl 7-[2-allyloxyimino-2-(2-aminothiazol-4-yl)acetamido]-3-[(Z)-2-(2-methyl-5-pyridyl)-vinylthio]-3-cephem-4-carboxylate (syn isomer).

IR (Nujol): 1780, 1670, 1610, 1530 cm$^{-1}$

(44) 7-[2-Allyloxyimino-2-(2-aminothiazol-4-yl)-acetamido]-3-[(Z)-2-(2-methyl-5-pyridyl)vinylthio]-3-cephem-4-carboxylic acid (syn isomer).

IR (Nujol): 1770, 1660, 1530 cm$^{-1}$

(45) Benzhydryl 7-[2-ethoxyimino-2-(2-formamidothiazol-4-yl)acetamido]-3-[(Z)-2-(2-methyl-5-pyridyl)-vinylthio]-3-cephem-4-carboxylate (syn isomer).

IR (Nujol): 1780, 1680, 1540 cm$^{-1}$

NMR (DMSO-d$_6$, δ): 1.23 (3H, t, J=6 Hz), 4.10 (2H, q, J=6 Hz, 13 Hz), 5.20 (1H, d, J=5 Hz), 5.83 (1H, m), 6.6–6.9 (3H, m), 7.0–7.4 (12H, m), 7.78 (1H, dd, J=2 Hz, 8 Hz), 8.3–8.5 (2H, m), 9.53 (1H, d, J=8 Hz)

(46) Benzhydryl 7-[2-(2-aminothiazol-4-yl)-2-ethoxyiminoacetamido]-3-[(Z)-2-(2-methyl-5-pyridyl)-vinylthio]-3-cephem-4-carboxylate (syn isomer).

IR (Nujol): 1780, 1670, 1610, 1520 cm$^{-1}$

(47) 7-[2-(2-Aminothiazol-4-yl)-2-ethoxyiminoacetamido]-3-[(Z)-2-(2-methyl-5-pyridyl)vinylthio]-3-cephem-4-carboxylic acid (syn isomer).

IR (Nujol): 1760, 1660, 1600, 1530 cm$^{-1}$

EXAMPLE 33

To a solution of 7-[2-(5-amino-1,2,4-thiadiazol-3-yl)-2-methoxyiminoacetamido]-3-[(Z)-2-(2-methyl-5-pyridyl)vinylthio]-3-cephem-4-carboxylic acid (syn isomer) (1.42 g) in N,N-dimethylformamide (7.1 ml) was added methyl iodide (1.4 ml) at ambient temperature and the mixture was stirred at the same temperature for 2 hours. The reaction mixture was poured into acetone (150 ml) to give a precipitate, which was collected by filtration and dried to give a powder. The powder was dissolved in a mixture of tetrahydrofuran (50 ml) and water (30 ml). The mixture was adjusted to pH 6.5–7.0 with an aqueous solution of sodium carbonate. After the mixture was washed with ethyl acetate (100 ml), the aqueous solution was subjected to column chromatography on macroporous non-ionic adsorption resin "Diaion HP-20" (40 ml), After the column was washed with water, the elution was carried out with 10% aqueous solution of isopropyl alcohol. The eluates containing the object compound were collected, evaporated to remove isopropyl alcohol under reduced pressure and the residue was lyophilized to give 7-[2-(5-amino-1,2,4-thiadiazol-3-yl)-2-methoxyiminoacetamido]-3-[(Z)-2-(1,2-dimethyl-5-pyridinio)vinylthio]-3-cephem-4-carboxylate (syn isomer) (0.59 g).

mp: 190°–200° C. (dec.)

IR (Nujol): 3400–3150, 3300, 1760, 1670, 1600, 1520, 1340 cm$^{-1}$

NMR (DMSO-d$_6$, δ): 2.67 (3H, s), 2.97 and 3.56 (2H, ABq, J=18 Hz), 3.83 (3H, s), 4.21 (3H, s), 4.94 (1H, d, J=5 Hz), 5.45 (1H, dd, J=5 Hz, 8 Hz), 6.51 (1H, d, J=11 Hz), 6.79 (1H, dd, J=11 Hz), 7.82 (1H, J=8 Hz), 8.06 (2H, bs), 8.25 (1H, dd, J=2 Hz, 8 Hz), 9.10 (1H, d, J=2 Hz), 9.30 (1H, d, J=8 Hz)

EXAMPLE 34

To a solution of benzhydryl 7-[2-(2-formamidothiazol-4-yl)-2-methoxyiminoacetamido]-3-[(Z)-2-(3-pyridyl)vinylthio]-3-cephem-4-carboxylate (syn isomer) (2 g) in N,N-dimethylformamide (10 ml) was added 2-azidoethyl trifluoromethanesulfonate (2.4 g) at ambient temperature, and the mixture was stirred at 40° C. for 3 hours and then at ambient temperature through the night. The mixture was evaporated in vacuo to give a residue. The residue was subjected to column chromatography on silica gel and eluted with a mixture of ethyl acetate and tetrahydrofuran (1:1). The fractions containing the object compound were combined and evaporated in vacuo to give benzhydryl 7-[2-(2-formamidothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer) (1.36 g).

IR (Nujol): 2125, 2100, 1775, 1680, 1640 cm$^{-1}$

NMR (DMSO-d$_6$, δ): 3.90 (3H, s), 4.0–4.1 (2H, m), 4.6–4.85 (2H, m), 5.30 (1H, d, J=5 Hz), 5.93 (1H, dd, J=5 Hz, 9 Hz), 6.7–6.9 (2H, m), 7.0–7.6 (12H, m), 8.0–8.2 (2H, m), 8.3–8.6 (2H, m), 8.7–9.1 (2H, m), 9.67 (1H, d, J=9 Hz)

EXAMPLE 35

The following compounds were obtained according to similar manners to those of Examples 7, 8, 33 and 34.

(1) Benzhydryl 7-[2-(2-aminothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer).

IR (Nujol): 2130, 2100, 1780, 1670, 1630 cm$^{-1}$ (2) Benzhydryl 7-[2-(2-aminothiazol-4-yl)-2-methoxyiminoacetamido]-3-[(Z)-2-(1,2-dimethyl-5-pyridinio)-vinylthio]-3-cephem-4-carboxylate iodide hydrochloride (syn isomer).

IR (Nujol): 3350, 3150, 1780, 1670, 1630, 1565, 1545, 1275, 1220 cm$^{-1}$ (3) 7-[2-(2-Aminothiazol-4-yl)-2-ethoxyiminoacetamido]-3-[(Z)-2-(1,2-dimethyl-5-pyridinio)-vinylthio]-3-cephem-4-carboxylate (anti isomer).

IR (Nujol): 1760, 1670, 1610, 1520 cm$^{-1}$ (4) 7-[2-(2-Aminothiazol-4-yl)-2-methoxyiminoacetamido]-3-[(Z)-2-{1-(2-azidoethyl)-3-pyridinio}vinylthio]-3-cephem-4-carboxylate (syn isomer).

IR (Nujol): 2150, 2120, 1770, 1670, 1610 cm$^{-1}$ (5) 7-[2-(5-Amino-1,2,4-thiadiazol-3-yl)-2-ethoxyiminoacetamido]-3-[(Z)-2-(1,2-dimethyl-5-pyridinio)-vinylthio]-3-cephem-4-carboxylate (syn isomer).

mp: 185°–195° C. (dec.)

IR (Nujol): 3450–3150, 3300, 1775, 1680, 1615, 1530, 1350 cm$^{-1}$

NMR (DMSO-d$_6$, δ): 1.20 (3H, t, J=7 Hz), 2.67 (3H, s), 3.01 and 3.58 (2H, ABq, J=18 Hz), 4.09 (2H, q, J=7 Hz), 4.20 (3H, s), 4.94 (1H, d, J=5 Hz), 5.48 (1H, dd, J=5 Hz, 8 Hz), 6.50 (1H, d, J=11 Hz), 6.81 (1H, d, J=11 Hz), 7.79 (1H, d, J=8 Hz), 8.06 (2H, bs), 8.22 (1H, dd, J=1.5 Hz and 8 Hz), 9.08 (1H, d, J=1.5 Hz), 9.27 (1H, d, J=8 Hz)

(6) 7-[2-(2-Aminothiazol-4-yl)-2-methoxyiminoacetamido]-3-[(Z)-2-(1,2-dimethyl-5-pyridinio)-vinylthio]-3-cephem-4-carboxylate (syn isomer).

mp: 190°–195° C. (dec.)

IR (Nujol): 3300, 3200, 1770, 1660, 1610, 1530, 1340 cm$^{-1}$ (7) Benzhydryl 7-[2-(2-formamidothiazol-4-yl)-2-methoxyiminoacetamido]-3-[(Z)-2-(1,2-dimethyl-5-pyridinio)vinylthio]-3-cephem-4-carboxylate iodide (syn isomer).

IR (Nujol): 3400, 3150, 1780, 1660, 1540, 1280, 1220 cm$^{-1}$

NMR (DMSO-d$_6$, δ): 2.80 (3H, s), 3.7–4.2 (2H, m), 3.92 (3H, s), 4.24 (3H, s), 5.33 (1H, d, J=5 Hz), 5.97 (1H, dd, J=5 Hz, 8 Hz), 6.75 (1H, d, J=11 Hz), 6.92 (1H, s), 7.13 (1H, d, J=11 Hz), 7.1–7.7 (11H, m), 7.9–8.1 (1H, m), 8.1–8.5 (1H, m), 8.53 (1H, s), 9.0 (1H, m) 9.75 (1H, d, J=8 Hz)

(8) 7-[2-(5-Amino-1,2,4-thiadiazol-3-yl)-2-carboxymethoxyiminoacetamido]-3-[(Z)-2-(1-methyl-3-pyridinio)-vinylthio]-3-cephem-4-carboxylate (syn isomer).

mp: 165°–170° C. (dec.)

IR (Nujol): 3400–3100, 1760, 1630, 1600, 1510, 1240 cm$^{-1}$ (9) Benzhydryl 7-[2-(5-amino-1,2,4-thiadiazol-3-yl)-2-carboxymethoxyiminoacetamido]-3-[(Z)-2-(1-methyl-3-pyridinio)vinylthio]-3-cephem-4-carboxylate iodide (syn isomer).

IR (Nujol): 3250, 3150, 1780, 1730, 1655, 1525, 1285, 1225 cm$^{-1}$

NMR (DMSO-d$_6$, δ): 3.75 and 4.21 (2H, ABq, J=18 Hz), 4.33 (3H, s), 4.67 (2H, bs), 5.30 (1H, d, J=5 Hz), 5.97 (1H, dd, J=5 Hz, 8 Hz), 6.81 (1H, d, J=11 Hz), 7.19 (1H, d, J=11 Hz), 7.1–7.6 (10H, m), 7.9 (1H, m), 8.09 (2H, bs), 8.3–8.6 (1H, m), 8.7–9.1 (3H, m), 9.63 (1H, d, J=8 Hz)

(10) Benzhydryl 7-[2-allyloxyimino-2-(2-formamidothiazol-4-yl)acetamido]-3-[(Z)-2-(1,2-dimethyl-5-pyridinio)vinylthio]-3-cephem-4-carboxylate iodide (syn isomer).

IR (Nujol): 1780, 1670, 1530 cm$^{-1}$

NMR (DMSO-d$_6$, δ): 2.8 (3H, s), 4.2 (3H, s), 4.65 (2H, d, J=5 Hz), 5.1–5.5 (3H, m), 5.7–6.3 (2H, m), 6.75 7.07 (2H, ABq, J=11 Hz), 6.83 (1H, s), 7.1–7.5 (11H, m), 7.90 (1H, d, J=8 Hz), 8.20 (1H, d, J=8 Hz), 8.95 (1H, s), 9.75 (1H, d, J=8 Hz)

(11) Benzhydryl 7-[2-allyloxyimino-2-(2-aminothiazol-4-yl)acetamido]-3-[(Z)-2-(1,2-dimethyl-5-pyridinio)-vinylthio]-3-cephem-4-carboxylate iodide (syn isomer)

IR (Nujol): 1780, 1670, 1630, 1520 cm$^{-1}$

(12) 7-[2-Allyloxyimino-2-(2-aminothiazol-4-yl)-acetamido]-3-[(Z)-2-(1,2-dimethyl-5-pyridinio)-vinylthio]-3-cephem-4-carboxylate (syn isomer).

IR (Nujol): 1770, 1670, 1610, 1520 cm$^{-1}$

(13) Benzhydryl 7-[2-(2-formamidothiazol-4-yl)-2-ethoxyiminoacetamido]-3-[(Z)-2-(1,2-dimethyl-5-pyridinio)vinylthio]-3-cephem-4-carboxylate iodide (syn isomer).

NMR (DMSO-d$_6$, δ): 1.3 (3H, t, J=7 Hz), 4.18 (3H, s), 5.28 (1H, d, J=5 Hz), 5.90 (1H, dd, J=5 Hz, 8 Hz), 6.70, 7.05 (2H, ABq, J=11 Hz), 6.83 (1H, s), 7.05–7.60 (11H, m), 7.90 (1H, d, J=8 Hz), 8.21 (1H, d, J=8 Hz), 8.40 (1H, s), 8.85 (1H, s), 9.60 (1H, d, J=8 Hz)

(14) Benzhydryl 7-[2-(2-aminothiazol-4-yl)-2-ethoxyiminoacetamido]-3-[(Z)-2-(1,2-dimethyl-5-pyridinio)-vinylthio]-3-cephem-4-carboxylate iodide (syn isomer).

IR (Nujol): 1780, 1670, 1620, 1520 cm$^{-1}$

(15) 7-[2-(2-Aminothiazol-4-yl)-2-ethoxyiminoacetamido]-3-[(Z)-2-(1,2-dimethyl-5-pyridinio)-vinylthio]-3-cephem-4-carboxylate (syn isomer).

IR (Nujol): 1770, 1660, 1600, 1520 cm$^{-1}$

EXAMPLE 36

To a suspension of benzhydryl 7-[2-(2-formamidothiazol-4-yl)-2-methoxyiminoacetamido]-3-[(Z)-2-(1,2-dimethyl-5-pyridinio)vinylthio]-3-cephem-4-carboxylate iodide (syn isomer) (2.9 g) in methanol (15 ml) was added conc. hydrochloric acid (1.04 ml) at ambient temperature and the mixture was stirred at 33° to 35° C. for 2 hours. The reaction mixture was poured into ethyl acetate (250 ml) to give a precipitate, which was collected by filtration and dried to give benzhydryl 7-[2-(2-aminothiazol-4-yl)-2-methoxyiminoacetamido]-3-[(Z)-2-(1,2-dimethyl-5-pyridinio)vinylthio]-3-cephem-4-carboxylate iodide hydrochloride (syn isomer) (2.53 g).

IR (Nujol): 3350, 3150, 1780, 1670, 1630, 1565, 1545, 1275, 1220 cm$^{-1}$

NMR (DMSO-d$_6$, δ): 2.82 (3H, s), 3.7–4.2 (2H, m), 3.93 (3H, s), 4.27 (3H, s), 5.32 (1H, d, J=5 Hz), 5.92 (1H, dd, J=5 Hz, 8 Hz), 6.82 (1H, d, J=11 Hz), 6.95 (1H, s), 6.98 (1H, s), 7.18 (1H, d, J=11 Hz), 7.1–7.7 (10H, m), 7.8–8.2 (1H, m), 8.2–8.6 (1H, m), 9.1 (1H, m), 9.90 (1H, d, J=8 Hz)

EXAMPLE 37

A solution of 7-[2-carboxymethoxyimino-2-{2-(2,2,2-trifluoroacetamido)thiazol-4-yl}acetamido]-3-vinylthio-3-cephem-4-carboxylic acid (syn isomer) (1 g) and sodium acetate (1.41 g) in water (21 ml) was stirred at ambient temperature over night. The mixture was adjusted to pH 2 with 1N hydrochloric acid to give a precipitate. The precipitate was collected by filtration, washed with water and dried over phosphorus pentoxide to give 7-[2-(2-aminothiazol-4-yl)-2-carboxymethoxyiminoacetamido]-3-vinylthio-3-cephem-4-carboxylic acid (syn isomer) (690 mg).

mp: 192° C. (dec.)

IR (Nujol): 1760, 1660, 1630 cm$^{-1}$

NMR (DMSO-d$_6$, δ): 3.48, 3.83 (2H, ABq, J=18 Hz), 4.50 (2H, s), 5.12 (1H, d, J=5 Hz), 5.34 (1H, d, J=17

Hz), 5.40 (1H, d, J=10 Hz), 5.67 (1H, dd, J=5 Hz, 8 Hz), 6.53 (1H, dd, J=17 Hz, 10 Hz), 6.68 (1H, s) and 9.35 (1H, d, J=8 Hz)

EXAMPLE 38

The following compounds were obtained according to similar manners to those of Examples 10, 11, 36 and 37.

(1) 7-[2-Methoxyimino-2-(5-amino-1,2,4-thiadiazol-3-yl)acetamido]-3-[(Z)-2-(1,2-dimethyl-5-pyridinio)-vinylthio]-3-cephem-4-carboxylate (syn isomer).

mp: 190°-200° C. (dec.)

IR (Nujol): 3400-3150, 3300, 1760, 1670, 1600, 1520, 1340 cm$^{-1}$ (2) Benzhydryl 7-[2-(2-aminothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer).

IR (Nujol): 2130, 2100, 1780, 1670, 1630 cm$^{-1}$

NMR (DMSO-d$_6$, δ): 3.95 (3H, s), 3.9-4.2 (2H, m), 4.6-4.9 (2H, m), 5.30 (1H, d, J=5 Hz), 5.75-6.05 (1H, m), 6.80 (1H, ABq, J=12 Hz), 6.93 (1H, s), 7.05-7.6 (12H, m), 8.1 (1H, m), 8.4 (1H, m), 8.8-9.1 (2H, m), 9.8 (1H, d, J=8 Hz)

(3) 7-[2-(2-Aminothiazol-4-yl)-2-ethoxyiminoacetamido]-3-[(Z)-2-(1,2-dimethyl-5-pyridinio)-vinylthio]-3-cephem-4-carboxylate (anti isomer).

IR (Nujol): 1760, 1670, 1610, 1520 cm$^{-1}$ (4) 7-[2-(2-Aminothiazol-4-yl)-2-methoxyiminoacetamido]-3-[(Z)-2-{1-(2-azidoethyl-3-pyridinio}vinylthio]-3-cephem-4-carboxylate (syn isomer).

IR (Nujol): 2150, 2120, 1770, 1670, 1610 cm$^{-1}$ (5) p-Nitrobenzyl 7-[2-(5-amino-1,2,4-thiadiazol-3-yl)-2-ethoxyiminoacetamido]-3-vinylthio-3-cephem-4-carboxylate (syn isomer).

IR (Nujol): 1770, 1680, 1615, 1525, 1455 cm$^{-1}$ (6) 7-[2-(5-Amino-1,2,4-thiadiazol-3-yl)-2-ethoxyiminoacetamido]-3-vinylthio-3-cephem-4-carboxylic acid (syn isomer).

mp: 145° C. (dec.)

IR (Nujol): 1765, 1670, 1525 cm$^{-1}$ (7) 7-[2-(5-Amino-1,2,4-thiadiazol-3-yl)-2-ethoxyiminoacetamido]-3-[(Z)-2-(1,2-dimethyl-5-pyridinio)-vinylthio]-3-cephem-4-carboxylate (syn isomer).

mp: 185°-195° C. (dec.)

IR (Nujol): 3450-3150, 3300, 1775, 1680, 1615, 1530, 1350 cm$^{-1}$ (8) 7-[2-(5-Amino-1,2,4-thiadiazol-3-yl)-2-methoxyiminoacetamido]-3-[(Z)-2-(2-methyl-5-pyridyl)-vinylthio]-3-cephem-4-carboxylic acid (syn isomer).

mp: 179°-185° C. (dec.)

IR (Nujol): 3300, 3200, 1775, 1680, 1620, 1530, 1350 cm$^{-1}$ (9) Benzhydryl 7-[2-(5-amino-1,2,4-thiadiazol-3-yl)-2-methoxyiminoacetamido]-3-[(Z)-2-(2-methyl-5-pyridyl)vinylthio]-3-cephem-4-carboxylate (syn isomer).

IR (Nujol): 3300, 3150, 1780, 1670, 1610, 1600, 1530, 1280, 1220 cm$^{-1}$

(10) 7-[2-(2-Aminothiazol-4-yl)-2-methoxyiminoacetamido]-3-[(Z)-2-(1,2-dimethyl-5-pyridinio)-vinylthio]-3-cephem-4-carboxylate (syn isomer).

mp: 190°-195° C. (dec.)

IR (Nujol): 3300, 3200, 1770, 1660, 1610, 1530, 1340 cm$^{-1}$

(11) 7-[2-(2-Aminothiazol-4-yl)-2-methoxyiminoacetamido]-3-[(Z)-2-(2-methyl-5-pyridyl)vinylthio]-3-cephem-4carboxylic acid (syn isomer).

mp: 177°-182° C. (dec.)

IR (Nujol): 3300, 3200, 1770, 1670, 1620, 1535, 1350 cm$^{-1}$

(12) Benzhydryl 7-[2-(2-aminothiazol-4-yl)-2-methoxyiminoacetamido]-3-[(Z)-2-(2-methyl-5-pyridyl)-vinylthio]-3-cephem-4-carboxylate (syn isomer).

IR (Nujol): 3300, 3150, 1780, 1670, 1610, 1535, 1490, 1280, 1220 cm$^{-1}$

NMR (DMSO-d$_6$, δ): 2.47 (3H, s), 3.73 and 4.12 (2H, ABq, J=18 Hz), 3.83 (3H, s), 5.27 (1H, d, J=5 Hz), 5.87 (1H, dd, J=5 Hz, 8 Hz), 6.77 (2H, s), 6.71 (1H, s), 6.88 (1H, s), 7.0-7.8 (12H, m), 8.4-8.6 (1H, m), 9.63 (1H, d, J=8 Hz)

(13) 7-[2-(5-Amino-1,2,4-thiadiazol-3-yl)-2-ethoxyiminoacetamido]-3-[(Z)-2-(2-methyl-5-pyridyl)-vinylthio]-3-cephem-4-carboxylic acid (syn isomer).

mp: 175°-180° C. (dec.)

IR (Nujol): 3300, 3150, 1770, 1670, 1610, 1530, 1290 cm$^{-1}$

(14) Benzhydryl 7-[2-(5-amino-1,2,4-thiadiazol-3-yl)-2-ethoxyiminoacetamido]-3-[(Z)-2-(2-methyl-5-pyridyl)vinylthio]-3-cephem-4-carboxylate (syn isomer).

IR (Nujol): 3300, 3150, 1780, 1670, 1610, 1530, 1280, 1220 cm$^{-1}$

(15) 7-[2-(5-Amino-1,2,4-thiadiazol-3-yl)-2-carboxymethoxyiminoacetamido]-3-[(Z)-2-(1-methyl-3-pyridinio)vinylthio]-3-cephem-4-carboxylate (syn isomer).

mp: 165°-170° C. (dec.)

IR (Nujol): 3400−3100, 1760, 1630, 1600, 1510, 1240 cm$^{-1}$

(16) Benzhydryl 7-[2-(5-amino-1,2,4-thiadiazol-3-yl)-2-carboxymethoxyiminoacetamido]-3-[(Z)-2-(1-methyl-3-pyridinio)vinylthio]-3-cephem-4-carboxylate iodide (syn isomer).

IR (Nujol): 3250, 3150, 1780, 1730, 1655, 1525, 1285, 1225 cm$^{-1}$

(17) 7-[2-(5-Amino-1,2,4-thiadiazol-3-yl)-2-(2-cyclopenten-1-yl)oxyiminoacetamido]-3-[(Z)-2-(3-pyridyl)-vinylthio]-3-cephem-4-carboxylic acid (syn isomer).

mp: 90°-100° C. (dec.)

IR (Nujol): 3400−3100, 1770, 1660, 1525 cm$^{-1}$

(18) 7-[2-(2-Aminothiazol-4-yl)-3-hydroxypropionamido]-3-[(Z)-2-(3-pyridyl)vinylthio]-3-cephem-4-carboxylic acid.

mp: 100°-110° C. (dec.)

IR (Nujol): 3200, 1770, 1670∼1520, 1600, 1340, 1250 cm$^{-1}$

NMR (DMSO-d$_6$, δ): 3.4-4.2 (5H, m), 5.14 (1H, d, J=5 Hz), 5.72 (1H, dd, J=5 Hz and 8 Hz), 6.25 and 6.30 (1H, s), 6.75 (2H, s), 7.3-7.6 (1H, m), 7.7-8.1 (1H, m), 8.3-8.7 (2H, m), 8.91 (1H, d, J=8 Hz)

(19) 7-[2-(2-Aminothiazol-4-yl)-2-methoxyiminoacetamido]-3-vinylthio-3-cephem-4-carboxylic acid (syn isomer).

mp: 195°-205° C. (dec.)

IR (Nujol): 3200, 1770, 1660, 1530 cm$^{-1}$

NMR (DMSO-d$_6$, δ): 3.49 and 3.83 (2H, ABq, J=18 Hz), 3.77 (3H, s), 5.14 (1H, d, J=5 Hz), 5.36 (1H, d, J=17 Hz), 5.45 (1H, d, J=9 Hz), 5.69 (1H, dd, J=5 Hz and 8 Hz), 6.59 (1H, dd, J=9 Hz and 17 Hz), 6.68 (1H, s), 7.12 (2H, bs), 9.53 (1H, d, J=8 Hz)

(20) Benzhydryl 7-[2-allyloxyimino-2-(2-aminothiazol-4-yl)acetamido]-3-[(Z)-2-(1,2-dimethyl-5-pyridinio)vinylthio]-3-cephem-4-carboxylate iodide (syn isomer).

IR (Nujol): 1780, 1670, 1630, 1520 cm$^{-1}$

NMR (DMSO-d$_6$, δ): 2.77 (3H, s), 4.17 (3H, s), 4.60 (2H, d, J=8 Hz), 5.0-5.4 (3H, m), 5.70-6.0 (2H, m), 6.70, 7.05 (2H, ABq, J=11 Hz), 6.82 (1H, s), 7.1-7.5

(11H, m), 7.90 (1H, d, J=8 Hz), 8.20 (1H, d, J=8 Hz), 8.83 (1H, s), 9.63 (1H, d, J=8 Hz)

(21) 7-[2-Allyloxyimino-2-(2-aminothiazol-4-yl)-acetamido]-3-[(Z)-2-(1,2-dimethyl-5-pyridinio)-vinylthio]-3-cephem-4-carboxylate (syn isomer).

IR (Nujol): 1770, 1670, 1610, 1520 cm$^{-1}$

(22) Benzhydryl 7-[2-(2-aminothiazol-4-yl)-2-ethoxyiminoacetamido]-3-[(Z)-2-(1,2-dimethyl-5-pyridinio)-vinylthio]-3-cephem-4-carboxylate iodide (syn isomer).

IR (Nujol): 1780, 1670, 1620, 1520 cm$^{-1}$

NMR (DMSO-d$_6$, δ): 1.30 (3H, t, J=7 Hz), 2.78 (3H, s), 4.20 (3H, s), 5.27 (1H, d, J=5 Hz), 5.86 (1H, dd, J=5 Hz, 8 Hz), 6.83 (1H, s), 6.6–7.0 (2H, m), 7.1–7.5 (11H, m), 7.90 (1H, d, J=8 Hz), 8.20 (1H, d, J=8 Hz), 8.90 (1H, s), 9.67 (1H, d, J=8 Hz)

(23) 7-[2-(2-Aminothiazol-4-yl)-2-ethoxyiminoacetamido]-3-[(Z)-2-(1,2-dimethyl-5pyridinio)-vinylthio]-3-cephem-4-carboxylate (syn isomer).

IR (Nujol): 1770, 1660, 1600, 1520 cm$^{-1}$

(24) Benzhydryl 7-[2-allyloxyimino-2-(5-amino-1,2,4-thiadiazol-3-yl)acetamido]-3-[(Z)-2-(2-methyl-5-pyridyl)vinylthio]-3-cephem-4-carboxylate (syn isomer).

IR (Nujol): 1770, 1670, 1660, 1520 cm$^{-1}$

(25) 7-[2-Allyloxyimino-2-(5-amino-1,2,4-thiadiazol-3-yl)acetamido]-3-[(Z)-2-(2-methyl-5-pyridyl)vinylthio]-3-cephem-4-carboxylic acid (syn isomer).

IR (Nujol): 1770 cm$^{-1}$

(26) Benzhydryl 7-[2-allyloxyimino-2-(2-aminothiazol-4-yl)acetamido]-3-[(Z)-2-(2-methyl-5-pyridyl)-vinylthio]-3-cephem-4-carboxylate (syn isomer).

IR (Nujol): 1780, 1670, 1610, 1530 cm$^{-1}$

NMR (DMSO-d$_6$, δ): 3.5–4.2 (2H, m), 4.55 (2H, d, J=5 Hz), 5.0–5.4 (3H, m), 5.7–6.1 (2H, m), 6.6–6.8 (2H, m), 6.85 (1H, s), 7.0–7.4 (12H, m), 7.60 (1H, dd, J=2Hz, 8 Hz), 8.37 (1H, d, J=2 Hz), 9.55 (1H, d, J=8 Hz)

(27) 7-[2-Allyloxyimino-2-(2-aminothiazol-4-yl)-acetamido]-3-[(Z)-2-(2-methyl-5-pyridyl)vinylthio]-3-cephem-4-carboxylic acid (syn isomer).

IR (Nujol): 1770, 1660, 1530 cm$^{-1}$

(28) Benzhydryl 7-[2-(2-aminothiazol-4-yl)-2-ethoxyiminoacetamido]-3-[(Z)-2-(2-methyl-5-pyridyl)-vinylthio]-3-cephem-4-carboxylate (syn isomer).

IR (Nujol): 1780, 1670, 1610, 1520 cm$^{-1}$

NMR (DMSO-d$_6$, δ): 5.23 (1H, d, J=5 Hz), 5.65–6.0 (1H, m), 6.65 (2H, m), 6.83 (1H, s), 6.90–7.70 (13H, m), 8.35 (1H, broad s), 9.47 (1H, d, J=8 Hz)

(29) 7-[2-(2-Aminothiazol-4-yl)-2-ethoxyiminoacetamido]-3-[(Z)-2-(2-methyl-5-pyridyl)vinylthio]-3-cephem-4-carboxylic acid (syn isomer).

IR (Nujol): 1760, 1660, 1600, 1530 cm$^{-1}$

EXAMPLE 39

To a solution of benzhydryl 7-[2-(2-aminothiazol-4-yl)-2-ethoxyiminoacetamido]-3-[(Z)-2-(1,2-dimethyl-5-pyridinio)vinylthio]-3-cephem-4-carboxylate iodide (syn isomer) (1 g) in a mixture of anisole (4 ml) and trifluoroacetic acid (5.5 ml) under ice-cooling. The mixture was stirred for 1 hour at ambient temperature and poured into diisopropyl ether. The resulting precipitate was collected, washed with diisopropyl ether, and dissolved in a mixture of ethyl acetate and an aqueous solution of sodium bicarbonate at pH 7. The aqueous layer was separated and concentrated until ethyl acetate has been removed. This solution was subjected to column chromatography on macroporous non-ionic adsorption resin "Diaion HP-20". After the column was washed with water, the elution was carried out with 10% aqueous solution of isopropyl alcohol. The eluates containing the object compound were collected, evaporated to remove isopropyl alcohol under reduced pressure and lyophilized to give 7-[2-(2-aminothiazol-4-yl)-2-ethoxyiminoacetamido]-3-[(Z)-2-(1,2-dimethyl-5-pyridinio)vinylthio]-3-cephem-4-carboxylate (anti isomer) (0.20 g).

IR (Nujol): 1760, 1670, 1610, 1520 cm$^{-1}$

NMR (DMSO-d$_6$, δ): 1.30 (3H, t, J=7 Hz), 2.70 (3H, s), 4.15 (2H, q, J=7 Hz, 13 Hz), 4.20 (3H, s), 4.95 (1H, d, J=5 Hz), 5.43 (1H, dd, J=5 Hz, 8 Hz), 6.53, 6.80 (2H, ABq, J=11 Hz), 7.35 (1H, s), 7.80 (1H, d, J=8 Hz), 8.25 (1H, d, J=8 Hz), 9.10 (1H, d, J=8 Hz), 9.15 (1H, s)

EXAMPLE 40

To a suspension of benzhydryl 7-[2-(2-aminothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer) (1.1 g) in anisole (6.8 ml) was added trifluoroacetic acid (5.0 ml) under ice-cooling and the mixture was stirred at the same temperature for half an hour. The mixture was dropwise added to diethyl ether. The precipitates were collected by filtration and washed with diethyl ether. The precipitates were added to a mixture of water and ethyl acetate under stirring, and the mixture was adjusted to pH 7 with a saturated aqueous solution of sodium bicarbonate. The aqueous layer was separated and concentrated until ethyl acetate has been removed. This solution was subjected to column chromatography on macroporous non-ionic adsorption resin "Diaion HP-20" (30 ml). After the column was washed with water, the elution was carried out with 4–15% aqueous solution of isopropyl alcohol. The eluates containing the object compound were collected, evaporated to remove isopropyl alcohol under reduced pressure and lyophilized to give 7-[2-(2-aminothiazol-4-yl)-2-methoxyiminoacetamido]-3-[(Z)-2-{1-(2-azidoethyl)-3-pyridinio}vinylthio]-3-cephem-4-carboxylate (syn isomer) (530 mg).

IR (Nujol): 2150, 2120, 1770, 1670, 1610 cm$^{-1}$

NMR (DMSO-d$_6$, δ): 3.85 (3H, s), 4.6–5.2 (2H, m), 5.0 (1H, d, J=5 Hz), 5.55 (1H, dd, J=5 Hz, 8 Hz), 6.70 (1H, s), 7.9–8.2 (1H, m), 8.35–8.9 (2H, m), 9.2–9.5 (2H, m)

mp: 145° C. (dec.)

EXAMPLE 41 p-Nitrobenzyl 7-[2-((Z)-2-cyanovinylthio)-acetamido]-3-vinylthio-3-cephem-4-carboxylate (300 mg) was hydrogenated in the presence of 10% palladium on carbon (270 mg) in a mixture of tetrahydrofuran (9 ml), methanol (1.5 ml) and acetic acid (0.033 ml) at ambient temperature for 3 hours under 1 atmospheric pressure of hydrogen. The catalyst was filtered off and washed with methanol. The filtrate and washings were combined and concentrated in vacuo. The residue was dissolved in a mixture of ethyl acetate and water at pH 7. The aqueous layer was separated, adjusted to pH 7 with dilute hydrochloric acid and extracted with ethyl acetate. The organic layer was washed with a saturated aqueous solution of sodium chloride, dried over magnesium sulfate, concentrated in vacuo and triturated with diisopropyl ether to give 7-[2-((Z)-2-cyanovinylthio)acetamido]-3-vinylthio-3-cephem-4-carboxylic acid (97 mg).

mp: 145° C. (dec.)

IR (Nujol): 3270, 2210, 1750, 1710, 1660, 1530 cm$^{-1}$

NMR (DMSO-d$_6$, δ): 3.50, 3.87 (2H, ABq, J=18 Hz), 3.67 (2H, s), 5.07 (1H, d, J=5 Hz), 5.35 (1H, d, J=17

Hz), 5.43 (1H, d, J=10 Hz), 5.62 (1H, dd, J=8 Hz, 5 Hz), 5.63 (1H, d, J=11 Hz), 6.57 (1H, dd, J=10 Hz, 17 Hz), 7.53 (1H, d, J=11 Hz), 9.09 (1H, d, J=8 Hz)

EXAMPLE 42

The following compounds were obtained according to similar manners to those of Examples 13–17, 40 and 41.

(1) 7-[2-Methoxyimino-2-(5-amino-1,2,4-thiadiazol-3-yl)acetamido]-3-[(Z)-2-(1,2-dimethyl-5-pyridinio)vinylthio]-3-cephem-4-carboxylate (syn isomer).

mp: 190°–200° C. (dec.)

IR (Nujol): 3400–3150, 3300, 1760, 1670, 1600, 1520, 1340 cm$^{-1}$ (2) 7-[2-(2-Aminothiazol-4-yl)-2-carboxymethoxyiminoacetamido]-3-vinylthio-3-cephem-4-carboxylic acid (syn isomer).

mp: 192° C. (dec.)

IR (Nujol): 1760, 1660, 1630 cm$^{-1}$ (3) 7-[2-Carboxymethoxyimino-2-{2-(2,2,2-trifluoroacetamido)thiazol-4-yl}acetamido]-3-vinylthio-3-cephem-4-carboxylic acid (syn isomer).

IR (Nujol): 1750, 1710, 1655, 1530 cm$^{-1}$ (4) 7-[2-(5-Amino-1,2,4-thiadiazol-3-yl)-2-ethoxyiminoacetamido]-3-vinylthio-3-cephem-4-carboxylic acid (syn isomer).

mp: 145° C. (dec.)

IR (Nujol): 1765, 1670, 1525 cm$^{-1}$

NMR (DMSO-d$_6$, δ): 1.21 (3H, t, J=7 Hz), 3.48, 3.84 (2H, ABq, J=18 Hz), 4.11 (2H, q, J=7 Hz), 5.12 (1H, d, J=5 Hz), 5.33 (1H, d, J=16 Hz), 5.40 (1H, d, J=10 Hz), 5.72 (1H, dd, J=5 Hz, 8 Hz), 6.54 (1H, dd, J=10 Hz, 16 Hz), 7.98 (2H, s), 9.42 (1H, d, J=8 Hz)

(5) 7-[2-(5-Amino-1,2,4-thiadiazol-3-yl)-2-ethoxyiminoacetamido]-3-[(Z)-2-(1,2-dimethyl-5-pyridinio)-vinylthio]-3-cephem-4-carboxylate (syn isomer).

mp: 185°–195° C. (dec.)

IR (Nujol): 3450–3150, 3300, 1775, 1680, 1615, 1530, 1350 cm$^{-1}$ (6) 7-[2-(5-Amino-1,2,4-thiadiazol-3-yl)-2-methoxyiminoacetamido]-3-[(Z)-2-(2-methyl-5-pyridyl)-vinylthio]-3-cephem-4-carboxylic acid (syn isomer).

mp: 179°–185° C. (dec.)

IR (Nujol): 3300, 3200, 1775, 1680, 1620, 1530, 1350 cm$^{-1}$

NMR (DMSO-d$_6$, δ): 2.50 (3H, s), 3.65 and 4.06 (2H, ABq, J=18 Hz), 3.90 (3H, s), 5.16 (1H, d, J=5Hz), 5.78 (1H, dd, J=5 Hz, 8 Hz), 6.67 (2H, s), 7.26 (1H, d, J=8 Hz), 7.76 (1H, dd, J=3 Hz, 8 Hz), 8.02 (2H, bs), 8.44 (1H, d, J=3 Hz), 9.47 (1H, d, J=8 Hz)

(7) 7-[2-(2-Aminothiazol-4-yl)-2-methoxyiminoacetamido]-3-[(Z)-2-(1,2-dimethyl-5-pyridinio)-vinylthio]-3-cephem-4-carboxylate (syn isomer).

mp: 190°–195° C. (dec.)

IR (Nujol): 3300, 3200, 1770, 1660, 1610, 1530, 1340 cm$^{-1}$

NMR (DMSO-d$_6$, δ): 2.68 (3H, s), 3.02 and 3.64 (2H, ABq, J=18 Hz), 3.78 (3H, s), 4.23 (3H, s), 4.98 (1H, d, J=5 Hz), 5.45 (1H, dd, J=5 Hz and 8 Hz), 6.55 (1H, d, J=11 Hz), 6.62 (1H, s), 6.82 (1H, d, J=11 Hz), 7.16 (2H, bs), 7.7–7.6 (1H, m), 8.1–8.4 (1H, m), 9.13 (1H, bs), 9.40 (1H, d, J=8 Hz)

(8) 7-[2-(2-Aminothiazol-4-yl)-2-methoxyiminoacetamido]-3-[(Z)-2-(2-methyl-5-pyridyl)vinylthio]-3-cephem-4-carboxylic acid (syn isomer).

mp: 177°–182° C. (dec.)

IR (Nujol): 3300, 3200, 1770, 1670, 1620, 1535, 1350 cm$^{-1}$

NMR (DMSO-d$_6$, δ): 2.48 (3H, s), 3.73 and 4.17 (2H, ABq, J=18 Hz), 3.92 (3H, s), 5.27 (1H, d, J=5 Hz), 5.83 (1H, dd, J=5 Hz, 8Hz), 6.75 (2H, s), 6.79 (1H, s), 7.0–7.5 (3H, m), 7.7–8.0 (1H, m), 8.5–8.7 (1H, m), 9.65 (1H, d, J=8 Hz)

(9) 7-[2-(5-Amino-1,2,4-thiadiazol-3-yl)-2-ethoxyiminoacetamido]-3-[(Z)-2-(2-methyl-5-pyridyl)vinylthio]-3-cephem-4-carboxylic acid (syn isomer).

mp: 175°–180° C. (dec.)

IR (Nujol): 3300, 3150, 1770, 1670, 1610, 1530, 1290 cm$^{-1}$

NMR (DMSO-d$_6$, δ): 1.27 (3H, t, J=7 Hz), 2.55 (2H, s), 3.67 and 4.12 (2H, ABq, J=18 Hz), 4.19 (2H, q, J=7 Hz), 5.23 (1H, d, J=5 Hz), 5.86 (1H, dd, J=5 Hz and 8 Hz), 6.80 (2H, bs), 7.47 (1H, d, J=8 Hz), 8.00 (1H, dd, J=2 Hz and 8 Hz), 8.05 (2H, bs), 8.60 (1H, d, J=2 Hz), 9.58 (1H, J=8 Hz)

(10) 7-[2-(5-Amino-1,2,4-thiadiazol-3-yl)-2-carboxymethoxyiminoacetamido]-3-[(Z)-2-(1-methyl-3-pyridinio)vinylthio]-3-cephem-4-carboxylate (syn) isomer).

mp: 165°–170° C. (dec.)

IR (Nujol): 3400–3100, 1760, 1630, 1600, 1510, 1240 cm$^{-1}$

NMR (DMSO-d$_6$, δ): 3.6–4.4 (2H, m), 4.32 (3H, s), 4.52 (2H, bs), 5.03 (1H, d, J=5 Hz), 5.71 (1H, d, J=5 Hz), 6.68 (1H, d, J=12 Hz), 6.95 (1H, d, J=12 Hz), 7.8–8.3 (3H, m), 8.3–9.0 (2H, m), 9.0–9.3 (1H, m), 10.0 (1H, d, J=8 Hz)

(11) 7-[2-(5-Amino-1,2,4-thiadiazol-3-yl)-2-(2-cyclopenten-1-yl)oxyiminoacetamido]-3-[(Z)-2-(3-pyridyl)-vinylthio]-3-cephem-4-carboxylic acid (syn isomer).

mp: 90°–100° C. (dec.)

IR (Nujol): 3400–3100, 1770, 1660, 1525 cm$^{-1}$

(12) 7-[2-(2-Aminothiazol-4-yl)-3-hydroxypropionamido]-3-[(Z)-2-(3-pyridyl)vinylthio]-3-cephem-4-carboxylic acid.

mp: 100°–110° C. (dec.)

IR (Nujol): 3200, 1770, 1670–1520, 1600, 1340, 1250 cm$^{-1}$

(13) 7-(2-Phenyl acetamido)-3-vinylthio-3-cephem-4-carboxylic acid.

IR (Nujol): 3300, 1780, 1690, 1630, 1520, 1360, 1230 cm$^{-1}$

NMR (DMSO-d$_6$, δ): 3.49 and 3.83 (2H, ABq, J=18 Hz), 3.47 (2H, s), 5.02 (1H, d, J=5 Hz), 5.32 (1H, d, J=17 Hz), 5.46 (1H, d, J=10 Hz), 5.55 (1H, dd, J=5 Hz and 8 Hz), 6.52 (1H, dd, J=10 Hz and 17 Hz), 7.13 (5H, s), 8.93 (1H, d, J=8 Hz)

(14) 7-[2-(2-Aminothiazol-4-yl)-2-methoxyiminoacetamido]-3-vinylthio-3-cephem-4-carboxylic acid (syn isomer).

mp: 195°–205° C. (dec.)

IR (Nujol): 3200, 1770, 1660, 1530 cm$^{-1}$

(15) 7-[2-Methoxyimino-2-{2-(2,2,2-trifluoroacetamido)thiazol-4-yl}acetamido]-3-vinylthio-3-cephem-4-carboxylic acid (syn isomer).

IR (Nujol): 3200, 1775, 1720, 1655, 1520, 1265, 1235, 1210 cm$^{-1}$

NMR (DMSO-d$_6$, δ): 3.48 and 3.84 (2H, ABq, J=18 Hz), 3.85 (3H, s), 5.12 (1H, d, J=5 Hz), 5.33 (1H, d, J=16 Hz), 5.42 (1H, d, J=9 Hz), 5.68 (1H, dd, J=5Hz and 8 Hz), 6.52 (1H, dd, J=9 Hz and J=16 Hz), 7.40 (1H, s), 9.57 (1H, d, J=8 Hz)

(16) 7-[2-Allyloxyimino-2-(2-aminothiazol-4-yl)-acetamido]-3-[(Z)-2-(1,2-dimethyl-5-pyridinio)vinylthio]-3-cephem-4-carboxylate (syn isomer).

mp: 150° C. (dec.)

IR (Nujol): 1770, 1670, 1610, 1520 cm$^{-1}$

NMR (DMSO-d$_6$, δ): 2.70 (3H, s), 4.25 (3H, s), 4.55 (2H, d, J=8 Hz), 5.0 (1H, d, J=5 Hz), 5.0–5.2 (2H, m), 5.47 (1H, dd, J=5 Hz, 8 Hz), 5.65–6.1 (1H, m), 6.55, 6.85 (2H, ABq, J=11 Hz), 6.60 (1H, s), 7.15 (2H, s), 7.80 (1H, d, J=8 Hz), 8.25 (1H, d, J=8 Hz), 9.17 (1H, s), 9.37 (1H, d, J=8 Hz)

(17) 7-[2-(2-Aminothiazol-4-yl)-2-ethoxyiminoacetamido]-3-[(Z)-2-(1,2-dimethyl-5-pyridinio)-vinylthio]-3-cephem-4-carboxylate syn isomer).

mp: 150° C.

IR (Nujol): 1770, 1660, 1600, 1520 cm$^{-1}$

NMR (DMSO-d$_6$, δ): 1.23 (3H, t, J=Hz), 2.70 (3H, s), 4.07 (2H, q, J=7Hz, 13Hz), 4.23 (3H, s), 5.0 (1H, d, J=5Hz), 5.50 (1H, dd, J=5Hz, 8Hz), 6.55, 6.85 (2H, ABq, J=11Hz), 6.60 (1H, s), 7.10 (2H, broad s), 7.80 (1H, d, J=8Hz), 8.25 (1H, d, J=8 Hz), 9.10 (1H, s), 9.30 (1H, d, J=8Hz)

(18) 7-[2-Allyloxyimino-2-(5-amino-1,2,4-thiadiazol-3-yl)acetamido]-3-[(Z)-2-(2-methyl-5-pyridyl)vinythio]-3-cephem-4-carboxylic acid (syn isomer).

IR (Nujol): 1770 cm$^{-1}$

NMR (DMSO-d$_6$, δ): 2.75 (3H, s), 4.65 (2H, d, J=5Hz), 5.1–5.5 (3H, m), 5.7–6.2 (2H, m), 6.8, 7.0 (2H, ABq, J=11Hz), 7.8 (1H, d, J=8Hz), 8.35 (1H, d, J=8Hz), 8.67 (1H, s), 9.52 (1H, d, J=8Hz)

(19) 7-[2-Allyloxyimino-2-(2-aminothiazol-4-yl)-acetamido]-3-[(Z)-2-(2-methyl-5-pyridyl)vinylthio]-3-cephem-4-carboxylic acid (syn isomer).

mp: 145° C. (dec.)

IR (Nujol): 1770, 1660, 1530 cm$^{-1}$

NMR (DMSO-d$_6$, δ): 4.57 (2H, d, J=5Hz), 5.0–5.4 (3H, m), 5.6–6.2 (2H, m), 6.70 (2H, d, J=2Hz), 7.35 (1H, d, J=8Hz), 7.83 (1H, dd, J=2Hz, 8Hz), 8.47 (1H, d, J=2Hz), 9.53 (1H, d, J=8Hz)

(20) 7-[2-(2-Aminothiazol-4-yl)-2-ethoxyiminoacetamido]-3-[(Z)-2-(2-methyl-5-pyridyl)vinylthio]-3-cephem-4-carboxylic acid (syn isomer)

mp: 145° C. (dec.)

IR (Nujol): 1760, 1660, 1600, 1530 cm$^{-1}$

NMR (DMSO-d$_6$, δ): 1.28 (3H, t, J=6Hz), 4.10 (2H, q, J=6Hz, 12Hz), 5.10 (1H, d, J=5Hz), 5.63 (1H, dd, J=5Hz, 8Hz), 6.47, 6.65 (2H, ABq, J=12Hz), 6.68 (1H, s), 7.10 (1H, s), 7.20 (1H, d, J=8Hz), 7.70 (1H, dd, J=2Hz, 8Hz), 8.40 (1H, d, J=2Hz), 9.40 (1H, d, J=8Hz)

EXAMPLE 43 p-Nitrobenzyl 7-[2-(p-nitrobenzyloxycarbonylmethoxyimino)-2-{2-(2,2,2-trifluoroacetamido)thiazol-4-yl}acetamido]-3-vinylthio-3-cephem-4-carboxylate (syn isomer) (2.3 g) was hydrogenated in the presence of 5% palladium on carbon in a mixture of tetrahydrofuran (100 ml), ethanol (11.5 ml) and 0.025M phosphate buffer solution (pH 6.85) (125 ml) at ambient temperature for 5 hours under 1 atmospheric pressure of hydrogen. The catalyst was filtered off and washed with ethyl acetate and a saturated aqueous solution of sodium bicarbonate successively. The filtrate and washings were combined and adjusted to pH 8 with dilute hydrochloric acid. The aqueous layer was separated, adjusted to pH 6 with dilute hydrochloric acid and washed with ethyl acetate. The aqueous layer was adjusted to pH 2 with dilute hydrochloric acid and extracted with ethyl acetate. The extract was washed with a saturated aqueous solution of sodium chloride, dried over magnesium sulfate, concentrated in vacuo and triturated with diisopropyl ether to give 7-[2-carboxymethoxyimino-2-{2-(2,2,2-trifluoroacetamido)thiazol-4-yl}acetamido]-3-vinylthio-3-cephem-4-carboxylic acid (syn isomer) (1.05 g).

IR (Nujol): 1750, 1710, 1655, 1530 cm$^{-1}$

NMR (DMSO-d$_6$, δ): 3.50, 3.87 (2H, ABq, J=18Hz), 4.59 (2H, s), 5.14 (1H, d, J=5Hz), 5.36 (1H, d, J=16Hz), 5.42 (1H, d, J=9Hz), 5.72 (1H, dd, J=5Hz, 8Hz), 6.55 (1H, dd, J=9Hz, 16Hz), 7.46 (1H, s), 9.56 (1H, d, J=8Hz)

EXAMPLE 44

The following compounds were obtained according to similar manners to those of Examples 19 and 43.

(1) 7-[2-(2-Aminothiazol-4-yl)-2-carboxymethoxyiminoacetamido]-3-vinylthio-3-cephem-4-carboxylic acid (syn isomer).

mp: 192° C. (dec.)

IR (Nujol): 1760, 1660, 1630 cm$^{-1}$ (2) 7-[2-(5-Amino-1,2,4-thiadiazol-3-yl)-2-carboxymethoxyiminoacetamido]-3-[(Z)-2-(1-methyl-3-pyridinio)-vinylthio]-3-cephem-4-carboxylate (syn isomer).

mp: 165–170° C. (dec.)

IR (Nujol): 3400–3100, 1760, 1630, 1600, 1510, 1240 cm$^{-1}$

EXAMPLE 45

To a solution of N,N-diisopropylamine (0.65 ml) in tetrahydrofuran (7 ml) was added 1.55M n-butyllithium in n-hexane (2.88 ml) at −20~−15° C. The mixture was stirred for 30 minutes at 0° C. To the solution was added a solution of 2-ethoxy-1,3-oxathiolane (642 mg) in tetrahydrofuran (2 ml) at −60° C., and the resultant mixture was stirred for 30 minutes at the same temperature. The solution was added to a solution of p-nitrobenzyl 7-[2-(5-amino-1,2,4-thiadiazol-3-yl)-2-ethoxyiminoacetamido]-3-mesyloxy-3-cephem-4-carboxylate (syn isomer) (2 g) in tetrahydrofuran (30 ml) at −62° C. After the mixture was stirred for 15 minutes at the same temperature, 1N hydrochloric acid (5 ml) was added thereto. The mixture was allowed to warm up till 0° C. and extracted with ethyl acetate. The extract was washed with water, dried over magnesium sulfate and concentrated in vacuo. The residue was subjected to column chromatography on silica gel and eluted with a mixture of ethyl acetate and chloroform (1:2). The fractions containing the object compound were combined and concentrated in vacuo to give p-nitrobenzyl 7-[2-(5-amino-1,2,4-thiadiazol-3-yl)-2-ethoxyiminoacetamido]-3-vinylthio-3-cephem-4-carboxylate (syn isomer) (805 mg).

IR (Nujol): 1770, 1680, 1615, 1525, 1455 cm$^{-1}$

NMR (DMSO-d$_6$, δ): 1.26 (3H, t, J=7Hz), 3.60, 3.93 (2H, ABq, J=18Hz), 4.15 (2H, q, J=7Hz), 5.18 (1H, d, J=5Hz), 5.36 (2H, s), 5.42 (1H, d, J=15Hz), 5.50 (1H, d, J=9Hz), 5.82 (1H, dd, J=5Hz, 8Hz), 6.62 (1H, dd, J=9Hz, 15Hz), 7.58 (2H, d, J=8Hz), 8.00 (2H, s), 8.14 (2H, d, J=8hz), 9.44 (1H, d, J=8Hz)

EXAMPLE 46

The following compounds were obtained according to similar manners to those of Examples 22–25.

(1) Benzhydryl 7-[2-(2-tritylaminothiazol-4-yl)-3-hydroxypropionamido]-3-[(Z)-2-(3-pyridyl)vinylthio]-3-cephem-4-carboxylate.

IR (Nujol): 3300, 1780, 1730, 1670, 1520, 1495, 1280, 1220 cm$^{-1}$ (2) 7-[2-Methoxyimino-2-(5-amino-1,2,4-thiadiazol-3-yl)acetamido]-3-[(Z)-2-(1,2-dimethyl-5-pyridinio)-vinylthio]-3-cephem-4-carboxylate (syn isomer).

mp: 190–200° C. (dec.)

IR (Nujol): 3400–3150, 3300, 1760, 1670, 1600, 1520, 1340 cm$^{-1}$ (3) Benzhydryl 7-[2-(2-formamidothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer).

IR (Nujol): 2125, 2100, 1775, 1680, 1640 cm$^{-1}$ (4) Benzhydryl 7-[2-(2-aminothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer).

IR (Nujol): 2130, 2100, 1780, 1670, 1630 cm$^{-1}$ (5) Benzhydryl 7-[2-(2-aminothiazol-4-yl)-2-methoxyiminoacetamido]-3-[(Z)-2-(1,2-dimethyl-5-pyridinio)vinylthio]-3-cephem-4-carboxylate iodide hydrochloride (syn isomer).

IR (Nujol): 3350, 3150, 1780, 1670, 1630, 1565, 1545, 1275, 1220 cm$^{-1}$ (6) 7-[2-(2-Aminothiazol-4-yl)-2-carboxymethoxyiminoacetamido]-3-vinylthio-3-cephem-4-carboxylic acid (syn isomer).

mp: 192° C. (dec.)

IR (Nujol): 1760, 1660, 1630 cm$^{-1}$ (7) 7-[2-(2-Aminothiazol-4-yl)-2-ethoxyiminoacetamido]-3-[(Z)-2-(1,2-dimethyl-5-pyridinio)vinylthio]-3-cephem-4-carboxylate (anti isomer).

IR (Nujol): 1760, 1670, 1610, 1520 cm$^{-1}$ (8) 7-[2-(2-Aminothiazol-4-yl)-2-methoxyiminoacetamido]-3-[(Z)-2-{1-(2-azidoethyl)-3-pyridinio}-vinylthio]-3-cephem-4-carboxylate (syn isomer).

IR (Nujol): 2150, 2120, 1770, 1670, 1610 cm$^{-1}$ (9) 7-[2-Carboxymethoxyimino-2-{2-(2,2,2-trifluoroacetamido)thiazol-4-yl}acetamido]-3-vinylthio-3-cephem-4-carboxylic acid (syn isomer).

IR (Nujol): 1750, 1710, 1655, 1530 cm$^{-1}$

(10) 7-[2-((Z)-2-cyanovinylthio)acetamido]-3-vinylthio-3-cephem-4-carboxylic acid.

mp: 145° C. (dec.)

IR (Nujol): 3270, 2210, 1750, 1710, 1660, 1530 cm$^{-1}$

(11) Benzhydryl 7-formamido-3-[(Z)-2-(2-methyl-5-pyridyl)vinylthio]-3-cephem-4-carboxylate.

IR (Nujol): 3150, 1780, 1710, 1690, 1230, 1220 cm$^{-1}$

NMR (CDCl$_3$, δ): 2.56 (3H, s), 3.63 (2H, bs), 5.03 (1H, d, J=5Hz), 5.87 (1H, dd, J=5Hz, 8Hz), 6.23 (1H, d, J=11Hz), 6.63 (1H, d, J=11Hz), 6.98 (1H, s), 7.1–7.6 (11H, m), 7.6–7.9 (1H, m) 8.2–8.3 (1H, s), 8.3–8.4 (1H, m)

(12) 7-[2-(5-Amino-1,2,4-thiadiazol-3-yl)-2-ethoxyiminoacetamido]-3-vinylthio-3-cephem-4-carboxylic acid (syn isomer).

mp: 145° C. (dec.)

IR (Nujol): 1765, 1670, 1525 cm$^{-1}$

(13) p-Nitrobenzyl 7-(2-phenylacetamido)-3-vinylthio-3-cephem-4-carboxylate.

IR (Nujol): 3280, 1970, 1705, 1665, 1540, 1520 cm$^{-1}$

NMR (DMSO-d$_6$, δ): 3.52 (2H, s), 3.63, 3.93 (2H, ABq, J=18Hz), 5.14 (1H, d, J=5Hz), 5.36 (2H, s), 5.43 (1H, d, J=16Hz), 5.52 (1H, d, J=10Hz), 5.67 (1H, dd, J=5Hz, J=8Hz), 6.62 (1H, dd, J=10Hz, 16Hz), 7.20 (5H, s), 7.60, 8.14 (4H, ABq, J=9Hz), 9.04 (1H, d, J=8Hz)

(14) p-Nitrobenzyl 7-[2-(p-nitrobenzyloxycarbonylmethoxyimino)-2-{2-(2,2,2-trifluoroacetamido)thiazol-4-yl}acetamido]-3-vinylthio-3-cephem-4-carboxylate (syn isomer).

IR (Nujol): 1780, 1720, 1660, 1610, 1520, 1345 cm$^{-1}$

(15) p-Nitrobenzyl 7-[2-((Z)-2-cyanovinylthio)-acetamido]-3-vinylthio-3-cephem-4-carboxylate.

IR (Nujol): 3290, 2210, 1760, 1700, 1640, 1515, 1350 cm$^{-1}$

(16) 7-[2-(5-Amino-1,2,4-thiadiazol-3-yl)-2-ethoxyiminoacetamido]-3-[(Z)-2-(1,2-dimethyl-5-pyridinio)-vinylthio]-3-cephem-4-carboxylate (syn isomer).

mp: 185–195° C. (dec.)

IR (Nujol): 3450–3150, 3300, 1775, 1680, 1615, 1530, 1350

(17) 7-[2-(5-Amino-1,2,4-thiadiazol-3-yl)-2-methoxyiminoacetamido]-3-[(Z)-2-(2-methyl-5-pyridyl)-vinylthio]-3-cephem-4-carboxylic acid (syn isomer).

mp: 179–185° C. (dec.)

IR (Nujol): 3300, 3200, 1775, 1680, 1620, 1530, 1350 cm$^{-1}$

(18) Benzhydryl 7-[2-(5-amino-1,2,4-thiadiazol-3-yl)-2-methoxyiminoacetamido]-3-[(Z)-2-(2-methyl-5-pyridyl)vinylthio]-3-cephem-4-carboxylate (syn isomer).

IR (Nujol): 3300, 3150, 1780, 1670, 1610, 1600, 1530, 1280, 1220 cm$^{-1}$

(19) 7-[2-(2-Aminothiazol-4-yl)-2-methoxyiminoacetamido]-3-[(Z)-2-(1,2-dimethyl-5-pyridinio)-vinylthio]-3-cephem-4-carboxylate (syn isomer).

mp: 190–195° C. (dec.)

IR (Nujol): 3300, 3200, 1770, 1660, 1610, 1530, 1340 cm$^{-1}$

(20) Benzhydryl 7-[2-(2-formamidothiazol-4-yl)-2-methoxyiminoacetamido]-3-[(Z)-2-(1,2-dimethyl-5-pyridinio)vinylthio]-3-cephem-4-carboxylate iodide (syn isomer).

IR (Nujol): 3400, 3150, 1780, 1660, 1540, 1280, 1220 cm$^{-1}$

(21) 7-[2-(2-Aminothiazol-4-yl)-2-methoxyiminoacetamido]-3-[(Z)-2-(2-methyl-5-pyridyl)vinylthio]-3-cephem-4-carboxylic acid (syn isomer).

mp: 177–182° C. (dec.)

IR (Nujol): 3300, 3200, 1770, 1670, 1620, 1535, 1350 cm$^{-1}$

(22) Benzhydryl 7-[2-(2-aminothiazol-4-yl)-2-methoxyiminoacetamido]-3-[(Z)-2-(2-methyl-5-pyridyl)-vinylthio]-3-cephem-4-carboxylate (syn isomer).

IR (Nujol): 3300, 3150, 1780, 1670, 1610, 1535, 1490, 1280, 1220 cm$^{-1}$

(23) Benzhydryl 7-[2-(2-formamidothiazol-4-yl)-2-methoxyiminoacetamido]-3-[(Z)-2-(2-methyl-5-pyridyl)-vinylthio-3-cephem-4-carboxylate (syn isomer).

IR (Nujol): 3250, 3150, 1780, 1690, 1650, 1550, 1280, 1230 cm$^{-1}$

(24) 7-[2-(5-Amino-1,2,4-thiadiazol-3-yl)-2-ethoxyiminoacetamido]-3-[(Z)-2-(2-methyl-5-pyridyl)-vinylthio]-3-cephem-4-carboxylic acid (syn isomer).

mp: 175–180° C. (dec.)

IR (Nujol): 3300, 3150, 1770, 1670, 1610, 1530, 1290 cm$^{-1}$

(25) Benzhydryl 7-[2-(5-amino-1,2,4-thiadiazol-3-yl)-2-ethoxyiminoacetamido]-3-[(Z)-2-(2-methyl-5-pyridyl)vinylthio]-3-cephem-4-carboxylate (syn isomer).

IR (Nujol): 3300, 3150, 1780, 1670, 1610, 1530, 1280, 1220 cm$^{-1}$

(26) 7-[2-(5-Amino-1,2,4-thiadiazol-3-yl)-2-carboxymethoxyiminoacetamido]-3-[(Z)-2-(1-methyl-3-pyridinio)vinylthio]-3-cephem-4-carboxylate (syn isomer).

mp: 165–170° C. (dec.)

IR (Nujol): 3400–3100, 1760, 1630, 1600, 1510 1240 cm$^{-1}$

(27) Benzhydryl 7-[2-(5-amino-1,2,4-thiadiazol-3-yl)-2-carboxymethoxyiminoacetamido]-3-[(Z)-2-(1-methyl-3-pyridinio)vinylthio]-3-cephem-4-carboxylate iodide (syn isomer).

IR (Nujol): 3250, 3150, 1780, 1730, 1655, 1525, 1285, 1225 cm$^{-1}$

(28) 7-[2-(5-Amino-1,2,4-thiadiazol-3-yl)-2-(2-cyclopenten-1-yl)oxyiminoacetamido]-3-[(Z)-2-(3-pyridyl)-vinylthio]-3-cephem-4-carboxylic acid (syn isomer).

mp: 90–100° C. (dec.)

IR (Nujol): 3400–3100, 1770, 1660, 1525 cm$^{-1}$

(29) 7-[2-(2-Aminothiazol-4-yl)-3-hydroxypropionamido]-3-[(Z)-2-(3-pyridyl)vinylthio]-3-cephem-4-carboxylic acid.

mp: 100–110° C. (dec.)

IR (Nujol): 3200, 1770, 1670–1520, 1600, 1340, 1250 cm$^{-1}$

(30) 7-(2-Phenylacetamido)-3-vinylthio-3-cephem-4-carboxylic acid.

IR (Nujol): 3300, 1780, 1690, 1630, 1520, 1360, 1230 cm$^{-1}$

(31) 7-[2-(2-Aminothiazol-4-yl)-2-methoxyiminoacetamido]-3-vinylthio-3-cephem-4-carboxylic acid (syn isomer).

mp: 195–205° C. (dec.)

IR (Nujol): 3200, 1770, 1660, 1530 cm$^{-1}$

(32) 7-[2-Methoxyimino-2-{2-(2,2,2-trifluoroacetamido)thiazol-4-yl}acetamido]-3-vinylthio-3-cephem-4-carboxylic acid (syn isomer).

IR (Nujol): 3200, 1775, 1720, 1655, 1520, 1265, 1235, 1210 cm$^{-1}$

(32) p-Nitrobenzyl 7-[2-methoxyimino-2-{2-(2,2,2-trifluoroacetamido)thiazol-4-yl}acetamido]-3-vinylthio-3-cephem-4-carboxylate (syn isomer).

IR (Nujol): 3230, 1775, 1725, 1700, 1655, 1520, 1515, 1350, 1260, 1215 cm$^{-1}$

(34) Benzhydryl 7-[2-allyloxyimino-2-(2-formamidothiazol-4-yl)acetamido]-3-[(Z)-2-(1,2-dimethyl-5-pyridinio)vinylthio]-3-cephem-4-carboxylate iodide (syn isomer).

IR (Nujol): 1780, 1670, 1530 cm$^{-1}$

(35) Benzhydryl 7-[2-allyloxyimino-2-(2-aminothiazol-4-yl)acetamido]-3-[(Z)-2-(1,2-dimethyl-5-pyridinio)vinylthio]-3-cephem-4-carboxylate iodide (syn isomer).

IR (Nujol): 1780, 1670, 1630, 1520 cm$^{-1}$

(36) 7-[2-Allyloxyimino-2-(2-aminothiazol-4-yl)-acetamido]-3-[(Z)-2-(1,2-dimethyl-5-pyridinio)vinylthio]-3-cephem-4-carboxylate (syn isomer).

IR (Nujol): 1770, 1670, 1610, 1520 cm$^{-1}$

(37) Benzhydryl 7-[2-(2-formamidothiazol-4-yl)-2-ethoxyiminoacetamido]-3-[(Z)-2-(1,2-dimethyl-5-pyridinio)vinylthio]-3-cephem-4-carboxylate iodide (syn isomer).

NMR (DMSO-d$_6$, δ): 1.3 (3H, t, J=7Hz), 4.18 (3H, s), 5.28 (1H, d, J=5Hz), 5.90 (1H, dd, J=5Hz, 8Hz), 6.70, 7.05 (2H, ABq, J=11Hz), 6.83 (1H, s), 7.05–7.60 (11H, m), 7.90 (1H, d, J=8Hz), 8.21 (1H, d, J=8Hz), 8.40 (1H, s), 8.85 (1H, s), 9.60 (1H, d, J=8Hz)

(38) Benzhdryl 7-[2-(2-aminothiazol-4-yl)-2-ethoxyiminoacetamido]-3-[(Z)-2-(1,2-dimethyl-5-pyridinio)-vinylthio]-3-cephem-4-carboxylate iodide (syn isomer).

IR (Nujol): 1780, 1670, 1620, 1520 cm$^{-1}$

(39) 7-[2-(2-Aminothiazol-4-yl)-2-ethoxyiminoacetamido]-3-[(Z)-2-(1,2-dimethyl-5-pyridinio)-vinylthio]-3-cephem-4-carboxylate (syn isomer).

IR (Nujol): 1770, 1660, 1600, 1520 cm$^{-1}$

(40) Benzhydryl 7-[2-allyloxyimino-2-(5-amino-1,2,4-thiadiazol-3-yl)acetamido]-3-[(Z)-2-(2-methyl-5-pyridyl)vinylthio]-3-cephem-4-carboxylate (syn isomer).

IR (Nujol): 1770, 1670, 1600, 1520 cm$^{-1}$

(41) 7-[2-Allyloxyimino-2-(5-amino-1,2,4-thiadiazol-3-yl)acetamido]-3-[(Z)-2-(2-methyl-5-pyridyl)vinylthio]-3-cephem-4-carboxylic acid (syn isomer).

IR (Nujol): 1770 cm$^{-1}$

(42) Benzhydryl 7-[2-allyloxyimino-2-(2-formamidothiazol-4-yl)acetamido]-3-[(Z)-2-(2-methyl-5-pyridyl)-vinylthio]-3-cephem-4-carboxylate (syn isomer).

IR (Nujol): 1780, 1690, 1650, 1540 cm$^{-1}$

(43) Benzhydryl 7-[2-allyloxyimino-2-(2-aminothiazol-4-yl)acetamido]-3-[(Z)-2-(2-methyl-5-pyridyl)-vinylthio]-3-cephem-4-carboxylate (syn isomer).

IR (Nujol): 1780, 1670, 1610, 1530 cm$^{-1}$

(44) 7-[2-Allyloxyimino-2-(2-aminothiazol-4-yl)-acetamido]-3-[(Z)-2-(2-methyl-5-pyridyl)vinylthio]-3-cephem-4-carboxylic acid (syn isomer).

IR (Nujol): 1770, 1660, 1530 cm$^{-1}$

(45) Benzhydryl 7-[2-ethoxyimino-2-(2-formamidothiazol-4-yl)acetamido]-3-[(Z)-2-(2-methyl-5-pyridyl)-vinylthio]-3-cephem-4-carboxylate (syn isomer).

IR (Nujol): 1780, 1680, 1540 cm$^{-1}$ (46) Benzhydryl 7-[2-(2-aminothiazol-4-yl)-2-ethoxyiminoacetamido]-3-[(Z)-2-(2-methyl-5-pyridyl)-vinylthio]-3-cephem-4-carboxylate (syn isomer).

IR (Nujol): 1780, 1670, 1610, 1520 cm$^{-1}$

(47) 7-[2-(2-Aminothiazol-4-yl)-2-ethoxyiminoacetamido]-3-[(Z)-2-(2-methyl-5-pyridyl)vinylthio]-3-cephem-4-carboxylic acid (syn isomer).

IR (Nujol): 1760, 1660, 1600, 1530 cm$^{-1}$

(48) Benzhydryl 7-amino-3-[(Z)-2-(2-methyl-5-pyridyl)vinylthio]-3-cephem-4-carboxylate.

IR (Nujol): 3400, 1770, 1720, 1590, 1360, 1280 1220 cm$^{-1}$

(49) p-Nitrobenzyl 7-amino-3-vinylthio-3-cephem-4-carboxylate hydrochloride.

IR (Nujol): 1775, 1700, 1510, 1485 cm$^{-1}$

EXAMPLE 47

To a suspension of benzhydryl 7-formamido-3-[(Z)-2-(2-methyl-5-pyridyl)vinylthio]-3-cephem-4-carboxylate (17.5 g) in methanol (90 ml) was added conc. hydrochloric acid (10.0 ml) at ambient temperature and the mixture was stirred at 30° C. to 35° C. for 2.5 hours. The reaction mixture was poured into a mixture of cold water (250 ml), tetrahydrofuran (250 ml) and ethyl acetate (500 ml). The resultant mixture was adjusted to pH 7 with a saturated aqueous solution of sodium bicarbonate. The separated organic layer was washed with a saturated aqueous solution of sodium chloride, dried over magnesium sulfate and evaporated in vacuo to give benzhydryl 7-amino-3-[(Z)-2-(2-methyl-5-pyridyl)-vinylthio]-3-cephem-4-carboxylate (14.1 g).

IR (Nujol): 3400, 1770, 1720, 1590, 1360, 1280, 1220 cm$^{-1}$

NMR (DMSO-d$_6$, δ): 2.48 (3H, s), 3.67 and 4.10 (2H, ABq, J=18Hz), 4.87 (1H, d, J=5Hz), 5.11 (1H, d, J=5Hz), 6.69 (2H, s), 6.92 (1H, s), 7.1–7.8 (2H, m), 8.5 (1H, m)

EXAMPLE 48

To a suspension of phosphorus pentachloride (366 mg) in methylene chloride (6ml) was added pyridine (0.142 ml) at −30° C. After the mixture was stirred for 30 minutes at the same temperature, p-nitrobenzyl 7-(2-phenylacetamido)-3-vinylthio-3-cephem-4-carboxylate (300 mg) was added thereto at −30° C. The mixture was stirred for 1 hour under the ice-cooling to the mixture was added methanol (0.38 ml) at −30° C., and the mixture was stirred for 2 hours at −15 ~ −20° C. Water (0.4 ml) was added thereto under ice-cooling.

Diisopropyl ether (5 ml) was added to the mixture to give a precipitate. The precipitate was collected, washed with water and diisopropyl ether successively and dried over phosphorus pentoxide to give p-nitrobenzyl 7-amino-3-vinylthio-3-cephem-4-carboxylate hdrochloride (181 mg).

IR (Nujol): 1775, 1700, 1510, 1485 cm$^{-1}$

NMR (DMSO-d$_6$, δ): 3.90 (2H, broad s), 5.08 (1H, d, J=5Hz), 5.27 (1H, d, J=5Hz), 5.38 (2H, s), 5.58 (1H, d, J=17Hz), 5.64 (1H, d, J=10Hz), 6.73 (1H, dd, J=10Hz, J=17Hz), 7.60, 8.15 (4H, ABq, J=8Hz)

EXAMPLE 49

The following compounds were obtained according to a similar manner to that of Example 29.

(1) Benzhydryl 7-[2-(2-tritylaminothiazol-4-yl)-3-hydroxypropionamido]-3-[(Z)-2-(3-pyridyl)vinylthio]-3-cephem-4-carboxylate.

IR (Nujol): 3300, 1780, 1730, 1670, 1520, 1495, 1280, 1220 cm$^{-1}$ (2) Benzhydryl 7-[2-(2-formamidothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer).

IR (Nujol): 2125, 2100, 1775, 1680, 1640 cm$^{-1}$ (3) Benzhydryl 7-[2-(2-aminothiazol-4-yl)-2-methoxyiminoacetamido]-3-[(Z)-2-{1-(2-azidoethyl)-3-pyridinio}vinylthio]-3-cephem-4-carboxylate trifluoromethanesulfonate (syn isomer).

IR (Nujol): 2130, 2100, 1780, 1670, 1630 cm$^{-1}$ (4) Benzhydryl 7-[2-(2-aminothiazol-4-yl)-2-methoxyiminoacetamido]-3-[(Z)-2-(1,2-dimethyl-5-pyridinio)-vinylthio]-3-cephem-4-carboxylate iodide hydrochloride (syn isomer).

IR (Nujol): 3350, 3150, 1780, 1670, 1630, 1565, 1545, 1275, 1220 cm$^{-1}$ (5) p-Nitrobenzyl 7-[2-(5-amino-1,2,4-thiadiazol-3-yl)-2-ethoxyiminoacetamido]-3-vinylthio-3-cephem-4-carboxylate (syn isomer).

IR (Nujol): 1770, 1680, 1615, 1525, 1455 cm$^{-1}$ (6) Benzhydryl 7-formamido-3-[(Z)-2-(2-methyl-5-pyridyl)vinylthio]-3-cephem-4-carboxylate.

IR (Nujol): 3150, 1780, 1710, 1690, 1230, 1220 cm$^{-1}$ (7) p-Nitrobenzyl 7-(2-phenylacetamido)-3-vinylthio-3-cephem-4-carboxylate.

IR (Nujol): 3280, 1970, 1705, 1665, 1540, 1520 cm$^{-1}$ (8) p-Nitrobenzyl 7-[2-(p-nitrobenzyloxycarbonylmethoxyimino)-2-{2-(2,2,2-trifluoroacetamido)thiazol-4-yl}acetamido]-3-vinylthio-3-cephem-4-carboxylate (syn isomer).

IR (Nujol): 1780, 1720, 1660, 1610, 1520, 1345 cm$^{-1}$ (9) p-Nitrobenzyl 7-[2-((Z)-2-cyanovinylthio)acetamido]-3-vinythio-3-cephem-4-carboxylate.

IR (Nujol): 3290, 2210, 1760, 1700, 1640, 1515, 1350 cm$^{-1}$

(10) Benzhydryl 7-[2-(5-amino-1,2,4-thiadiazol-3-yl)-2-methoxyiminoacetamido]-3-[(Z)-2-(2-methyl-5-pyridyl)vinylthio]-3-cephem-4-carboxylate (syn isomer).

IR (Nujol): 3300, 3150, 1780, 1670, 1610, 1600, 1530, 1280, 1220 cm$^{-1}$

(11) Benzhydryl 7-[2-(2-formamidothiazol-4-yl)-2-methoxyiminoacetamido]-3-[(Z)-2-(1,2-dimethyl-5-pyridinio)vinylthio]-3-cephem-4-carboxylate iodide (syn isomer).

IR (Nujol): 3400, 3150, 178-, 1660, 1540, 1280, 1220 cm$^{-1}$

(12) Benzhydryl 7-[2-(2-aminothiazol-4-yl)-2-methoxyiminoacetamido]-3-[(Z)-2-(2-methyl-5-pyridyl)-vinylthio]-3-cephem-4-carboxylate (syn isomer).

IR (Nujol): 3300, 3150, 1780, 1670, 1610, 1535, 1490, 1280, 1220 cm$^{-1}$

(13) Benzhydryl 7-[2-(2-formamidothiazol-4-yl)-2-methoxyiminoacetamido]-3-[(Z)-2-(2-methyl-5-pyridyl)-vinylthio]-3-cephem-4-carboxylate (syn isomer).

IR (Nujol): 3250, 3150, 1780, 1690, 1650, 1550, 1280, 1230 cm$^{-1}$

(14) Benzhydryl 7-[2-(5-amino-1,2,4-thiadiazol-3-yl)-2-ethoxyiminoacetamido]-3-[(Z)-2-(2-methyl-5-pyridyl)vinylthio]-3-cephem-4-carboxylate (syn isomer)

IR (Nujol): 3300, 3150, 1780, 1670, 1610, 1530, 1280, 1220 cm$^{-1}$

(15) Benzhydryl 7-[2-(5-amino-1,2,4-thiadiazol-3-yl)-2-carboxymethoxyiminoacetamido]-3-[(Z)-2-(1-methyl-3-pyridinio)vinylthio]-3-cephem-4-carboxylate iodide (syn isomer).

IR (Nujol): 3250, 3150, 1780, 1730, 1655, 1525, 1285, 1225 cm$^{-1}$

(16) p-Nitrobenzyl 7-[2-methoxyimino-2-{2-(2,2,2-trifluoroacetamido)thiazol-4-yl}acetamido]-3-vinylthio-3-cephem-4-carboxylate (syn isomer).

IR (Nujol): 3230, 1775, 1725, 1700, 1655, 1520, 1515, 1350, 1260, 1215 cm$^{-1}$

(17) Benzhydryl 7-[2-allyloxyimino-2-(2-formamidothiazol-4-yl)acetamido]-3-[(Z)-2-(1,2-dimethyl-5-pyridinio)vinylthio]-3-cephem-4-carboxylate iodide (syn isomer).

IR (Nujol): 1780, 1670, 1530 cm$^{-1}$

(18) Benzhydryl 7-[2-allyloxyimino-2-(2-aminothiazol-4-yl)acetamido]-3-[(Z)-2-(1,2-dimethyl-5-pyridinio)vinylthio]-3-cephem-4-carboxylate iodide (syn isomer).

IR (Nujol): 1780, 1670, 1630, 1520 cm$^{-1}$

(19) Benzhydryl 7-[2-(2-formamidothiazol-4-yl)-2-ethoxyiminoacetamido]-3-[(Z)-2-(1,2-dimethyl-5-pyridinio)vinylthio]-3-cephem-4-carboxylate iodide (syn isomer).

NMR (DMSO-d$_6$, δ): 1.3 (3H, t, J=7Hz), 4.18 (3H, s), 5.28 (1H, d, J=5Hz), 5.90 (1H, dd, J=5Hz, 8Hz), 6.70, 7.05 (2H, ABq, J=11Hz), 6.83 (1H, s), 7.05–7.60 (11H, m), 7.90 (1H, d, J=8Hz), 8.21 (1H, d, J=8Hz), 8.40 (1H, s), 8.85 (1H, s), 9.60 (1H, d, J=8Hz)

(20) Benzhydryl 7-[2-(2-aminothiazol-4-yl)-2-ethoxyiminoacetamido]-3-[(Z)-2-(1,2-dimethyl-5-pyridinio)-vinylthio]-3-cephem-4-carboxylate iodide (syn isomer).

IR (Nujol): 1780, 1670, 1620, 1520 cm$^{-1}$

(21) Benzhydryl 7-[2-allyloxyimino-2-(5-amino-1,2,4-thiadiazol-3-yl)acetamido]-3-[(Z)-2-(2-methyl-5-pyridyl)vinylthio]-3-cephem-4-carboxylate (syn isomer)

IR (Nujol): 1770, 1670, 1600, 1520 cm$^{-1}$

(22) Benzhydryl 7-[2-allyloxyimino-2-(2-formamidothiazol-4-yl)acetamido]-3-[(Z)-2-(2-methyl-5-pyridyl)-vinylthio]-3-cephem-4-carboxylate (syn isomer).

IR (Nujol): 1780, 1690, 1650, 1540 cm$^{-1}$

(23) Benzhydryl 7-[2-allyloxyimino-2-(2-aminothiazol-4-yl)acetamido]-3[(Z)-2-(2-methyl-5-pyridyl)-vinylthio]-3-cephem-4-carboxylate (syn isomer).

IR (Nujol): 1780, 1670, 1610, 1530 cm$^{-1}$

(24) Benzhydryl 7-[2-ethoxyimino-2-(2-formamidothiazol-4-yl)acetamido]-3-[(Z)-2-(2-methyl-5-pyridyl)-vinylthio]-3-cephem-4-carboxylate (syn isomer).

IR (Nujol): 1780, 1680, 1540 cm$^{-1}$

(25) Benzhydryl 7-[2-(2-aminothiazol-4-yl)-2-ethoxyiminoacetamido]-3-[(Z)-2-(2-methyl-5-pyridyl)-vinylthio]-3-cephem-4-carboxylate (syn isomer).

IR (Nujol): 1780, 1670, 1610, 1520 cm$^{-1}$

(26) Benzhydryl 7-amino-3-[(Z)-2-(2-methyl-5-pyridyl)vinylthio]-3-cephem-4-carboxylate.

IR (Nujol): 3400, 1770, 1720, 1590, 1360, 1280, 1220 cm$^{-1}$

(27) p-Nitrobenzyl 7-amino-3-vinylthio-3-cephem-4-carboxylate hydrochloride.

IR (Nujol): 1775, 1700, 1510, 1485 cm$^{-1}$

What we claim is:

1. A cephem compound of the formula:

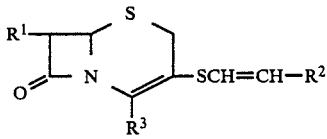

wherein R$^1$ is a group of the formula:

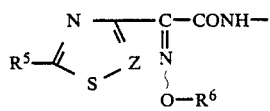

in which

R$^5$ is amino or protected amino,

R$^6$ is hydrogen, lower alkyl, lower alkenyl, lower alkynyl, carboxy(lower) alkyl, protected carboxy(lower)alkyl, cyclo(lower)alkyl or cyclo(lower)alkenyl, and Z is CH or N;

R$^2$ is hydrogen, phenyl, pipedyl which may have a lower alkyl group or cyano; and R$^3$ is carboxy or protected carboxy; and pharmaceutically acceptable salt thereof.

2. A compound of claim 1, wherein
R$^2$ is pyridyl, lower alkylpyridyl, phenyl cyano or hydrogen, 3. A compound of claim 2,
wherein
R$^5$ is amino or acylamino;
R$^6$ is hydrogen, lower alkyl, lower alkenyl, lower alkynyl, carboxy(lower) alkyl, esterified carboxy(lower)alkyl, cyclo(lower) alkyl or cyclo(lower)alkenyl;
R$^3$ is carboxy or esterified carboxy.

4. A compound of claim 1, wherein R$^2$ is hydrogen.

5. A compound of claim 1,
wherein R$^2$ is phenyl.

6. A compound of claim 1,
wherein R$^2$ is pyridyl which
may have a lower alkyl group.

7. A compound of claim 6,
wherein R$^2$ is pyridyl or lower alkylpyridyl.

8. A compound of claim 1,
wherein R$^2$ is cyano.

9. An antimicrobial pharmaceutical composition comprising an effective amount of a compound of claim 4, or pharmaceutically acceptable salt thereof in association with a pharmaceutically acceptable, substantially non-toxic carrier or excipient.

10. An antimicrobial method for producing a pharmaceutical composition which comprises mixing an effective amount of a compound of claim 1 or pharmaceutically acceptable salt thereof as an active ingredient with an inert carrier.

11. A method for treatment of infectious diseases in human beings and animals which comprises administering an effective amount of the compound of claim 1 to the human or animal in need of such treatment.

* * * * *